United States Patent
Whitsett et al.

(10) Patent No.: US 7,951,532 B2
(45) Date of Patent: May 31, 2011

(54) METHOD OF SCREENING A MIDKINE MODULATING AGENT

(75) Inventors: Jeffrey A. Whitsett, Cincinnati, OH (US); Michael Mucenski, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 0 days.

(21) Appl. No.: 10/988,486

(22) Filed: Nov. 12, 2004

(65) Prior Publication Data

US 2005/0130928 A1  Jun. 16, 2005

Related U.S. Application Data

(60) Provisional application No. 60/519,473, filed on Nov. 12, 2003, provisional application No. 60/541,580, filed on Feb. 4, 2004, provisional application No. 60/580,481, filed on Jun. 17, 2004.

(51) Int. Cl.
*C12Q 1/68* (2006.01)
*C12Q 1/66* (2006.01)
*C12N 15/67* (2006.01)

(52) U.S. Cl. ................ 435/6; 435/8; 435/455
(58) Field of Classification Search ............. 435/6, 8, 435/455
See application file for complete search history.

(56) References Cited

U.S. PATENT DOCUMENTS

| | | | |
|---|---|---|---|
| 5,013,720 | A | 5/1991 | Whitsett |
| 5,834,306 | A | 11/1998 | Webster et al. |
| 5,837,534 | A | 11/1998 | Olson et al. |
| 5,976,873 | A | 11/1999 | Bohinski et al. |
| 6,015,711 | A | 1/2000 | Olson et al. |
| 6,201,165 | B1 | 3/2001 | Grant et al. |
| 6,364,912 | B1 | 4/2002 | Peterson et al. |
| 2001/0016352 | A1 | 8/2001 | Bohinski et al. |
| 2002/0034768 | A1 | 3/2002 | Wellstein |
| 2002/0110539 | A1 | 8/2002 | Zhu et al. |
| 2002/0197646 | A1 | 12/2002 | Nogee et al. |
| 2003/0053989 | A1 | 3/2003 | Kovesdi |
| 2003/0065157 | A1 | 4/2003 | Lasek |
| 2003/0104499 | A1 | 6/2003 | Pressman et al. |
| 2003/0118567 | A1 | 6/2003 | Stewart |
| 2003/0124580 | A1 | 7/2003 | Walker et al. |
| 2003/0157065 | A1* | 8/2003 | Tagawa .................. 424/93.2 |
| 2006/0099188 | A1 | 11/2006 | Tagawa |

FOREIGN PATENT DOCUMENTS

| EP | 1283 255 A1 | 2/2003 |
|---|---|---|
| EP | 1 302 539 A | 4/2003 |
| EP | 04 81 0730 | 4/2008 |
| WO | PCT/US2004/037623 | 5/2005 |

OTHER PUBLICATIONS

Goodman & Gilman's The Pharmacological basis of Therapeutics, McGraw-Hill, New York, NY. pp. 77-101.*
Kato et al J Neuropathol Exp Neurol. 1999; 58(5):430-41.*
Cheung et al Nature Genetics, 2003, 33, 422-425.*
Hoshikawa et al Physiol Genomics 12: 209-219, 2003.*
Garver et al Am J Respir Cell Mol Biol. 1993; 9(5):463-6.*
Matsuura et al Cell Struct Funct. 2002; 27(2):109-15.*
You et al BMC Med Genomics. Feb. 14, 2008;1:6.*
Ishimoto J Clin Endocrinol Metab. Oct. 2006;91(10):4050-6.*
Adachi Y., et al Midkine as a novel target gene for the Wilms' tumor suppressor gene (WT1). Oncogene (1996) pp. 2197-2203 (Abstract) v.13, #10.
Choudhuri R., et al. "An angiogenic role for the neurokines midkine and pleiotrophin in tumorigenesis." Cancer Res. (1997) pp. 1814-1819. (Abstract) v.57, #9.
Perl, et al. "Molecular mechanisms controlling lung morphogenesis." Clinical Genetics (1999) p14 v.56 #1.
Paul, S. et al.. "Molecular cloning, expression, and purification of truncated midkine and its growth stimulatory activity on Wilms' tumor (G401) cells." Cancer Lett (2001) pp. 239-244, v. 163.
Nauser, T. et al. "Diagnosis and Treatment of Pulmonary Hypertension" American Family Physician (2001) pp. 1789-1798 v.63 #9.
Yoshida Y., et al "A promoter region of midkine gene can activate transcription of exogenous suicide gene in pancreatic cancer." Anticancer Research. (2002) pp. 117-120 v.22.
Wert, et al. "Increased expression of thyroid transcription factor-1 (TTF-1) in respiratory epithelial cells inhibits alveolization and causes pulmonary inflammation " Developmental Biology 2002 pp. 75-87 v. 242.
Reynolds et al. J. B.C. Midkine is Regulated by Hypoxia and Causes Pulmonary Vascular Remodeling (2004) 279:37124-37132.
"Chronic Obstructive Pulmonary Disease" Data Fact Sheet U.S. Department of Health and Human Services, National Institutes of Health, National Heart, Lung, and Blood Institute. NIH publication No. 03-5229. Mar. 2003.
Reynolds et al. "Thyroid Transcription Factor (TTF)-1 Regulates the Expression of Midkine (MK) During Lung Morphogenesis" Developmental Dynamics (2003) pp. 227-237 v. 227.
Tomizawa, et al "Regulatory Regions of growth-related genes can activate an exogenous gene of the alpha-fetoprotein to a comparable degree in human hepatocellular carcinoma cells" AntiCancer Research. 2003 pp. 3273-3277 v. 23, No. 4.
Yu, et al. "Cell growth- and P53-dependent transcriptional activity of the midkine promoter confers suicide gene expression in tumor cell." Oncology Report (2003) pp. 1301-1305 v. 10.
Kaplan et al "The Growth Factor Midkine is Modulated by Both Glucocorticoid and Retinoids in Fetal Lung Development." American Journal Respiratory Cell and Molecular Biology 2003 pp. 33-41, vol. 28.
Reynolds et al, Thyroid Transcription Factor (TTF) . . . , (Dev Dyn. 2003; 227(2): 227-237), @ 2003 Wiley-Liss, Inc. USA.

(Continued)

*Primary Examiner* — Anoop Singh
(74) *Attorney, Agent, or Firm* — Knobbe Martens Olson & Bear LLP

(57) ABSTRACT

This invention relates to the discovery that midkine modulates pulmonary vasculature development and smooth muscle cell development. Modulation of midkine activity thus alters pulmonary vasculature development and smooth muscle cell development. The invention provides methods of modulating pulmonary disorders, smooth muscle cell related disorders, and pulmonary smooth muscle cell disorders. Disorders of particular interest include, but are not limited to, asthma and pulmonary hyperplasia. Further the invention relates to the discovery that TTF1 and HIF1-α exhibit midkine modulating activity. The invention pertains to the discovery that midkine modulates myocardin activity.

39 Claims, 17 Drawing Sheets

OTHER PUBLICATIONS

Boshoff et al. Differential Basal Synthesis of Hsp70/Hsc70 contributes to interindividual variation in Hsp70/Hsc70 inducibility, Cell Mol Life Sci, 2000 57:8 1317-25.

Gervois et al., A Truncated Human Peroxisome Proliferator Activated Receptor alpha Splice Variant with Dominant Negative Activity, Molecular Endocrinology 1999 13-9 1535-49.

Gutierrez-Rios et al, Regulatory Network of *Escherichia coli*: Consistency between Literature Knowledge and Microarray Profiles, Genome Research 2003 13:2435-2443.

Adachi et al, "Midkine Promoter-based Adenoviral Vector Gene Delivery for Pediatric Solid Tumors", Cancer Research, Aug. 15, 2000, 4305-4310, 60-16.

Durmowicz, "Mechanisms of Structural Remodeling in Chronic Pulmonary Hypertension", Pediatrics in Review, 1999, e91-e102, v.20.

Matsubara et al, Structure of a Retinoic Acid-responsive Gene, MKn which is Transiently Activated During the Differentiation of Embryonal Carcinoma Cells and the Mid-Gestation Period of Mouse Embryogenesis, Journal of Biological Chemistry, Jun. 5, 1990, 9441-9443, 265-14.

\* cited by examiner

|  | Normoxic | | Hypoxic | |
|---|---|---|---|---|
|  | control (n=7) | SP-C-rtTA$^{+/tg}$, (tetO)$_7$-CMV-MK$^{+/tg}$ or tg/tg (n=8) | control (n=8) | SP-C-rtTA$^{+/tg}$, (tetO)$_7$-CMV-MK$^{+/tg}$ or tg/tg (n=8) |
| RVH | 0.39±0.03 | 0.42±0.04 | 0.42±0.06 | 0.49±0.06* |
| No. distal vessels | 34.5±2.1 | 46.6±3.8* | 32.7±4.5 | 46.3±3.2* |
| % Muscularization | 40.16±6.03 | 77.48±2.93* | 45.8±3.2 | 75.8±3.3* |

FIG. 7

SEQUENCE LISTING

<160> NUMBER OF SEQ ID NOS: 26

<210> SEQ ID NO 1
<211> LENGTH: 881
<212> TYPE: DNA

```
<213> ORGANISM: Mus musculus
<220> FEATURE:
<221> NAME/KEY: CDS
<222> LOCATION: (197)...(619)
<223> OTHER INFORMATION: Midkine

<400> SEQUENCE: 1
ggcacgaggg gagcgaagca tcgagcagtg agcgagtgag cgcacgcagt ggctgtggcc      60 ccagtcccctt caggcggctg ctctgccacc aaggggggctg aggtgggggt ggggtacgc   120 tgagacatcg gttccaagtc ctccctccgt ctcccccttg tcggtccgac gttttgggcc    180
tggaaagtgg gacaag atg cag cac cga ggc ttc ttc ctt ctc gcc ctt ctt    232
               Met Gln His Arg Gly Phe Phe Leu Leu Ala Leu Leu
                 1               5                  10 gcc ctc ttg gtg gtc acg tcc gcg gtg gcc aaa aaa aaa gag aag gtg      280
Ala Leu Leu Val Val Thr Ser Ala Val Ala Lys Lys Lys Glu Lys Val
            15                  20                  25 aag aag ggc agc gag tgt tcg gag tgg acc tgg ggg ccc tgc acc ccc      328
Lys Lys Gly Ser Glu Cys Ser Glu Trp Thr Trp Gly Pro Cys Thr Pro
        30                  35                  40 agc agc aag gac tgc ggc atg ggc ttc cgc gag ggt acc tgt ggg gcc      376
Ser Ser Lys Asp Cys Gly Met Gly Phe Arg Glu Gly Thr Cys Gly Ala
45                  50                  55                  60 cag acc cag cgc gtc cat tgc aag gtg ccc tgc aac tgg aag aag gaa      424
Gln Thr Gln Arg Val His Cys Lys Val Pro Cys Asn Trp Lys Lys Glu
                65                  70                  75 ttt gga gcc gac tgc aaa tac aag ttt gag agc tgg ggg gcg tgt gat      472
Phe Gly Ala Asp Cys Lys Tyr Lys Phe Glu Ser Trp Gly Ala Cys Asp
            80                  85                  90 ggg agc act ggc acc aaa gcc cgc caa ggg acc ctg aag aag gcg cgg      520
Gly Ser Thr Gly Thr Lys Ala Arg Gln Gly Thr Leu Lys Lys Ala Arg
        95                  100                 105 tac aat gcc cag tgc cag gag acc atc cgc gtg act aag ccc tgc acc      568
Tyr Asn Ala Gln Cys Gln Glu Thr Ile Arg Val Thr Lys Pro Cys Thr
    110                 115                 120 tcc aag acc aag tca aag acc aaa gcc aag aaa gga aaa gga aag gac      616
Ser Lys Thr Lys Ser Lys Thr Lys Ala Lys Lys Gly Lys Gly Lys Asp
125                 130                 135                 140 taa gtcaggaggc cagagagcct ccggcctcgc ctggagcctg aacggagccc           669
* tcctctccca caggcccaag atataaccca ccagtgcctt ttgtcttcct gtcagctctg    729
tcaatcacgc ctgtcctcta cgcccacacc aagtgcccaa agtggggagg acaagagat     789 tttgaaagt gagcctccca taccctcttt tgttctcccc accctgatac ttgttattaa     849
aaaatgaata aataaactc acttttttca at                                   881

<210> SEQ ID NO 2
<211> LENGTH: 140
<212> TYPE: PRT
<213> ORGANISM: Mus musculus

<400> SEQUENCE: 2

Met Gln His Arg Gly Phe Phe Leu Leu Ala Leu Leu Ala Leu Leu Val
  1               5                  10                  15

Val Thr Ser Ala Val Ala Lys Lys Lys Glu Lys Val Lys Lys Gly Ser
             20                  25                  30

Glu Cys Ser Glu Trp Thr Trp Gly Pro Cys Thr Pro Ser Ser Lys Asp
         35                  40                  45

Cys Gly Met Gly Phe Arg Glu Gly Thr Cys Gly Ala Gln Thr Gln Arg
     50                  55                  60
```

| | | | | | | | | | | | | |
|---|---|---|---|---|---|---|---|---|---|---|---|---|
|Val|His|Cys|Lys|Val|Pro|Cys|Asn|Trp|Lys|Lys|Glu|Phe|Gly|Ala|Asp|
|65| | | |70| | | |75| | | |80|

Cys Lys Tyr Lys Phe Glu Ser Trp Gly Ala Cys Asp Gly Ser Thr Gly
                85                  90                  95

Thr Lys Ala Arg Gln Gly Thr Leu Lys Lys Ala Arg Tyr Asn Ala Gln
            100                 105                 110

Cys Gln Glu Thr Ile Arg Val Thr Lys Pro Cys Thr Ser Lys Thr Lys
        115                 120                 125

Ser Lys Thr Lys Ala Lys Lys Gly Lys Gly Lys Asp
130                 135                 140

<210> SEQ ID NO 3
<211> LENGTH: 1119
<212> TYPE: DNA
<213> ORGANISM: Mus musculus
<220> FEATURE:
<221> NAME/KEY: CDS
<222> LOCATION: (1)...(1119)
<223> OTHER INFORMATION: TTF-1

<400> SEQUENCE: 3

```
atg tcg atg agt cca aag cac acg act ccg ttc tca gtg tct gac atc      48
Met Ser Met Ser Pro Lys His Thr Thr Pro Phe Ser Val Ser Asp Ile
1               5                   10                  15 ttg agt ccc ctg gag gaa agc tac aag aaa gtg ggc atg gag ggc ggc      96
Leu Ser Pro Leu Glu Glu Ser Tyr Lys Lys Val Gly Met Glu Gly Gly
                20                  25                  30 ggc ctc ggg gct ccg ctc gca gcg tac aga cag ggc cag gcg gcc cca     144
Gly Leu Gly Ala Pro Leu Ala Ala Tyr Arg Gln Gly Gln Ala Ala Pro
            35                  40                  45 ccg gcc gcg gcc atg cag cag cac gcc gtg ggg cac cac ggc gcc gtc     192
Pro Ala Ala Ala Met Gln Gln His Ala Val Gly His His Gly Ala Val
        50                  55                  60 acc gcc gcc tac cac atg acg gcg gcg ggg gtg ccc cag ctc tcg cac     240
Thr Ala Ala Tyr His Met Thr Ala Ala Gly Val Pro Gln Leu Ser His
65                  70                  75                  80 tcc gcc gtg ggg ggc tac tgc aac ggc aac ctg ggc aac atg agc gag     288
Ser Ala Val Gly Gly Tyr Cys Asn Gly Asn Leu Gly Asn Met Ser Glu
                85                  90                  95 ctg ccg cct tac cag gac acc atg cgg aac agc gct tcg ggc ccc gga     336
Leu Pro Pro Tyr Gln Asp Thr Met Arg Asn Ser Ala Ser Gly Pro Gly
                100                 105                 110 tgg tac ggc gcc aac cca gac ccg cgc ttc ccc gcc atc tcc cgc ttc     384
Trp Tyr Gly Ala Asn Pro Asp Pro Arg Phe Pro Ala Ile Ser Arg Phe
            115                 120                 125 atg ggc ccg gcg agc ggc atg aat atg agc ggc atg ggc ggc ctg ggc     432
Met Gly Pro Ala Ser Gly Met Asn Met Ser Gly Met Gly Gly Leu Gly
        130                 135                 140 tcg ctg ggg gac gtg agc aag aac atg gcc ccg ctg ccc agt gcg ccc     480
Ser Leu Gly Asp Val Ser Lys Asn Met Ala Pro Leu Pro Ser Ala Pro
145                 150                 155                 160 cgc cgg aag cgc cgg gtg ctc ttc tcc cag gcg cag gtg tac gag ctc     528
Arg Arg Lys Arg Arg Val Leu Phe Ser Gln Ala Gln Val Tyr Glu Leu
                165                 170                 175 gag cga cgt ttc aag caa cag aag tac ctg tcg gcg ccg gag cgc gag     576
Glu Arg Arg Phe Lys Gln Gln Lys Tyr Leu Ser Ala Pro Glu Arg Glu
                180                 185                 190 cat ctg gcc agc atg att cac ctg aca ccc acg cag gtc aag atc tgg     624
His Leu Ala Ser Met Ile His Leu Thr Pro Thr Gln Val Lys Ile Trp
            195                 200                 205
```

```
ttc cag aac cac cgc tac aag atg aag cgc cag gct aag gac aag gcg    672
Phe Gln Asn His Arg Tyr Lys Met Lys Arg Gln Ala Lys Asp Lys Ala
    210                 215                 220 gcg cag caa caa ctg cag cag gac agc ggc ggc gga ggc ggc ggt       720
Ala Gln Gln Gln Leu Gln Gln Asp Ser Gly Gly Gly Gly Gly Gly
225                 230                 235                 240 ggc ggt gcg gga tgc ccg cag cag cag caa gct cag cag cag tcg ccg    768
Gly Gly Ala Gly Cys Pro Gln Gln Gln Gln Ala Gln Gln Gln Ser Pro
                245                 250                 255 cgc cgg gtg gcc gtg ccg gtc cta gtc aaa gac ggc aaa ccc tgc cag    816
Arg Arg Val Ala Val Pro Val Leu Val Lys Asp Gly Lys Pro Cys Gln
            260                 265                 270 gcg ggc gcc cct gcc ccg gga gcc gca agc ctg caa agc cac gcg cag    864
Ala Gly Ala Pro Ala Pro Gly Ala Ala Ser Leu Gln Ser His Ala Gln
275                 280                 285 caa caa gct cag cag cag gcg cag gcg gcg caa gcg gct gcc gcg gcc    912
Gln Gln Ala Gln Gln Gln Ala Gln Ala Ala Gln Ala Ala Ala Ala Ala
        290                 295                 300 atc tca gtg ggc agc ggt ggc gcg ggt cta gga gca cac cca ggc cac    960
Ile Ser Val Gly Ser Gly Gly Ala Gly Leu Gly Ala His Pro Gly His
305                 310                 315                 320 cag ccg ggc agc gca ggg cag tcc ccg gac ctg gcg cac cac gca gcc   1008
Gln Pro Gly Ser Ala Gly Gln Ser Pro Asp Leu Ala His His Ala Ala
                325                 330                 335 agc ccc gcg ggg ctg cag ggc cag gtc tcc agc cta tcc cat ctg aac   1056
Ser Pro Ala Gly Leu Gln Gly Gln Val Ser Ser Leu Ser His Leu Asn
            340                 345                 350 tcc tcg ggc tcg gac tat ggc gcc atg tct tgt tct acc ttg ctt tat   1104
Ser Ser Gly Ser Asp Tyr Gly Ala Met Ser Cys Ser Thr Leu Leu Tyr
        355                 360                 365 ggt cgg acc tgg tga                                               1119
Gly Arg Thr Trp *
    370

<210> SEQ ID NO 4
<211> LENGTH: 372
<212> TYPE: PRT
<213> ORGANISM: Mus musculus

<400> SEQUENCE: 4

Met Ser Met Ser Pro Lys His Thr Thr Pro Phe Ser Val Ser Asp Ile
1               5                   10                  15

Leu Ser Pro Leu Glu Glu Ser Tyr Lys Lys Val Gly Met Glu Gly Gly
            20                  25                  30

Gly Leu Gly Ala Pro Leu Ala Ala Tyr Arg Gln Gly Gln Ala Ala Pro
        35                  40                  45

Pro Ala Ala Ala Met Gln Gln His Ala Val Gly His His Gly Ala Val
    50                  55                  60

Thr Ala Ala Tyr His Met Thr Ala Ala Gly Val Pro Gln Leu Ser His
65                  70                  75                  80

Ser Ala Val Gly Gly Tyr Cys Asn Gly Asn Leu Gly Asn Met Ser Glu
                85                  90                  95

Leu Pro Pro Tyr Gln Asp Thr Met Arg Asn Ser Ala Ser Gly Pro Gly
            100                 105                 110

Trp Tyr Gly Ala Asn Pro Asp Pro Arg Phe Pro Ala Ile Ser Arg Phe
        115                 120                 125

Met Gly Pro Ala Ser Gly Met Asn Met Ser Gly Met Gly Gly Leu Gly
    130                 135                 140

Ser Leu Gly Asp Val Ser Lys Asn Met Ala Pro Leu Pro Ser Ala Pro
```

```
                145                 150                 155                 160
Arg Arg Lys Arg Val Leu Phe Ser Gln Ala Gln Val Tyr Glu Leu
                    165                 170                 175

Glu Arg Arg Phe Lys Gln Gln Lys Tyr Leu Ser Ala Pro Glu Arg Glu
                        180                 185                 190

His Leu Ala Ser Met Ile His Leu Thr Pro Thr Gln Val Lys Ile Trp
            195                 200                 205

Phe Gln Asn His Arg Tyr Lys Met Lys Arg Gln Ala Lys Asp Lys Ala
            210                 215                 220

Ala Gln Gln Leu Gln Gln Asp Ser Gly Gly Gly Gly Gly Gly
225                 230                 235                 240

Gly Gly Ala Gly Cys Pro Gln Gln Gln Ala Gln Gln Ser Pro
                245                 250                 255

Arg Arg Val Ala Val Pro Val Leu Val Lys Asp Gly Lys Pro Cys Gln
                260                 265                 270

Ala Gly Ala Pro Ala Pro Gly Ala Ala Ser Leu Gln Ser His Ala Gln
            275                 280                 285

Gln Gln Ala Gln Gln Ala Gln Ala Ala Gln Ala Ala Ala Ala
        290                 295                 300

Ile Ser Val Gly Ser Gly Ala Gly Leu Gly Ala His Pro Gly His
305                 310                 315                 320

Gln Pro Gly Ser Ala Gly Gln Ser Pro Asp Leu Ala His Ala Ala
                325                 330                 335

Ser Pro Ala Gly Leu Gln Gly Gln Val Ser Ser Leu Ser His Leu Asn
            340                 345                 350

Ser Ser Gly Ser Asp Tyr Gly Ala Met Ser Cys Ser Thr Leu Leu Tyr
            355                 360                 365

Gly Arg Thr Trp
    370

<210> SEQ ID NO 5
<211> LENGTH: 3973
<212> TYPE: DNA
<213> ORGANISM: Mus musculus
<220> FEATURE:
<221> NAME/KEY: CDS
<222> LOCATION: (258)...(2768)
<223> OTHER INFORMATION: HIF1alpha

<400> SEQUENCE: 5
cgcgaggact gtcctcgccg ccgtcgcggg cagtgtctag ccaggccttg acaagctagc      60
cggaggagcg cctaggaacc cgagccggag ctcagcgagc gcagcctgca cgcccgcctc     120
gcgtcccggg ggggtcccgc ctcccacccc gcctctggac ttgtctcttt ccccgcgcgc     180
gcggacagag ccggcgttta ggcccgagcg agcccggggg ccgccggccg ggaagacaac     240
gcgggcaccg attcgcc atg gag ggc gcc ggc ggc gag aac gag aag aaa        290
                   Met Glu Gly Ala Gly Gly Glu Asn Glu Lys Lys
                    1               5                   10 aag atg agt tct gaa cgt cga aaa gaa aag tct aga gat gca gca aga      338
Lys Met Ser Ser Glu Arg Arg Lys Glu Lys Ser Arg Asp Ala Ala Arg
            15                  20                  25 tct cgg cga agc aaa gag tct gaa gtt ttt tat gag ctt gct cat cag      386
Ser Arg Arg Ser Lys Glu Ser Glu Val Phe Tyr Glu Leu Ala His Gln
        30                  35                  40 ttg cca ctt ccc cac aat gtg agc tca cat ctt gat aaa gct tct gtt      434
Leu Pro Leu Pro His Asn Val Ser Ser His Leu Asp Lys Ala Ser Val
    45                  50                  55
```

```
atg agg ctc acc atc agt tat tta cgt gtg aga aaa ctt ctg gat gcc    482
Met Arg Leu Thr Ile Ser Tyr Leu Arg Val Arg Lys Leu Leu Asp Ala
 60              65                  70                  75 ggt ggt cta gac agt gaa gat gag atg aag gca cag atg gac tgt ttt    530
Gly Gly Leu Asp Ser Glu Asp Glu Met Lys Ala Gln Met Asp Cys Phe
                 80                  85                  90 tat ctg aaa gcc cta gat ggc ttt gtg atg gtg cta aca gat gac ggc    578
Tyr Leu Lys Ala Leu Asp Gly Phe Val Met Val Leu Thr Asp Asp Gly
             95                 100                 105 gac atg gtt tac att tct gat aac gtg aac aaa tac atg ggg tta act    626
Asp Met Val Tyr Ile Ser Asp Asn Val Asn Lys Tyr Met Gly Leu Thr
        110                 115                 120 cag ttt gaa cta act gga cac agt gtg ttt gat ttt act cat cca tgt    674
Gln Phe Glu Leu Thr Gly His Ser Val Phe Asp Phe Thr His Pro Cys
    125                 130                 135 gac cat gag gaa atg aga gaa atg ctt aca cac aga aat ggc cca gtg    722
Asp His Glu Glu Met Arg Glu Met Leu Thr His Arg Asn Gly Pro Val
140                 145                 150                 155 aga aaa ggg aaa gaa cta aac aca cag cgg agc ttt ttt ctc aga atg    770
Arg Lys Gly Lys Glu Leu Asn Thr Gln Arg Ser Phe Phe Leu Arg Met
                160                 165                 170 aag tgc acc cta aca agc cgg ggg agg acg atg aac atc aag tca gca    818
Lys Cys Thr Leu Thr Ser Arg Gly Arg Thr Met Asn Ile Lys Ser Ala
            175                 180                 185 acg tgg aag gtg ctt cac tgc acg ggc cat att cat gtc tat gat acc    866
Thr Trp Lys Val Leu His Cys Thr Gly His Ile His Val Tyr Asp Thr
        190                 195                 200 aac agt aac caa cct cag tgt ggg tac aag aaa cca ccc atg acg tgc    914
Asn Ser Asn Gln Pro Gln Cys Gly Tyr Lys Lys Pro Pro Met Thr Cys
205                 210                 215 ttg gtg ctg att tgt gaa ccc att cct cat ccg tca aat att gaa att    962
Leu Val Leu Ile Cys Glu Pro Ile Pro His Pro Ser Asn Ile Glu Ile
220                 225                 230                 235 cct tta gat agc aag aca ttt ctc agt cga cac agc ctc gat atg aaa   1010
Pro Leu Asp Ser Lys Thr Phe Leu Ser Arg His Ser Leu Asp Met Lys
                240                 245                 250 ttt tct tac tgt gat gaa aga att act gag ttg atg ggt tat gag ccg   1058
Phe Ser Tyr Cys Asp Glu Arg Ile Thr Glu Leu Met Gly Tyr Glu Pro
            255                 260                 265 gaa gaa ctt ttg ggc cgc tca att tat gaa tat tat cat gct ttg gat   1106
Glu Glu Leu Leu Gly Arg Ser Ile Tyr Glu Tyr Tyr His Ala Leu Asp
        270                 275                 280 tct gat cat ctg acc aaa act cac cat gat atg ttt act aaa gga caa   1154
Ser Asp His Leu Thr Lys Thr His His Asp Met Phe Thr Lys Gly Gln
285                 290                 295 gtc acc aca gga cag tac agg atg ctt gcc aaa aga ggt gga tat gtc   1202
Val Thr Thr Gly Gln Tyr Arg Met Leu Ala Lys Arg Gly Gly Tyr Val
300                 305                 310                 315 tgg gtt gaa act caa gca act gtc ata tat aat acg aag aac tcc cag   1250
Trp Val Glu Thr Gln Ala Thr Val Ile Tyr Asn Thr Lys Asn Ser Gln
                320                 325                 330 cca cag tgc att gtg tgt gtg aat tat gtt gta agt ggt att att cag   1298
Pro Gln Cys Ile Val Cys Val Asn Tyr Val Val Ser Gly Ile Ile Gln
            335                 340                 345 cac gac ttg att ttc tcc ctt caa caa aca gaa tct gtg ctc aaa cca   1346
His Asp Leu Ile Phe Ser Leu Gln Gln Thr Glu Ser Val Leu Lys Pro
        350                 355                 360 gtt gaa tct tca gat atg aag atg act cag ctg ttc acc aaa gtt gaa   1394
Val Glu Ser Ser Asp Met Lys Met Thr Gln Leu Phe Thr Lys Val Glu
365                 370                 375
```

```
tca gag gat aca agc tgc ctt ttt gat aag ctt aag aag gag cct gat      1442
Ser Glu Asp Thr Ser Cys Leu Phe Asp Lys Leu Lys Lys Glu Pro Asp
380                 385                 390                 395 gct ctc act ctg ctg gct cca gct gcc ggc gac acc atc atc tct ctg      1490
Ala Leu Thr Leu Leu Ala Pro Ala Ala Gly Asp Thr Ile Ile Ser Leu
                400                 405                 410 gat ttt ggc agc gat gac aca gaa act gaa gat caa caa ctt gaa gat      1538
Asp Phe Gly Ser Asp Asp Thr Glu Thr Glu Asp Gln Gln Leu Glu Asp
            415                 420                 425 gtt cca tta tat aat gat gta atg ttt ccc tct tct aat gaa aaa tta      1586
Val Pro Leu Tyr Asn Asp Val Met Phe Pro Ser Ser Asn Glu Lys Leu
        430                 435                 440 aat ata aac ctg gca atg tct cct tta cct tca tcg gaa act cca aag      1634
Asn Ile Asn Leu Ala Met Ser Pro Leu Pro Ser Ser Glu Thr Pro Lys
    445                 450                 455 cca ctt cga agt agt gct gat cct gca ctg aat caa gag gtt gca tta      1682
Pro Leu Arg Ser Ser Ala Asp Pro Ala Leu Asn Gln Glu Val Ala Leu
460                 465                 470                 475 aaa tta gaa tca agt cca gag tca ctg gga ctt tct ttt acc atg ccc      1730
Lys Leu Glu Ser Ser Pro Glu Ser Leu Gly Leu Ser Phe Thr Met Pro
                480                 485                 490 cag att caa gat cag cca gca agt cct tct gat gga agc act aga caa      1778
Gln Ile Gln Asp Gln Pro Ala Ser Pro Ser Asp Gly Ser Thr Arg Gln
            495                 500                 505 agt tca cct gag aga ctt ctt cag gaa aac gta aac act cct aac ttt      1826
Ser Ser Pro Glu Arg Leu Leu Gln Glu Asn Val Asn Thr Pro Asn Phe
        510                 515                 520 tcc cag cct aac agt ccc agt gaa tat tgc ttt gat gtg gat agc gat      1874
Ser Gln Pro Asn Ser Pro Ser Glu Tyr Cys Phe Asp Val Asp Ser Asp
    525                 530                 535 atg gtc aat gta ttc aag ttg gaa ctg gtg gaa aaa ctg ttt gct gaa      1922
Met Val Asn Val Phe Lys Leu Glu Leu Val Glu Lys Leu Phe Ala Glu
540                 545                 550                 555 gac aca gag gca aag aat cca ttt tca act cag gac act gat tta gat      1970
Asp Thr Glu Ala Lys Asn Pro Phe Ser Thr Gln Asp Thr Asp Leu Asp
                560                 565                 570 ttg gag atg ctg gct ccc tat atc cca atg gat gat gat ttc cag tta      2018
Leu Glu Met Leu Ala Pro Tyr Ile Pro Met Asp Asp Asp Phe Gln Leu
            575                 580                 585 cgt tcc ttt gat cag ttg tca cca tta gag agc aat tct cca agc cct      2066
Arg Ser Phe Asp Gln Leu Ser Pro Leu Glu Ser Asn Ser Pro Ser Pro
        590                 595                 600 cca agt atg agc aca gtt act ggg ttc cag cag acc cag tta cag aaa      2114
Pro Ser Met Ser Thr Val Thr Gly Phe Gln Gln Thr Gln Leu Gln Lys
    605                 610                 615 cct acc atc act gcc act gcc acc aca act gcc acc act gat gaa tca      2162
Pro Thr Ile Thr Ala Thr Ala Thr Thr Thr Ala Thr Thr Asp Glu Ser
620                 625                 630                 635 aaa aca gag acg aag gac aat aaa gaa gat att aaa ata ctg att gca      2210
Lys Thr Glu Thr Lys Asp Asn Lys Glu Asp Ile Lys Ile Leu Ile Ala
                640                 645                 650 tct cca tct tct acc caa gta cct caa gaa acg acc act gct aag gca      2258
Ser Pro Ser Ser Thr Gln Val Pro Gln Glu Thr Thr Thr Ala Lys Ala
            655                 660                 665 tca gca tac agt ggc act cac agt cgg aca gcc tca cca gac aga gca      2306
Ser Ala Tyr Ser Gly Thr His Ser Arg Thr Ala Ser Pro Asp Arg Ala
        670                 675                 680 gga aag aga gtc ata gaa cag aca gac aaa gct cat cca agg agc ctt      2354
Gly Lys Arg Val Ile Glu Gln Thr Asp Lys Ala His Pro Arg Ser Leu
    685                 690                 695
```

| | | | | | | | | | | | | | | | |
|---|---|---|---|---|---|---|---|---|---|---|---|---|---|---|---|
| aag | ctg | tct | gcc | act | ttg | aat | caa | aga | aat | act | gtt | cct | gag | gaa | gaa | 2402 |
| Lys | Leu | Ser | Ala | Thr | Leu | Asn | Gln | Arg | Asn | Thr | Val | Pro | Glu | Glu | Glu |
| 700 | | | | | 705 | | | | | 710 | | | | | 715 |

```
aag ctg tct gcc act ttg aat caa aga aat act gtt cct gag gaa gaa    2402
Lys Leu Ser Ala Thr Leu Asn Gln Arg Asn Thr Val Pro Glu Glu Glu
700             705                 710                 715 tta aac cca aag aca ata gct tcg cag aat gct cag agg aag cga aaa    2450
Leu Asn Pro Lys Thr Ile Ala Ser Gln Asn Ala Gln Arg Lys Arg Lys
            720                 725                 730 atg gaa cat gat ggc tcc ctt ttt caa gca gca gga att gga aca tta    2498
Met Glu His Asp Gly Ser Leu Phe Gln Ala Ala Gly Ile Gly Thr Leu
                735                 740                 745 ttg cag caa cca ggt gac tgt gca cct act atg tca ctt tcc tgg aaa    2546
Leu Gln Gln Pro Gly Asp Cys Ala Pro Thr Met Ser Leu Ser Trp Lys
        750                 755                 760 cga gtg aaa gga ttc ata tct agt gaa cag aat gga acg gag caa aag    2594
Arg Val Lys Gly Phe Ile Ser Ser Glu Gln Asn Gly Thr Glu Gln Lys
765                 770                 775 act att att tta ata ccc tcc gat tta gca tgc aga ctg ctg ggg cag    2642
Thr Ile Ile Leu Ile Pro Ser Asp Leu Ala Cys Arg Leu Leu Gly Gln
780                 785                 790                 795 tca atg gat gag agt gga tta cca cag ctg acc agt tac gat tgt gaa    2690
Ser Met Asp Glu Ser Gly Leu Pro Gln Leu Thr Ser Tyr Asp Cys Glu
            800                 805                 810 gtt aat gct ccc ata caa ggc agc aga aac cta ctg cag ggt gaa gaa    2738
Val Asn Ala Pro Ile Gln Gly Ser Arg Asn Leu Leu Gln Gly Glu Glu
                815                 820                 825 tta ctc aga gct ttg gat caa gtt aac tga gcgtttccta atctcattcc      2788
Leu Leu Arg Ala Leu Asp Gln Val Asn *
        830                 835
```
ttttgattgt taatgttttt gttcagttgt tgttgtttgt tgggttttg tttctgttgg    2848 ttattttgg acactggtgg ctcagcagtc tatttatatt ttctatatct aattttagaa    2908
gcctggctac aatactgcac aaactcagat agtttagttt tcatcccctt tctacttaat    2968
tttcattaat gctcttttta atatgttctt ttaatgccag atcacagcac attcacagct    3028
cctcagcatt tcaccattgc attgctgtag tgtcatttaa aatgcacctt tttatttatt    3088 tattttggt gagggagttt gtcccttatt gaattatttt taatgaaatg ccaatataat    3148
tttttaagaa agcagtaaat tctcatcatg atcataggca gttgaaaact ttttactcat    3208
ttttttcatg ttttacatga aaataatgct ttgtcagcag tacatggtag ccacaattgc    3268
acaatatatt ttctttaaaa aaccagcagt tactcatgca atatattctg catttataaa    3328
actagttttt aagaaatttt ttttggccta tggaattgtt aagcctggat catgaagcgt    3388
tgatcttata atgattctta aactgtatgg tttctttata tgggtaaagc catttacatg    3448
atataaagaa atatgcttat atctggaagg tatgtggcat ttatttggat aaaattctca    3508
attcagagaa gttatctggt gtttcttgac tttaccaact caaaacagtc cctctgtagt    3568
tgtggaagct tatgctaata ttgtgtaatt gattatgaaa cataaatgtt ctgcccaccc    3628
tgttggtata aagacatttt gagcatactg taaacaaaca aacaaaaaat catgctttgt    3688
tagtaaaatt gcctagtatg ttgatttgtt gaaaatatga tgtttggttt tatgcacttt    3748
gtcgctatta acatccttt ttcatataga tttcaataag tgagtaattt tagaagcatt    3808 atttaggaa tatagagttg tcatagtaaa catcttgttt tttctatgta cactgtataa    3868 attttcgtt cccttgctct ttgtggttgg gtctaacact aactgtactg ttttgttata    3928
tcaaataaac atcttctgtg gaccaggaaa aaaaaaaaa aaaaa    3973

<210> SEQ ID NO 6
<211> LENGTH: 836
<212> TYPE: PRT

<213> ORGANISM: Mus musculus

<400> SEQUENCE: 6

```
Met Glu Gly Ala Gly Gly Asn Glu Lys Lys Met Ser Ser Glu
 1               5                  10                  15

Arg Arg Lys Glu Lys Ser Arg Asp Ala Ala Arg Ser Arg Arg Ser Lys
            20                  25                  30

Glu Ser Glu Val Phe Tyr Glu Leu Ala His Gln Leu Pro Leu Pro His
        35                  40                  45

Asn Val Ser Ser His Leu Asp Lys Ala Ser Val Met Arg Leu Thr Ile
    50                  55                  60

Ser Tyr Leu Arg Val Arg Lys Leu Leu Asp Ala Gly Gly Leu Asp Ser
65                  70                  75                  80

Glu Asp Glu Met Lys Ala Gln Met Asp Cys Phe Tyr Leu Lys Ala Leu
                85                  90                  95

Asp Gly Phe Val Met Val Leu Thr Asp Asp Gly Asp Met Val Tyr Ile
            100                 105                 110

Ser Asp Asn Val Asn Lys Tyr Met Gly Leu Thr Gln Phe Glu Leu Thr
        115                 120                 125

Gly His Ser Val Phe Asp Phe Thr His Pro Cys Asp His Glu Glu Met
    130                 135                 140

Arg Glu Met Leu Thr His Arg Asn Gly Pro Val Arg Lys Gly Lys Glu
145                 150                 155                 160

Leu Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
            180                 185                 190

His Cys Thr Gly His Ile His Val Tyr Asp Thr Asn Ser Asn Gln Pro
        195                 200                 205

Gln Cys Gly Tyr Lys Lys Pro Pro Met Thr Cys Leu Val Leu Ile Cys
    210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Glu Leu Leu Gly
            260                 265                 270

Arg Ser Ile Tyr Glu Tyr Tyr His Ala Leu Asp Ser Asp His Leu Thr
        275                 280                 285

Lys Thr His His Asp Met Phe Thr Lys Gly Gln Val Thr Thr Gly Gln
    290                 295                 300

Tyr Arg Met Leu Ala Lys Arg Gly Gly Tyr Val Trp Val Glu Thr Gln
305                 310                 315                 320

Ala Thr Val Ile Tyr Asn Thr Lys Asn Ser Gln Pro Gln Cys Ile Val
                325                 330                 335

Cys Val Asn Tyr Val Val Ser Gly Ile Ile Gln His Asp Leu Ile Phe
            340                 345                 350

Ser Leu Gln Gln Thr Glu Ser Val Leu Lys Pro Val Glu Ser Ser Asp
        355                 360                 365

Met Lys Met Thr Gln Leu Phe Thr Lys Val Glu Ser Glu Asp Thr Ser
    370                 375                 380

Cys Leu Phe Asp Lys Leu Lys Lys Glu Pro Asp Ala Leu Thr Leu Leu
385                 390                 395                 400

Ala Pro Ala Ala Gly Asp Thr Ile Ile Ser Leu Asp Phe Gly Ser Asp
```

```
                    405                 410                 415
Asp Thr Glu Thr Glu Asp Gln Gln Leu Glu Asp Val Pro Leu Tyr Asn
                420                 425                 430

Asp Val Met Phe Pro Ser Ser Asn Glu Lys Leu Asn Ile Asn Leu Ala
            435                 440                 445

Met Ser Pro Leu Pro Ser Ser Glu Thr Pro Lys Pro Leu Arg Ser Ser
        450                 455                 460

Ala Asp Pro Ala Leu Asn Gln Glu Val Ala Leu Lys Leu Glu Ser Ser
465                 470                 475                 480

Pro Glu Ser Leu Gly Leu Ser Phe Thr Met Pro Gln Ile Gln Asp Gln
                485                 490                 495

Pro Ala Ser Pro Ser Asp Gly Ser Thr Arg Gln Ser Ser Pro Glu Arg
            500                 505                 510

Leu Leu Gln Glu Asn Val Asn Thr Pro Asn Phe Ser Gln Pro Asn Ser
        515                 520                 525

Pro Ser Glu Tyr Cys Phe Asp Val Asp Ser Asp Met Val Asn Val Phe
    530                 535                 540

Lys Leu Glu Leu Val Glu Lys Leu Phe Ala Glu Asp Thr Glu Ala Lys
545                 550                 555                 560

Asn Pro Phe Ser Thr Gln Asp Thr Asp Leu Asp Leu Glu Met Leu Ala
                565                 570                 575

Pro Tyr Ile Pro Met Asp Asp Asp Phe Gln Leu Arg Ser Phe Asp Gln
            580                 585                 590

Leu Ser Pro Leu Glu Ser Asn Ser Pro Ser Pro Pro Ser Met Ser Thr
        595                 600                 605

Val Thr Gly Phe Gln Gln Thr Gln Leu Gln Lys Pro Thr Ile Thr Ala
    610                 615                 620

Thr Ala Thr Thr Thr Ala Thr Asp Glu Ser Lys Thr Glu Thr Lys
625                 630                 635                 640

Asp Asn Lys Glu Asp Ile Lys Ile Leu Ile Ala Ser Pro Ser Ser Thr
                645                 650                 655

Gln Val Pro Gln Glu Thr Thr Thr Ala Lys Ala Ser Ala Tyr Ser Gly
            660                 665                 670

Thr His Ser Arg Thr Ala Ser Pro Asp Arg Ala Gly Lys Arg Val Ile
        675                 680                 685

Glu Gln Thr Asp Lys Ala His Pro Arg Ser Leu Lys Leu Ser Ala Thr
    690                 695                 700

Leu Asn Gln Arg Asn Thr Val Pro Glu Glu Leu Asn Pro Lys Thr
705                 710                 715                 720

Ile Ala Ser Gln Asn Ala Gln Arg Lys Arg Lys Met Glu His Asp Gly
                725                 730                 735

Ser Leu Phe Gln Ala Ala Gly Ile Gly Thr Leu Leu Gln Gln Pro Gly
            740                 745                 750

Asp Cys Ala Pro Thr Met Ser Leu Ser Trp Lys Arg Val Lys Gly Phe
        755                 760                 765

Ile Ser Ser Glu Gln Asn Gly Thr Glu Gln Lys Thr Ile Ile Leu Ile
    770                 775                 780

Pro Ser Asp Leu Ala Cys Arg Leu Leu Gly Gln Ser Met Asp Glu Ser
785                 790                 795                 800

Gly Leu Pro Gln Leu Thr Ser Tyr Asp Cys Glu Val Asn Ala Pro Ile
                805                 810                 815

Gln Gly Ser Arg Asn Leu Leu Gln Gly Glu Glu Leu Leu Arg Ala Leu
            820                 825                 830
```

Asp Gln Val Asn
      835

<210> SEQ ID NO 7
<211> LENGTH: 2559
<212> TYPE: DNA
<213> ORGANISM: Mus musculus

<400> SEQUENCE: 7

| | | | | | |
|---|---|---|---|---|---|
| tgcaccgtga | ccagaagagc | cgcacgctct | tgcaccacgc | ggtcagcact | ggcagtaagg | 60 |
| aagtggtccg | ctatctgctg | gatcatggta | agctgcgttg | ctggggctgg | gagggagaaa | 120 |
| gggggagcca | ggctcttagc | atccccttc | cttttatctg | cagcacctcc | agagatcctt | 180 |
| gatgctgtgg | aggagaagtg | agtatctgag | acacaggccc | ctggttcacc | agaaaaccac | 240 |
| cttccttcag | gtctaaccat | ttggtcaccc | agagcccaag | aaccctttgt | ggctagcact | 300 |
| gagcacccct | ccccctcttg | ccaaactcct | gcccttcta | atggctgttg | ggagactgct | 360 |
| gggcaggcct | agagaactgc | aagtgtctac | aaccagcccc | tgttcccag | tggggagacc | 420 |
| tgtctacacc | aggcagccgc | cctgggtcag | cgcaccatct | gccactacat | tgtggaagcc | 480 |
| ggggcctcct | catgaagaca | gatctgcagg | tgagttgcct | ggcagagcac | aaactcaccc | 540 |
| tttcccagac | ttgggggcag | ggctagggaa | tttcaagctc | ttctgagcca | acacagtcca | 600 |
| ggccctgaga | aacctgagcc | agcaggggga | aagcttgtga | cctctgagga | taccctcccc | 660 |
| ctctggctcc | gtagaagaac | ccctgcccctt | tcctaaggcc | ttgggggccc | ttccaccctt | 720 |
| ttccagggcg | acactccccg | gcagcgcgct | gtgaaggctc | aagacacaga | gctcgctgcc | 780 |
| tacctggaga | acagacagca | ttaccagatg | atccagcgtg | aggaccagga | gacagctgtg | 840 |
| tagttaaggg | gaccatggat | caacaaggga | cactaccaga | ggactctcct | tgcccatctc | 900 |
| actgccacat | tcctgtcaga | tggctatggg | gggaccctgc | cacagggaag | gagccccgtg | 960 |
| ccaccccctg | agaagctgtt | cagatctagg | gctggactct | aaggagctgg | actctcacct | 1020 |
| gtccctggtt | tcatggggaa | caggaaacag | gctgggctgg | ctggttccct | cccttcaggg | 1080 |
| cagcctccag | ctcaccacag | cagatggaag | ggctggacag | agctcagcat | cgatgtcagg | 1140 |
| gaggcctgca | ctcagcagga | cttttcaaaag | ccacctgatc | ctttgggctc | tctggagggt | 1200 |
| cctgggtacc | taaccctcct | ctctgatcca | cccaccctgg | gcatcccaga | aactcaagag | 1260 |
| cctgctgtat | tcacttgccc | gctgccctgc | ttggcaccta | ccctggtctt | cctcctcatg | 1320 |
| tatccagcca | tttcatttcg | gactgtatgg | cctggggtgg | ggggtgggc | tcccacggtg | 1380 |
| acttgtttac | agctgggtgt | gactcagtaa | agtgaatttt | ttttccttc | ttgttttctt | 1440 |
| tttttcttgt | tgtgggggac | tcacatgagc | aatggtgtgt | gctgggtaat | ccttgggtc | 1500 |
| ggggaaatgg | ccaccaacat | ctcagatcac | ttcgggagat | gggtctgccc | cgatcctgac | 1560 |
| ctctgcctag | ggccttaggc | tcacagcgcc | tggggcggag | ctgattttcc | ccgcttcccg | 1620 |
| ctcctgcagg | gatgataaca | atgaaagtaa | aagaggtggg | gcggggccca | ggcttgggtt | 1680 |
| ctttggtctt | ttggccctgt | gccctggagc | agtcccctcc | ccctggcttg | tactgggggg | 1740 |
| gggggatct | gcttgaggtg | agcctgaggc | cccagggtca | ggggtgggcg | gttatcacct | 1800 |
| ccggggaag | cccggtctgg | aacttctcag | acagctcttg | tcagcgacaa | gatttaccaa | 1860 |
| actcatttct | atgtgcttcc | ccatcccccc | ccaacgcccc | tccctcctcc | tcctccccca | 1920 |
| aacctgcact | agaaaaaggc | tctcgagcct | tgctcacccg | gagccatctg | aggtcccagg | 1980 |
| tacccagctc | cctgccacat | cagagaccct | tcttgcactc | tgagtgaact | gattaaaaaa | 2040 |
| aaaaaaaaaa | accaagccgg | aggtgagccg | ggcctcgaag | ggaaggttcg | cgggtgcggt | 2100 |

```
ggccgccccg agcctgtgac accaggacat actcccgggg cccgcggtgg gcaagcgaag      2160
tggtgacctg agagctgaca ggctgcgaga gggaaaagta tagacaggcc tagaccaggg      2220 gaagggagg ggatagagag ctgggcctgc tacgagggga cctgagccag aagcgcactg       2280
gtaaaaccga actccaggac cagagaccca gagatcagag gtgagaggca cagacgcggg      2340
agtcccggct cggcgagggg cgggagtgga ggcggggact agggggggtct ggggaggtgc     2400 gggtttgggg ggaggggggcg ggtccttcca cgggatgggg ggagggggcgg ggggcccatgt  2460 gaccggctca gaccggttct ggagacaaaa gggccttag cggccttagc gggacaggcc      2520
ggagcgggag ggagcgaagc atcgagcagt gagcgagtg                             2559

<210> SEQ ID NO 8
<211> LENGTH: 2074
<212> TYPE: DNA
<213> ORGANISM: Mus musculus

<400> SEQUENCE: 8
tcatgaagac agatctgcag gtgagttgcc tggcagagca caaactcacc ctttcccaga        60 cttggggggca gggctaggga atttcaagct cttctgagcc aacacagtcc aggccctgag      120
aaacctgagc cagcaggggg aaagcttgtg acctctgagg ataccctccc cctctggctc       180
cgtagaagaa cccctgccct ttcctaaggc cttgggggcc cttccaccct tttcagggc        240 gacactcccc ggcagcgcgc tgagaaggct caagacacag agctcgctgc ctacctggag       300
aacagacagc attaccagat gatccagcgt gaggaccagg agacagctgt gtagttaagg       360
ggaccatgga tcaacaaggg acactaccag aggactctcc ttgcccatct cactgccaca      420
ttcctgtcag atggctatgg ggggaccctg ccacagggaa ggagccccgt gccacccccct     480 gagaagctgt tcagatctag ggctggactc taaggagctg gactctcacc tgtccctggt      540
ttcatgggga acaggaaaca ggctgggctg gctggttccc tcccttcagg gcagcctcca     600
gctcaccaca gcagatggaa gggctggaca gagctcagca tcgatgtcag ggaggcctgc     660
actcagcagg acttcaaaa gccacctgat cctttgggct ctctggaggg ttctgggtac      720
ctaacccctc tctctgatcc acccaccctg ggcatcccag aaactcaaga gcctgctgta     780
ttcacttgcc cgctgccctg cttggcacct accctggtct tcctcctcat gtatccagcc    840
atttcatttc ggactgtatg gcctgggggtg ggggggtggg ctcccacggt gacttgttta    900
cagctgggtg tgactcagta aagtgaattt ttttttcctt cttgtttttct tttttttcttg   960 ttgtggggga ctcacatgag caatggtgtg tgctgggtaa tccttgggggt cggggaaatg     1020 gccaccaaca tctcagatca cttcgggaga tgggtctgcc ccgatcctga cctctgccta     1080
gggccttagg ctcacagcgc ctggggcgga gctgattttc cccgcttccc gctcctgcag     1140
ggatgataac aatgaaagta aaagaggtgg ggcgggggcc aggcttgggt tctttggtct     1200
tttggccctg tgcctggag cagtccctc ccctggctt gtactgggg gggggggat          1260 ctgcttgagg tgagcctgag gccccagggt caggggtggg cggttatcac ctccggggga    1320
agcccggtct ggaacttctc agacagctct tgtcagcgac aagatttacc aaactcattt    1380
ctatgtgctt ccccatcccc ccccaacgcc cttccctcct cctcctcccc caaacctgca     1440
ctagaaaaag gctctcgagc cttgctcacc cggagccatc tgaggtccca ggtacccagc    1500
tccctgccac atcagagacc cttcttgcac tctgagtgaa ctgattaaaa aaaaaaaaa      1560 aaaaaaccaa gccggaggtg agccgggcct cgaaggggaag gttcgcgggt gcggtggccg    1620
ccccgagcct gtgacaccag gacatactcc cgggggcccgc ggtgggcaag cgaagtggtg    1680
```

```
acctgagagc tgacaggctg cgagagggaa aagtatagac aggcctagac caggggaagg    1740
ggagggata gagagctggg cctgctacga ggggacctga gccagaagcg cactggtaaa    1800
accgaactcc aggaccagag acccagagat cagaggtgag aggcacagac gcgggagtcc    1860
cggctcggcg aggggcggga gtggaggcgg ggactagggg ggtctgggga ggtgcgggtt    1920
tgggggagg gggcgggtcc ttccacggga tgggggagg ggcgggggcc catgtgaccg    1980
gctcagaccg gttctggaga caaaagggc cttagcggcc ttagcgggac aggccggagc    2040
gggagggagc gaagcatcga gcagtgagcg agtg                                2074
```

<210> SEQ ID NO 9
<211> LENGTH: 1677
<212> TYPE: DNA
<213> ORGANISM: Mus musculus

<400> SEQUENCE: 9

```
tccttgccca tctcactgcc acattcctgt cagatggcta tgggggggacc ctgccacagg    60
gaaggagccc cgtgccaccc cctgagaagc tgttcagatc tagggctgga ctctaaggag   120
ctggactctc acctgtccct ggtttcatgg ggaacaggaa acaggctggg ctggctggtt   180
ccctcccttc agggcagcct ccagctcacc acagcagatg aagggctgga cagagctca   240
gcatcgatgt cagggaggcc tgcactcagc aggactttca aaagccacct gatcctttgg   300
gctctctgga gggttctggg tacctaaccc tcctctctga tccacccacc ctgggcatcc   360
cagaaactca gagcctgct gtattcactt gcccgctgcc ctgcttggca cctaccctgg   420
tcttcctcct catgtatcca gccatttcat tcggactgt atggcctggg gtgggggtg   480
gggctcccac ggtgacttgt ttacagctgg gtgtgactca gtaaagtgaa ttttttttcc   540
tttcttgttt tcttttttc ttgttgtggg ggactcacat gagcaatggt gtgtgctggg   600
taatccttgg ggtcggggaa atggccacca acatctcaga tcacttcggg agatgggtct   660
gccccgatcc tgacctctgc ctagggcctt aggctcacag cgcctggggc ggagctgatt   720
ttccccgctt cccgctcctg cagggatgat aacaatgaaa gtaaaagagg tggggcgggg   780
gccaggcttg ggttctttgg tcttttggcc ctgtgccctg gagcagtccc ctcccctgg    840
cttgtactgg gggggggggg gatctgcttg aggtgagcct gaggcccag ggtcagggt    900
gggcggttat cacctccggg ggaagcccgg tctggaactt ctcagacagc tcttgtcagc   960
gacaagattt accaaactca tttctatgtg cttccccatc ccccccaac gcccttccct   1020
cctcctcctc ccccaaacct gcactagaaa aaggctctcg agccttgctc acccggagcc   1080
atctgaggtc ccaggtaccc agctccctgc cacatcagag acccttcttg cactctgagt   1140
gaactgatta aaaaaaaaaa aaaaaaaac caagccggag gtgagccggg cctcgaaggg   1200
aaggttcgcg ggtgcggtgg ccgccccgag cctgtgacac caggacatac tcccggggcc   1260
cgcggtgggc aagcgaagtg gtgacctgag agctgacagg ctgcgagagg gaaaagtata   1320
gacaggccta gaccaggga aggggagggg atagagagct gggcctgcta cgagggggacc   1380
tgagccagaa gcgcactggt aaaaccgaac tccaggacca gagacccaga gatcagaggt   1440
gagaggcaca gacgcgggag tcccggctcg gcgaggggcg ggagtggagg cggggactag   1500
gggggtctgg ggaggtgcgg gtttgggggg aggggcggg tccttccacg ggatgggggg   1560
aggggcgggg gcccatgtga ccggctcaga ccggttctgg agacaaaagg ggccttagcg   1620
gccttagcgg gacaggccgg agcgggaggg agcgaagcat cgagcagtga gcgagtg      1677
```

```
<210> SEQ ID NO 10
<211> LENGTH: 1037
<212> TYPE: DNA
<213> ORGANISM: Mus musculus

<400> SEQUENCE: 10
tcacttcggg agatgggtct gccccgatcc tgacctctgc ctagggcctt aggctcacag      60
cgcctggggc ggagctgatt ttccccgctt cccgctcctg cagggatgat aacaatgaaa     120
gtaaaagagg tggggcgggg gccaggcttg ggttctttgg tcttttggcc ctgtgccctg     180
gagcagtccc ctcccctgg cttgtactgg ggggggggg gatctgcttg aggtgagcct       240
gaggccccag ggtcagggt gggcggttat cacctccggg ggaagcccgg tctggaactt     300
ctcagacagc tcttgtcagc gacaagattt accaaactca tttctatgtg cttccccatc    360 ccccccaac gcccttccct cctcctcctc ccccaaacct gcactagaaa aaggctctcg      420
agccttgctc acccgagcc atctgaggtc ccaggtaccc agctccctgc cacatcagag      480
acccttcttg cactctgagt gaactgatta aaaaaaaaa aaaaaaaaac caagccggag      540
gtgagccggg cctcgaaggg aaggttcgcg ggtgcggtgg ccgccccgag cctgtgacac     600
caggacatac tcccggggcc cgcggtgggc aagcgaagtg gtgacctgag agctgacagg     660
ctgcgagagg gaaaagtata gacaggccta gaccagggga aggggagggg atagagagct    720
gggcctgcta cgaggggacc tgagccagaa gcgcactggt aaaaccgaac tccaggacca    780
gagacccaga gatcagaggt gagaggcaca gacgcgggag tcccggctcg gcgaggggcg    840
ggagtggagg cggggactag ggggtctgg ggaggtgcgg gtttgggggg aggggcgggg    900
tccttccacg ggatggggg aggggcgggg gcccatgtga ccggctcaga ccggttctgg    960
agacaaaagg ggccttagcg gccttagcgg gacaggccgg agcgggaggg agcgaagcat    1020
cgagcagtga gcgagtg                                                    1037

<210> SEQ ID NO 11
<211> LENGTH: 2559
<212> TYPE: DNA
<213> ORGANISM: Artificial Sequence
<220> FEATURE:
<223> OTHER INFORMATION: Site directed mutation of midkine promoter

<400> SEQUENCE: 11
tgcaccgtga ccagaagagc cgcacgctct tgcaccacgc ggtcagcact ggcagtaagg     60
aagtggtccg ctatctgctg gatcatggta agctgcgttg ctgggctgg gagggagaaa     120 gggggagcca ggctcttagc atcccctttc cttttatctg cagcacctcc agagatcctt    180
gatgctgtgg aggagaagtg agtatctgag acacaggccc ctggttcacc agaaaaccac    240
cttccttcag gtctaaccat tggtcaccc agagcccaag aaccctttgt ggctagcact    300 gagcacccctt cccctcttg ccaaactcct gcccttccta atggctgttg ggagactgct    360
gggcaggcct agagaactgc aagtgtctac aaccagcccc tgttcccag tggggagacc    420 tgtctacacc aggcagccgc cctggtcag cgcaccatct gccactacat tgtggaagcc    480
ggggcctcct catgaagaca gatctgcagg tgagttgcct ggcagagcac aaactcaccc    540
tttcccagac ttgggggcag ggctaggaa tttcaagctc ttctgagcca acacagtcca    600
ggccctgaga aacctgagcc agcaggggga aagcttgtga cctctgagga taccctcccc    660
ctctggctcc gtagaagaac ccctgcccctt tcctaaggcc ttggggggccc ttccacccctt   720 ttccagggcg acactccccg gcagcgcgct gtgaaggctc aagacacaga gctcgctgcc    780
tacctggaga acagacagca ttaccagatg atccagcgtg aggaccagga gacagctgtg    840
```

```
tagttaaggg gaccatggat caacaaggga cactaccaga ggactctcct tgcccatctc    900
actgccacat tcctgtcaga tggctatggg gggaccctgc cacagggaag gagccccgtg    960
ccacccctg  agaagctgtt cagatctagg gctggactct aaggagctgg actctcacct   1020
gtccctggtt tcatggggaa caggaaacag gctgggctgg ctggttccct cccttcaggg   1080
cagcctccag ctcaccacag cagatggaag ggctggacag agctcagcat cgatgtcagg   1140
gaggcctgca ctcagcagga cttcaaaag ccacctgatc ctttgggctc tctggagggt    1200
cctgggtacc taaccctcct ctctgatcca cccaccctgg gcatcccaga aactcaagag   1260
cctgctgtat tcacttgccc gctgccctgc ttggcaccta ccctggtctt cctcctcatg   1320
tatccagcca tttcatttcg gactgtatgg cctggggtgg ggggtggggc tcccacggtg   1380
acttgtttac agctgggtgt gactcagtaa agtgaatttt ttttcctttc ttgttttctt   1440
tttttcttgt tgtgggggac tcacatgagc aatggtgtgt gctgggtaat ccttggggtc   1500
gggggaaatgg ccaccaacat ctcagatcac ttcgggagat gggtctgccc cgatcctgac   1560
ctctgcctag ggccttaggc tcacagcgcc tggggcggag ctgattttcc ccgcttcccg   1620
ctcctgcagg gatgataaca atgaaagtaa aagaggtggg gcgggggcca ggcttgggtt   1680
ctttggtctt ttggccctgt gccctggagc agtccctcc  ccctggcttg tactgggggg   1740
gggggatct  gcttgaggtg agcctgaggc cccaggtca ggggtgggcg gttatcacct    1800
ccggggaag  cccggtctgg aacttctcag acagctcttg tcagcgacaa gatttaccaa   1860
actcatttct atgtgcttcc ccatccccc  ccaacgccct tccctcctcc tcctccccca   1920
aacctgcact agaaaaaggc tctcgagcct tgctcacccg gagccatctg aggtcccagg   1980
tacccagctc cctgccacat cagagaccct tcttgcactc tgagtgaact gattaaaaaa   2040
aaaaaaaaaa accaagccgg aggtgagccg ggcctcgaag ggaaggttcg cgggtgcggt   2100
ggccgccccg agcctgtgac accaggacat actcccgggg cccgcggtgg gccccccgaag  2160
tggtgacctg agagctgaca ggctgcgaga gggaaaagta tagacaggcc tagaccaggg   2220
gaaggggagg ggatagagag ctgggcctgc tacgagggga cctgagccag aagcgcactg   2280
gtaaaaccga actccaggac cagagaccca gagatcagag gtgagaggca cagacgcggg   2340
agtcccggct cggcgagggg cgggagtgga ggcgggact  aggggggtct ggggaggtgc   2400
gggtttgggg ggaggggcg  ggtccttcca cgggatgggg ggaggggcgg gggcccatgt   2460
gaccggctca gaccggttct ggagacaaaa gggggcttag cggccttagc gggacaggcc   2520
ggagcgggag ggagcgaagc atcgagcagt gagcgagtg                          2559
```

<210> SEQ ID NO 12
<211> LENGTH: 2559
<212> TYPE: DNA
<213> ORGANISM: Artificial Sequence
<220> FEATURE:
<223> OTHER INFORMATION: Site directed mutation of midkine promoter

<400> SEQUENCE: 12

```
tgcaccgtga ccagaagagc cgcacgctct tgcaccacgc ggtcagcact ggcagtaagg     60
aagtggtccg ctatctgctg gatcatggta agctgcgttg ctggggctgg gagggagaaa    120
gggggagcca ggctcttagc atcccctttc ctttatctg  cagcacctcc agagatcctt    180
gatgctgtgg aggagaagtg agtatctgag acacaggccc ctggttcacc agaaaaccac    240
cttccttcag gtctaaccat ttggtcaccc agagcccaag aacccttgt  ggctagcact    300
gagcaccctt cccctcttg  ccaaactcct gcccttcta  atggctgttg ggagactgct    360
```

```
gggcaggcct agagaactgc aagtgtctac aaccagcccc tgttcccag tggggagacc      420 tgtctacacc aggcagccgc cctgggtcag cgcaccatct gccactacat tgtggaagcc      480
ggggcctcct catgaagaca gatctgcagg tgagttgcct ggcagagcac aaactcaccc      540
tttcccagac ttgggggcag ggctagggaa tttcaagctc ttctgagcca acacagtcca      600
ggccctgaga aacctgagcc agcaggggaa aagcttgtga cctctgagga tacctcccc      660 ctctggctcc gtagaagaac ccctgccctt tcctaaggcc ttgggggccc ttccacccct      720
ttccagggcg acactccccg gcagcgcgct gtgaaggctc aagacacaga gctcgctgcc      780
tacctggaga acagacagca ttaccagatg atccagcgtg aggaccagga gacagctgtg      840
tagttaaggg gaccatggat caacaaggga cactaccaga ggactctcct tgcccatctc      900
actgccacat tcctgtcaga tggctatggg ggaccctgc cacagggaag gagccccgtg      960
ccaccccctg agaagctgtt cagatctagg gctggactct aaggagctgg actctcacct     1020
gtccctggtt tcatggggaa caggaaacag gctgggctgg ctggttccct cccttcaggg     1080
cagcctccag ctcaccacag cagatggaag ggctggacag agctcagcat cgatgtcagg     1140
gaggcctgca ctcagcagga cttcaaaag ccacctgatc ctttgggctc tctggagggt     1200
cctgggtacc taaccctcct ctctgatcca cccaccctgg gcatcccaga aactcaagag     1260
cctgctgtat tcacttgccc gctgccctgc ttggcaccta ccctggtctt cctcctcatg     1320
tatccagcca tttcatttcg gactgtatgg cctggggtgg ggggtggggc tcccacggtg     1380
acttgtttac agctgggtgt gactcagtaa agtgaatttt ttttcctttc ttgttttctt     1440
tttttcttgt tgtgggggac tcacatgagc aatggtgtgt gctgggtaat ccttggggtc     1500
ggggaaatgg ccaccaacat ctcagatcac ttcgggagat gggtctgccc cgatcctgac     1560
ctctgcctag ggccttaggc tcacagcgcc tggggcggag ctgattttcc ccgcttcccg     1620
ctcctgcagg gatgataaca atgaaagtaa aagaggtggg gcggggggcca ggcttgggtt     1680 ctttggtctt ttggccctgt gccctggagc agtcccctcc ccctggcttg tactgggggg     1740 gggggggatct gcttgaggtg agcctgaggc cccagggtca ggggtgggcg gttatcacct     1800
ccgggggaag cccggtctgg aacttctcag acagctcttg tcagcgacaa gatttaccaa     1860
actcatttct atgtgcttcc ccatccccc caacgccct tccctcctcc tctccccca      1920 aacctgcact agaaaaaggc tctcgagcct tgctcacccg gagccatctg aggtcccagg     1980
tacccagctc cctgccacat cagagaccct tcttgcactc tgagtgaact gattaaaaaa     2040
aaaaaaaaaa acccccccgg aggtgagccg ggcctcgaag ggaaggttcg cgggtgcggt     2100
ggccgccccg agcctgtgac accaggacat actcccgggg cccgcggtgg caagcgaag      2160 tggtgacctg agagctgaca ggctgcgaga gggaaaagta tagacaggcc tagaccaggg     2220 gaagggagg ggatagagag ctgggcctgc tacgagggga cctgagccag aagcgcactg      2280
gtaaaaccga actccaggac cagagaccca gagatcagag gtgagaggca cagacgcggg     2340
agtcccggct cggcgagggg cgggagtgga ggcggggact agggggggtct ggggaggtgc    2400 gggtttgggg ggagggggcg ggtccttcca cgggatgggg ggaggggcgg gggcccatgt     2460
gaccggctca gaccggttct ggagacaaaa ggggccttag cggccttagc gggacaggcc     2520
ggagcgggag ggagcgaagc atcgagcagt gagcgagtg                            2559
```

<210> SEQ ID NO 13
<211> LENGTH: 2559
<212> TYPE: DNA
<213> ORGANISM: Artificial Sequence
<220> FEATURE:
<223> OTHER INFORMATION: Site directed mutation of midkine promoter

<400> SEQUENCE: 13

```
tgcaccgtga ccagaagagc cgcacgctct tgcaccacgc ggtcagcact ggcagtaagg      60
aagtggtccg ctatctgctg gatcatggta agctgcgttg ctggggctgg gagggagaaa     120
gggggagcca ggctcttagc atcccctttc cttttatctg cagcacctcc agagatcctt     180
gatgctgtgg aggagaagtg agtatctgag acacaggccc ctggttcacc agaaaaccac     240
cttccttcag gtctaaccat ttggtcaccc agagcccaag aacccttttgt ggctagcact    300
gagcacccct cccctcttg ccaaactcct gcccttttcta atggctgttg ggagactgct     360
gggcaggcct agagaactgc aagtgtctac aaccagcccc tgttcccag tggggagacc      420
tgtctacacc aggcagccgc cctgggtcag cgcaccatct gccactacat tgtggaagcc     480
ggggcctcct catgaagaca gatctgcagg tgagttgcct ggcagagcac aaactcaccc     540
tttcccagac ttgggggcag ggctaggaa tttcaagctc ttctgagcca acacagtcca      600
ggccctgaga aacctgagcc agcagggga aagcttgtga cctctgagga taccctcccc      660
ctctggctcc gtagaagaac ccctgccctt cctaaggcc ttgggggccc ttccacccctt     720
ttccagggcg acactccccg gcagcgcgct gtgaaggctc aagacacaga gctcgctgcc     780
tacctggaga acagacagca ttaccagatg atccagcgtg aggaccagga dacagctgtg    840
tagttaaggg gaccatggat caacaaggga cactaccaga ggactctcct tgcccatctc     900
actgccacat tcctgtcaga tggctatggg gggaccctgc cacagggaag gagccccgtg     960
ccacccctg agaagctgtt cagatctagg gctggactct aaggagctgg actctcacct    1020
gtccctggtt tcatggggaa caggaaacag gctgggctgg ctggttccct ccccttcaggg   1080
cagcctccag ctcaccacag cagatggaag ggctggacag agctcagcat cgatgtcagg    1140
gaggcctgca ctcagcagga cttcaaaag ccacctgatc cttttgggctc tctggagggt    1200
cctgggtacc taaccctcct ctctgatcca cccaccctgg gcatcccaga aactcaagag    1260
cctgctgtat tcacttgccc gctgccctgc ttggcaccta ccctggtctt cctcctcatg    1320
tatccagcca tttcatttcg gactgtatgg cctggggtgg ggggtgggc tcccacggtg     1380
acttgtttac agctgggtgt gactcagtaa agtgaatttt tttcctttc ttgttttctt     1440
tttttcttgt tgtgggggac tcacatgagc aatggtgtgt gctgggtaat ccttggggtc    1500
ggggaaatgg ccaccaacat ctcagatcac ttcgggagat gggtctgccc cgatcctgac    1560
ctctgcctag ggccttaggc tcacagcgcc tggggcggag ctgattttcc ccgcttcccg    1620
ctcctgcagg gatgataaca atgaaagtaa aagaggtggg gcggggggcca ggcttgggtt   1680
ctttggtctt ttggccctgt gccctggagc agtcccctcc ccctggcttg tactgggggg    1740
gggggatct gcttgaggtg agcctgaggc cccagggtca ggggtgggcg gttatcacct     1800
ccgggggaag cccggtctgg aacttctcag acagctcttg tcagcgaccc catttaccaa    1860
actcatttct atgtgcttcc ccatccccc caacgccct tccctcctcc tcctccccca      1920
aacctgcact agaaaaaggc tctcgagcct tgctcacccg gagccatctg aggtcccagg    1980
tacccagctc cctgccacat cagagaccct tcttgcactc tgagtgaact gattaaaaaa    2040
aaaaaaaaaa accaagccgg aggtgagccg ggcctcgaag ggaaggttcg cgggtgcggt    2100
ggccgccccg agcctgtgac accaggacat actcccgggg cccgcggtgg gcaagcgaag    2160
tggtgacctg agagctgaca ggctgcgaga gggaaaagta tagacaggcc tagaccaggg    2220
gaaggggagg ggatagagag ctgggcctgc tacgagggga cctgagccag aagcgcactg    2280
```

```
gtaaaaccga actccaggac cagagaccca gagatcagag gtgagaggca cagacgcggg    2340
agtcccggct cggcgagggg cgggagtgga ggcggggact aggggggtct ggggaggtgc    2400
gggtttgggg ggaggggcg gtccttcca cgggatgggg ggaggggcgg gggcccatgt      2460
gaccggctca gaccggttct ggagacaaaa ggggccttag cggccttagc gggacaggcc    2520
ggagcgggag ggagcgaagc atcgagcagt gagcgagtg                           2559
```

<210> SEQ ID NO 14
<211> LENGTH: 2559
<212> TYPE: DNA
<213> ORGANISM: Artificial Sequence
<220> FEATURE:
<223> OTHER INFORMATION: Site directed mutation of midkine promoter

<400> SEQUENCE: 14

```
tgcaccgtga ccagaagagc cgcacgctct tgcaccacgc ggtcagcact ggcagtaagg     60
aagtggtccg ctatctgctg gatcatggta agctgcgttg ctggggctgg gagggagaaa    120 ggggagcca ggctcttagc atcccctttc cttttatctg cagcacctcc agagatcctt    180
gatgctgtgg aggagaagtg agtatctgag acacaggccc ctggttcacc agaaaaccac    240
cttccttcag gtctaaccat ttggtcaccc agagcccaag aacctttgt ggctagcact     300 gagcacccttt cccctcttg ccaaactcct gcccttttcta atggctgttg ggagactgct   360
gggcaggcct agagaactgc aagtgtctac aaccagcccc tgttccccag tggggagacc    420
tgtctacacc aggcagccgc cctgggtcag cgcaccatct gccactacat tgtggaagcc    480
ggggcctcct catgaagaca gatctgcagg tgagttgcct ggcagagcac aaactcaccc    540
tttcccagac ttgggggcag ggctaggaa tttcaagctc ttctgagcca acacagtcca     600
ggccctgaga aacctgagcc agcagggga aagcttgtga cctctgagga taccctcccc    660
ctctggctcc gtagaagaac ccctgccctt tcctaaggcc ttgggggccc ttccacccctt    720 ttccagggcg acactccccg gcagcgcgct gtgaaggctc aagacacaga gctcgctgcc    780
tacctggaga acagacagca ttaccagatg atccagcgtg aggaccagga gacagctgtg    840
tagttaaggg gaccatggat caacaaggga cactaccaga ggactctcct tgcccatctc    900
actgccacat tcctgtcaga tggctatggg gggaccctgc cacagggaag gagccccgtg    960
ccaccccctg agaagctgtt cagatctagg gctggactct aaggagctgg actctcacct   1020
gtccctggtt tcatggggaa caggaaacag gctgggctgg ctggttccct ccccttcaggg   1080 cagcctccag ctcaccacag cagatggaag ggctggacag agctcagcat cgatgtcagg   1140
gaggcctgca ctcagcagga cttcaaaag ccacctgatc cttgggctc tctggagggt    1200 cctgggtacc taaccctcct ctctgatcca cccaccctgg gcatcccaga aactccccag   1260
cctgctgtat tcacttgccc gctgccctgc ttggcaccta ccctggtctt cctcctcatg    1320
tatccagcca tttcatttcg gactgtatgg cctggggtgg ggggtgggc tcccacggtg   1380 acttgtttac agctgggtgt gactcagtaa agtgaatttt ttttcctttc ttgttttctt   1440
tttttcttgt tgtgggggac tcacatgagc aatggtgtgt gctgggtaat ccttggggtc   1500
ggggaaatgg ccaccaacat ctcagatcac ttcgggagat gggtctgccc cgatcctgac  1560
ctctgcctag ggccttaggc tcacagcgcc tgggcggga ctgattttcc ccgcttcccg    1620
ctcctgcagg gatgataaca atgaaagtaa aagaggtggg gcgggggcca ggcttgggtt   1680 cttttggtctt ttggccctgt gccctggagc agtcccctcc ccctggcttg tactgggggg   1740 gggggatct gcttgaggtg agcctgaggc cccagggtca ggggtgggcg gttatcacct    1800
```

```
ccgggggaag cccggtctgg aacttctcag acagctcttg tcagcgacaa gatttaccaa    1860
actcatttct atgtgcttcc ccatccccc ccaacgccct tccctcctcc tcctccccca    1920
aacctgcact agaaaaaggc tctcgagcct tgctcacccg gagccatctg aggtcccagg    1980
tacccagctc cctgccacat cagagaccct tcttgcactc tgagtgaact gattaaaaaa    2040
aaaaaaaaaa accaagccgg aggtgagccg ggcctcgaag ggaaggttcg cgggtgcggt    2100
ggccgccccg agcctgtgac accaggacat actcccgggg cccgcggtgg gcaagcgaag    2160
tggtgacctg agagctgaca ggctgcgaga gggaaaagta tagacaggcc tagaccaggg    2220
gaaggggagg ggatagagag ctgggcctgc tacgagggga cctgagccag aagcgcactg    2280
gtaaaaccga actccaggac cagagaccca gagatcagag gtgagaggca cagacgcggg    2340
agtcccggct cggcgagggg cgggagtgga ggcggggact aggggggtct ggggaggtgc    2400
gggtttgggg ggaggggcg ggtccttcca cgggatgggg ggaggggcgg gggcccatgt    2460
gaccggctca gaccggttct ggagacaaaa ggggccttag cggccttagc gggacaggcc    2520
ggagcgggag ggagcgaagc atcgagcagt gagcgagtg                          2559
```

<210> SEQ ID NO 15
<211> LENGTH: 2566
<212> TYPE: DNA
<213> ORGANISM: Artificial Sequence
<220> FEATURE:
<223> OTHER INFORMATION: Site directed mutation of midkine promoter

<400> SEQUENCE: 15

```
tgcaccgtga ccagaagagc cgcacgctct tgcaccacgc ggtcagcact ggcagtaagg      60
aagtggtccg ctatctgctg gatcatggta agctgcgttg ctggggctgg gagggagaaa    120
gggggagcca ggctcttagc atccccttc cttttatctg cagcacctcc agagatcctt     180
gatgctgtgg aggagaagtg agtatctgag acacaggccc ctggttcacc agaaaaccac    240
cttccttcag gtctaaccat ttggtcaccc agagcccaag aacccttttgt ggctagcact    300 gagcaccctt cccctcttg ccaaactcct gcccttttcta atggctgttg ggagactgct     360
gggcaggcct agagaactgc aagtgtctac aaccagcccc tgttcccag tggggagacc     420 tgtctacacc aggcagccgc cctgggtcag cgcaccatct gccactacat tgtgaagcc     480 ggggcctcct catgaagaca gatctgcagg tgagttgcct ggcagagcac aaactcaccc    540
tttcccagac ttgggggcag ggctaggaa tttcaagctc ttctgagcca acacagtcca     600
ggccctgaga aacctgagcc agcagggga aagcttgtga cctctgagga taccctcccc     660
ctctggctcc gtagaagaac ccctgccctt tcctaaggcc ttgggggccc ttccacccctt    720 ttccagggcg acactccccg gcagcgcgct gtgaaggctc aagacacaga gctcgctgcc    780
tacctggaga acagacagca ttaccagatg atccacttgc aggaccagga gacagctgtg    840
tagttaaggg gaccatggat caacaaggga cactaccaga ggactctcct tgcccatctc    900
actgccacat tcctgtcaga tggctatggg gggaccctgc cacagggaag gagccccgtg    960
ccaccccctg agaagctgtt cagatctagg gctggactct aaggagctgg actctcacct   1020
gtccctggtt tcatggggaa caggaaacag gctgggctgg ctggttccct cccttcaggg   1080
cagcctccac ctcaccacag cagatggaag ggctggacag agctcagcat cgatgtcagg   1140
gaggcctgca ctcagcagga cttctcaaaag ccacctgatc cttttgggctc tctgagggt   1200 cctgggtacc taacccctcct ctctgatcca cccaccctgg gcatcccaga aactcaagag   1260
cctgctgtat tcacttgccc gctgccctgc ttggcaccta ccctggtctt cctcctcatg   1320
```

```
tatccagcca tttcatttcg gactgtatgg cctggggtgg ggggtggggc tcccacggtg    1380
acttgtttac agctgggtgt gactcagtaa agtgaatttt ttttcctttc ttgttttctt    1440
tttttcttgt tgtgggggac tcacatgagc aatggtgtgt gctgggtaat ccttggggtc    1500
ggggaaatgg ccaccaacat ctcagatcac ttcgggagat gggtctgccc cgatcctgac    1560
ctctgcctag gccttaggc tcacagcgcc tggggcggag ctgattttcc ccgcttcccg     1620
ctcctgcagg gatgataaca atgaaagtaa aagaggtggg gcggggccca ggcttgggtt    1680 cttggtctt ttggccctgt gccctggagc agtcccctcc ccctggcttg tactgggggg     1740 gggggggatct gcttgaggtg agcctgaggc cccagggtca ggggtggggcg ttatcacct   1800 ccggggaag cccggtctgg aacttctcag acagctcttg tcagcgacaa gatttaccaa     1860
actcatttct atgtgcttcc ccatccccccc ccaacgccct tccctcctcc tcctccccca   1920
aacctgcact agaaaaaggc tctcgagcct tgctcacccg gagccatctg aggtcccagg    1980
tacccagctc cctgccacat cagagaccct tcttgcactc tgagtgaact gattaaaaaa    2040 aaaaaaaaaaa accaagccgg aggtgagccg ggcctcgaag ggaaggttcg cgggtgcggt   2100
ggccgccccg agcctgtgac accaggacat actcccgggg cccgcggtgg gcaagcgaag   2160
tggtgacctg agagctgaca ggctgcgaga gggaaaagta tagacaggcc tagaccaggg   2220
gaaggggagg ggatagagag ctgggcctgc tacgagggga cctgagccag aagcgcactg   2280
gtaaaaccga actccaggac cagagaccca gagatcagag gtgagaggca cagacgcggg   2340
agtcccggct cggcgagggg cgggagtgga ggcgggact aggggggtct ggggaggtgc    2400
gggtttgggg ggaggggggcg ggtccttcca cgggatgggg ggaggggcgg gggcccatgt  2460
gaccggctca gaccggttct ggagacaaaa ggggccttag cggccttagc gggacaggcc   2520
ggagcgggag ggagcgaagc atcgagcagt gagcgagtga cgcgtg                  2566
```

<210> SEQ ID NO 16
<211> LENGTH: 2566
<212> TYPE: DNA
<213> ORGANISM: Artificial Sequence
<220> FEATURE:
<223> OTHER INFORMATION: Site directed mutation of midkine promoter

<400> SEQUENCE: 16

```
tgcaccgtga ccagaagagc cgcacgctct tgcaccacgc ggtcagcact ggcagtaagg     60
aagtggtccg ctatctgctg gatcatggta agctgcgttg ctggggctgg gagggagaaa    120 ggggagcca ggctcttagc atccccttc cttttatctg cagcacctcc agagatcctt      180
gatgctgtgg aggagaagtg agtatctgag acacaggccc ctggttcacc agaaaaccac    240
cttccttcag gtctaaccat ttggtcaccc agagcccaag aacccttgt ggctagcact     300 gagcacccct ccccctcttg ccaaactcct gcccttctcta atggctgttg ggagactgct   360
gggcaggcct agagaactgc aagtgtctac aaccagcccc tgttcccag tggggagacc     420 tgtctacacc aggcagccgc cctggtcag cgcaccatct gccactacat tgtggaagcc     480
ggggcctcct catgaagaca gatctgcagg tgagttgcct ggcagagcac aaactcaccc    540
tttcccagac ttgggggcag gctaggaa tttcaagctc ttctgagcca acacagtcca     600
ggccctgaga aacctgagcc agcagggga aagcttgtga cctctgagga taccctccc     660 ctctggctcc gtagaagaac ccctgccctt tcctaaggcc ttggggggccc ttccaccctt   720 ttccagggcg acactccccg gcagcgcgct gtgaaggctc aagacacaga gctcgctgcc    780
tacctggaga acagacagca ttaccagatg atccagcgtg aggaccagga gacagctgtg    840
```

```
tagttaaggg gaccatggat caacaaggga cactaccaga ggactctcct tgcccatctc    900
actgccacat tcctgtcaga tggctatggg gggaccctgc cacagggaag gagcccgtg     960 ccacccctg agaagctgtt cagatctagg gctggactct aaggagctgg actctcacct    1020
gtccctggtt tcatggggaa caggaaacag gctgggctgg ctggttccct cccttcaggg   1080
cagcctccag ctcaccacag cagatggaag ggctggacag agctcagcat cgatgtcagg   1140
gaggcctgca ctcagcagga cttcaaaag ccacctgatc ctttgggctc tctggagggt    1200
cctgggtacc taaccctcct ctctgatcca cccaccctgg gcatcccaga aactcaagag   1260
cctgctgtat tcacttgccc gctgccctgc ttggcaccta ccctggtctt cctcctcatg   1320
tatccagcca tttcatttcg gactgtatgg cctggggtgg ggggtggggc tcccacggtg   1380
acttgtttac agctgggtgt gactcagtaa agtgaatttt ttttcctttc ttgttttctt   1440
tttttcttgt tgtgggggac tcacatgagc aatggtgtgt gctgggtaat ccttggggtc   1500
ggggaaatgg ccaccaacat ctcagatcac ttcgggagat gggtctgccc cgatcctgac   1560
ctctgcctag ggccttaggc tcacagcgcc tggggcggag ctgattttcc ccgcttcccg   1620
ctcctgcagg gatgataaca atgaaagtaa aagaggtggg gcggggggcca ggcttgggtt   1680 ctttggtctt ttggccctgt gccctggagc agtccctcc ccctggcttg tactgggggg    1740 gggggatct gcttgaggtg agcctgaggc cccagggtca gggtgggcg gttatcacct     1800 ccggggaag cccggtctgg aacttctcag acagctcttg tcagcgacaa gatttaccaa    1860
actcatttct atgtgcttcc ccatccccc ccaacgccct tccctcctcc tcctccccca    1920
aacctgcact agaaaaaggc tctcgagcct tgctcacccg gagccatctg aggtcccagg   1980
tacccagctc cctgccacat cagagaccct tcttgcactc tgagtgaact gattaaaaaa   2040
aaaaaaaaaa accaagccgg aggtgagccg ggcctcgaag ggaaggttcg cgggtgcggt   2100
ggccgccccg agcctgtgac accaggacat actcccgggg cccgcggtgg gcaagcgaag   2160
tggtgacctg agagctgaca ggctgcgaga gggaaaagta tagacaggcc tagaccaggg   2220
gaaggggagg ggatagagag ctgggcctgc tacgagggga cctgagccag aagcgcactg   2280
gtaaaaccga actccaggac cagagaccca gagatcagag gtgagaggca cagacgcggg   2340
agtcccggct cggcgagggg cgggagtgga ggcggggact aggggggtct ggggaggtgc   2400
gggtttgggg ggaggggggcg ggtccttcca cgggatgggg ggaggggcgg gggcccatgt  2460
gaccggctca gaccggttct ggagacaaaa ggggccttag cggccttagc gggacaggcc   2520
ggagcgggag ggagcgaagc atcgagcagt gagcgagtga ccttgc                  2566
```

<210> SEQ ID NO 17
<211> LENGTH: 33
<212> TYPE: DNA
<213> ORGANISM: Artificial Sequence
<220> FEATURE:
<223> OTHER INFORMATION: Oligonucleotide used as upstream primer for obtaining midkine promoter

<400> SEQUENCE: 17
gcgcgacgcg ttgacctcat gcaccgtgac cag                                33

<210> SEQ ID NO 18
<211> LENGTH: 33
<212> TYPE: DNA
<213> ORGANISM: Artificial Sequence
<220> FEATURE:
<223> OTHER INFORMATION: Oligonucleotide used as downstream primer for obtaining midkine promoter -continued

<400> SEQUENCE: 18
gcgcgacgcg tcactcgctc actgctcgat gct                            33

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19
gccatccacg ctgttttgac                                           20

<210> SEQ ID NO 20
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 20
ggtctttgac ttggtcttgg agg                                       23

<210> SEQ ID NO 21
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 21
gcctggaaag tgggacaaga tg                                        22

<210> SEQ ID NO 22
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 22
ggaagacaaa aggcactggt gg                                        22

<210> SEQ ID NO 23
<211> LENGTH: 29
<212> TYPE: DNA
<213> ORGANISM: Artificial Sequence
<220> FEATURE:
<223> OTHER INFORMATION: Synthetic oligonucleotide for HIF1-alpha
      fragment amplification

<400> SEQUENCE: 23
gtttctgctg ccttgtatag gagcaatta                                 29

<210> SEQ ID NO 24
<211> LENGTH: 27
<212> TYPE: DNA
<213> ORGANISM: Artificial Sequence
<220> FEATURE:
<223> OTHER INFORMATION: Synthetic oligonucleotide for HIF1-alpha
      fragment amplification

<400> SEQUENCE: 24
aaagttcacc tgagcctaat agtccag                                   27

```
<210> SEQ ID NO 25
<211> LENGTH: 695
<212> TYPE: DNA
<213> ORGANISM: Mus musculus
<220> FEATURE:
<221> NAME/KEY: CDS
<222> LOCATION: (86)...(508)

<400> SEQUENCE: 25
ggggtacgct gagacatcgg ttccaagtcc tccctccgtc tcccccttgt cggtccgacg      60
ttttgggcct ggaaagtggg acaag atg cag cac cga ggc ttc ttc ctt ctc     112
                            Met Gln His Arg Gly Phe Phe Leu Leu
                              1               5 gcc ctt ctt gcc ctc ttg gtg gtc acg tcc gcg gtg gcc aaa aaa aaa    160
Ala Leu Leu Ala Leu Leu Val Val Thr Ser Ala Val Ala Lys Lys Lys
 10              15                  20                  25 gag aag gtg aag aag ggc agc gag tgt tcg gag tgg acc tgg ggg ccc    208
Glu Lys Val Lys Lys Gly Ser Glu Cys Ser Glu Trp Thr Trp Gly Pro
             30                  35                  40 tgc acc ccc agc agc aag gac tgc ggc atg ggc ttc cgc gag ggt acc    256
Cys Thr Pro Ser Ser Lys Asp Cys Gly Met Gly Phe Arg Glu Gly Thr
         45                  50                  55 tgt ggg gcc cag acc cag cgc gtc cat tgc aag gtg ccc tgc aac tgg    304
Cys Gly Ala Gln Thr Gln Arg Val His Cys Lys Val Pro Cys Asn Trp
     60                  65                  70 aag aag gaa ttt gga gcc gac tgc aaa tac aag ttt gag agc tgg ggg    352
Lys Lys Glu Phe Gly Ala Asp Cys Lys Tyr Lys Phe Glu Ser Trp Gly
 75                  80                  85 gcg tgt gat ggg agc act ggc acc aaa gcc cgc caa ggg acc ctg aag    400
Ala Cys Asp Gly Ser Thr Gly Thr Lys Ala Arg Gln Gly Thr Leu Lys
             90                  95                 100                 105 aag gcg cgg tac aat gcc cag tgc cag gag acc atc cgc gtg act aag    448
Lys Ala Arg Tyr Asn Ala Gln Cys Gln Glu Thr Ile Arg Val Thr Lys
                    110                 115                 120 ccc tgc acc tcc aag acc aag tca aag acc aaa gcc aag aaa gga aaa    496
Pro Cys Thr Ser Lys Thr Lys Ser Lys Thr Lys Ala Lys Lys Gly Lys
         125                 130                 135 gga aag gac taa gtcaggaggc cagagagcct ccggcctcgc ctggagcctg        548
Gly Lys Asp  *
         140 aacggagccc tcctctccca caggcccaag atataaccca ccagtgcctt ttgtcttcct     608 gtcagctctg tcaatcacgc ctgtcctcta cgcccacacc aagtgcccaa agtggggagg     668 gacaagagat tttggaaagt gagcctc                                          695

<210> SEQ ID NO 26
<211> LENGTH: 140
<212> TYPE: PRT
<213> ORGANISM: Mus musculus

<400> SEQUENCE: 26

Met Gln His Arg Gly Phe Phe Leu Leu Ala Leu Leu Ala Leu Leu Val
  1               5                  10                  15

Val Thr Ser Ala Val Ala Lys Lys Lys Glu Lys Val Lys Lys Gly Ser
             20                  25                  30

Glu Cys Ser Glu Trp Thr Trp Gly Pro Cys Thr Pro Ser Ser Lys Asp
         35                  40                  45

Cys Gly Met Gly Phe Arg Glu Gly Thr Cys Gly Ala Gln Thr Gln Arg
     50                  55                  60

Val His Cys Lys Val Pro Cys Asn Trp Lys Lys Glu Phe Gly Ala Asp
 65                  70                  75                  80
```

```
Cys Lys Tyr Lys Phe Glu Ser Trp Gly Ala Cys Asp Gly Ser Thr Gly
            85                  90                  95

Thr Lys Ala Arg Gln Gly Thr Leu Lys Lys Ala Arg Tyr Asn Ala Gln
            100             105                 110

Cys Gln Glu Thr Ile Arg Val Thr Lys Pro Cys Thr Ser Lys Thr Lys
        115                 120                 125

Ser Lys Thr Lys Ala Lys Lys Gly Lys Gly Lys Asp
    130             135             140
```

METHOD OF SCREENING A MIDKINE MODULATING AGENT

CROSS-REFERENCE TO RELATED APPLICATIONS

This application claims priority to and benefit of U.S. Provisional Applications: 60/519,473, filed on Nov. 12, 2003; 60/541,580, filed on Feb. 4, 2004; and 60/580,481, filed on Jun. 17, 2004; which are herein incorporated by reference in their entirety.

FIELD OF THE INVENTION

The invention relates to the field of modulation of pulmonary disorders, smooth muscle related disorders, and particularly pulmonary smooth muscle disorders.

BACKGROUND OF THE INVENTION

Smooth muscle cells are a developmentally complex population. Smooth muscle cells arise in multiple regions of the embryo from different precursor populations. For example, studies in chick/quail chimeras have shown that unlike smooth muscle cells in the coronary arteries, smooth muscle cells in the great vessels are derived from a subpopulation of mesenchymal neural crest cells (Hood et al. (1992) *Anat. Rec.* 234:291-300; Rosenquist et al. (1990) *Ann. NY Acad. Sci.* 588:106-119; Kirby et al. (1983) *Science* 220:1059-1061; Le Lievre et al (1975) *J. Embryol. Exp. Morphol.* 34:125-154; herein incorporated by reference in their entirety.) Furthermore, the smooth muscle cells in most visceral organs, including those of the respiratory system, are thought to originate from local mesenchyme (Cunha et al. (1992) *Epith. Cell Biol.* 1:76-83, herein incorporated by reference).

Unlike skeletal and cardiac muscle cells, where cell differentiation is accompanied by stable expression of muscle-specific genes (Weintraub et al. (1991) *Science* 251:761-766 and Olson et al. (1992) *Genes & Dev.* 4:1454-1461, herein incorporated by reference in their entirety), smooth muscle cells display remarkable phenotypic plasticity, and retain the capacity to re-enter the cell cycle (Schwartz et al (1986) *Circ. Res.* 58:427-444). This unusual characteristic of smooth muscle cell phenotypic modulation is often associated with the loss of many smooth muscle cell-specific markers (Glukhova et al (1991) *Am. J. Physiol.* 261:78-80; Frid et al (1992) *Dev. Biol.* 153:185-193; herein incorporated by reference). Such alterations in smooth muscle cell proliferation and differentiation are associated with a variety of vascular diseases including atherosclerosis, restenosis following angioplasty, and hypertension.

Smooth muscle proliferation is associated with numerous pulmonary disorders such as asthma, airway hyperactivity, idiopathic pulmonary hypertension, pulmonary hypertension, secondary pulmonary hypertension, COPD, and pulmonary hypotension. According to the Centers for Disease Control and Prevention, asthma affects almost six percent of American children and over six percent of American adults. Pulmonary hypertension resulted in 7,139 deaths and 174,854 hospital visits in 1998. Currently, there is a low survival prognosis and no cure or simple treatment for pulmonary hypertension (Gerberding, J. (2003) *Report to Congress Pulmonary Hypertension* Centers for Disease Control and Prevention, herein incorporated by reference). Numerous disorders including, but not limited to emphysema, bronchitis, scleroderma, CREST, and congenital disorders, result in secondary pulmonary hypertension. Additionally, the N.I.H. reports that chronic obstructive pulmonary disorder is the fourth leading cause of death in the U.S. (N.I.H. Publication No. 03-5229, March 2003, herein incorporated by reference.)

Thus, there is a need in the art for a better understanding of the molecular mechanisms that regulate smooth muscle cell proliferation and differentiation, especially in respect to pulmonary disease. Development of methods of regulating smooth muscle proliferation is desirable. Development of methods of modulating pulmonary disorders is desirable. Development of methods of modulating pulmonary smooth muscle cell related disorders is particularly desirable.

SUMMARY OF THE INVENTION

Compositions and methods for diagnosis and therapy of disorders, particularly smooth muscle related disorders, pulmonary disorders, pulmonary smooth muscle related disorders, and pulmonary vascular smooth muscle related disorders are provided. The invention encompasses methods of modulating mammalian midkine activity, including modulating midkine expression levels. In an aspect of the invention, pulmonary midkine activity, including midkine expression levels, is modulated. The compositions and methods of the invention can be targeted toward pulmonary hypertension, chronic obstructive pulmonary disorder, asthma, and hypoxia related disorders.

In a first embodiment, the invention provides a method of preferentially modulating pulmonary tissue midkine expression levels, particularly in a mammal. Transforming a mammalian cell with an isolated nucleic acid molecule comprising an expression cassette with a pulmonary tissue-preferred promoter operably linked to a nucleotide sequence of interest directly or indirectly alters midkine expression levels in pulmonary tissue. Nucleotide sequences of interest include, but are not limited to, midkine (SEQ ID NO:1), TTF-1 (SEQ ID NO:3), HIF-1 (SEQ ID NO:5), and fragments and variants thereof having midkine modulating activity or encoding a polypeptide having midkine modulating activity. Fragments and variants of a nucleotide sequence of interest include nucleotide sequences having at least 90% identity to a nucleotide sequence of interest, nucleotide sequences having at least 30 contiguous nucleotides of a nucleotide sequence of interest, nucleotide sequences that hybridize to a nucleotide sequence of interest under stringent conditions, and nucleotide sequences that complement a nucleotide sequence of interest. The method may be used to increase or decrease midkine expression levels. In an embodiment, the transformed cell is contained in an organism.

In a second embodiment, the invention provides a method of modulating smooth muscle development in a mammal by administering a midkine-modulating agent to the mammal. An aspect of smooth muscle development is proliferation. Another aspect of smooth muscle development is differentiation. In an aspect of the invention, the agent is administered to the pulmonary tissue of a mammal. In an aspect of the invention the cell is contained in a mammal such as, but not limited to, a human, a mouse, a rat, a hamster, a rabbit, a dog, a pig, a goat, a monkey, a chimpanzee, and a cow. The midkine-modulating agent is not limited to a particular mode of action but may bind midkine, bind a midkine receptor, or may alter midkine expression levels. In another aspect of the invention, the modulating agent includes, but is not limited to a nucleic acid molecule, a polypeptide, a peptide, a glycoprotein, a transcription factor, an antibody, a small molecule, a midkine binding compound, or a HIF-1α modulating agent. An agent that is an isolated nucleic acid molecule comprises an expression cassette further comprising a promoter operably linked to a nucleotide sequence of interest. Promoters useful in the invention include, but are not limited to, inducible promoters, such as HIF-1 binding promoters, constitutive promoters; tissue-preferred promoters; pulmonary tissue preferred promoters; and TTF-1 (thyroid specific transcription factor, also known as T-EBP, Ttf1, and Nkx2.1) binding promoters.

In a third embodiment, the invention provides a method of modulating pulmonary smooth muscle development in a mammal by transforming a pulmonary cell with an isolated nucleic acid molecule comprising an expression cassette comprising a pulmonary tissue preferred promoter operably linked to a nucleotide sequence of interest. An aspect of smooth muscle development is proliferation. Another aspect of smooth muscle development is differentiation.

In a fourth embodiment, the invention provides a method of modulating smooth muscle cell related disorders by administering a midkine-modulating agent to a subject exhibiting a smooth muscle cell related disorder. In an aspect of the invention, the method of modulating the disorder decreases a smooth muscle cell related disorder. In another aspect, the method may be used to increase a smooth muscle cell related disorder. In an aspect of the invention, the agent is administered to pulmonary tissue.

In a fifth embodiment, the invention provides a method of modulating a pulmonary disorder. The method comprises the step of transforming a pulmonary cell with an isolated nucleic acid molecule comprising an expression cassette comprising a pulmonary tissue-preferred promoter operably linked to a nucleotide sequence of interest.

In a sixth embodiment, the invention provides a method of modulating a pulmonary smooth muscle-cell related disorder. The method comprises the step of transforming a pulmonary cell with an isolated nucleic acid molecule comprising an expression cassette comprising a pulmonary tissue-preferred promoter operably linked to a nucleotide sequence of interest described elsewhere herein. Pulmonary smooth muscle cell-related disorders include, but are not limited to asthma, airway hyperactivity, and pulmonary hypertension. Pulmonary smooth muscle cell related disorders are further discussed elsewhere herein.

In a seventh embodiment, the invention provides a method of detecting a midkine pathway abnormality. The method involves obtaining a sample and assaying the midkine expression levels in the sample.

In an eighth embodiment, the invention provides a method of detecting a pulmonary disorder. The method involves obtaining a pulmonary tissue sample and assaying the midkine expression levels in the sample.

In a ninth embodiment, the invention provides a method of screening for a midkine pathway abnormality. The method involves providing an isolated nucleic acid molecule comprising an expression cassette comprising a modified midkine promoter operably linked to a nucleotide sequence encoding a reporter. In the invention, the promoter is a modified midkine promoter having the nucleotide sequence set forth in SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, or SEQ ID NO:16 or fragments or variants thereof capable of initiating transcription in a mammalian cell. The invention comprises incubating the isolated nucleic acid molecule with a test sample and assaying the reporter. The reporter utilized in the invention can be any reporter known in the art including, but not limited to, luciferases, blue fluorescent proteins, green fluorescent proteins, CAT, GUS, β-galactosidases, and midkine. In one aspect, the isolated nucleic acid molecule is transformed into a cell. In an aspect of the invention, incubating the isolated nucleic acid molecule with a test sample occurs within a cell. In another aspect, incubating the nucleic acid molecule with a test sample occurs in vitro. In an aspect of the invention, the test sample is selected from the group including, but not limited to, cellular contents, cell lysates, and cellular fractions.

In a tenth embodiment, the invention provides a method of screening subjects for a pulmonary disorder. The method involves providing an isolated nucleic acid molecule comprising an expression cassette comprising a promoter operably linked to a nucleotide sequence encoding a reporter. In the invention, the promoter is a modified midkine promoter having the nucleotide sequence set forth in SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, or SEQ ID NO:16 or fragments or variants thereof capable of initiating transcription in a mammalian cell. The invention comprises incubating the isolated nucleic acid molecule with a pulmonary tissue sample and assaying the reporter.

In an eleventh embodiment, the invention provides a method of treating a pulmonary disorder. The method comprises the step of administering a therapeutically effective amount of a midkine modulating agent to a subject exhibiting the disorder. In an aspect of the invention, the pulmonary disorder is a smooth muscle cell related disorder.

In a twelfth embodiment, the invention provides a method of treating a pulmonary disorder comprising the step of transforming a cell with an isolated nucleic acid molecule comprising an expression cassette comprising a pulmonary tissue-preferred promoter operably linked to a nucleotide sequence of interest described elsewhere herein.

In a thirteenth embodiment, the invention provides a kit comprising an isolated nucleic acid molecule comprising an expression cassette comprising a modified midkine promoter operably linked to a nucleotide sequence encoding a reporter.

In a fourteenth embodiment, the invention provides a transgenic mouse comprising at least one stably incorporated expression cassette in the genome of at least one cell, said expression cassette comprising a promoter operably linked to a midkine nucleotide sequence. In an aspect of the invention, the promoter is an inducible, constitutive, or tissue-preferred promoter. The invention further provides transgenic tissue and transgenic cells obtained from a transgenic mouse of the invention, particularly pulmonary tissue and pulmonary cells. In an aspect of the invention, the mouse exhibits altered midkine expression levels. In an aspect of the invention, the mouse exhibits pulmonary vasculature hypertrophy. In an aspect of the invention, the mouse exhibits a pulmonary disorder. In an additional aspect of the invention, the mouse exhibits an altered susceptibility to a pulmonary disorder. In another aspect, the invention provides a method of identifying midkine modulating agents comprising providing a first and second transgenic cell, administering a compound of interest to the first cell, incubating both the first and second cells for a period of time, and monitoring the cells for a modulation of midkine activity.

In a fifteenth embodiment, the invention provides a method of preferentially modulating pulmonary tissue midkine expression levels, particularly in a mouse. The method involves providing a transgenic mouse comprising at least one stably incorporated expression cassette in the genome of at least one cell, said expression cassette comprising an inducible promoter operably linked to a midkine nucleotide sequence. In the method, the transgenic midkine mouse is mated with a transgenic mouse comprising at least one stably incorporated expression cassette in the genome of at least one cell, said expression cassette comprising a pulmonary-tissue preferred promoter operably linked to a nucleotide sequence encoding an activator molecule. Double transgenic mice are obtained. In an aspect of the invention, a regulating compound such as but not limited to, tetracycline or a tetracycline analog, is administered to the double transgenic mice.

BRIEF DESCRIPTION OF THE DRAWINGS

FIG. 5, panel B depicts results obtained from RT-PCR reactions performed on 2 μg total RNA isolated from double transgenic (SP-C-rtTA$^{+/tg}$, (tetO)$_7$-CMV-MK$^{+/tg\ or\ tg/tg}$) and control littermates in the presence (+Dox) or absence (−Dox) of doxycycline.

FIG. 7 presents average right ventricle hypertrophy (RVH), distal pulmonary vessel counts (No. distal vessels), and percent distal muscularization of mice in normoxic and hypoxic conditions. For comparison the results obtained from wild-type (control) and double transgenic mice (SP-C-rtTA$^{+/tg}$, (tetO)$_7$-CMV-MK$^{+/tg\ or\ tg/tg}$) are presented. The standard error values follow the means.

Figure 12:
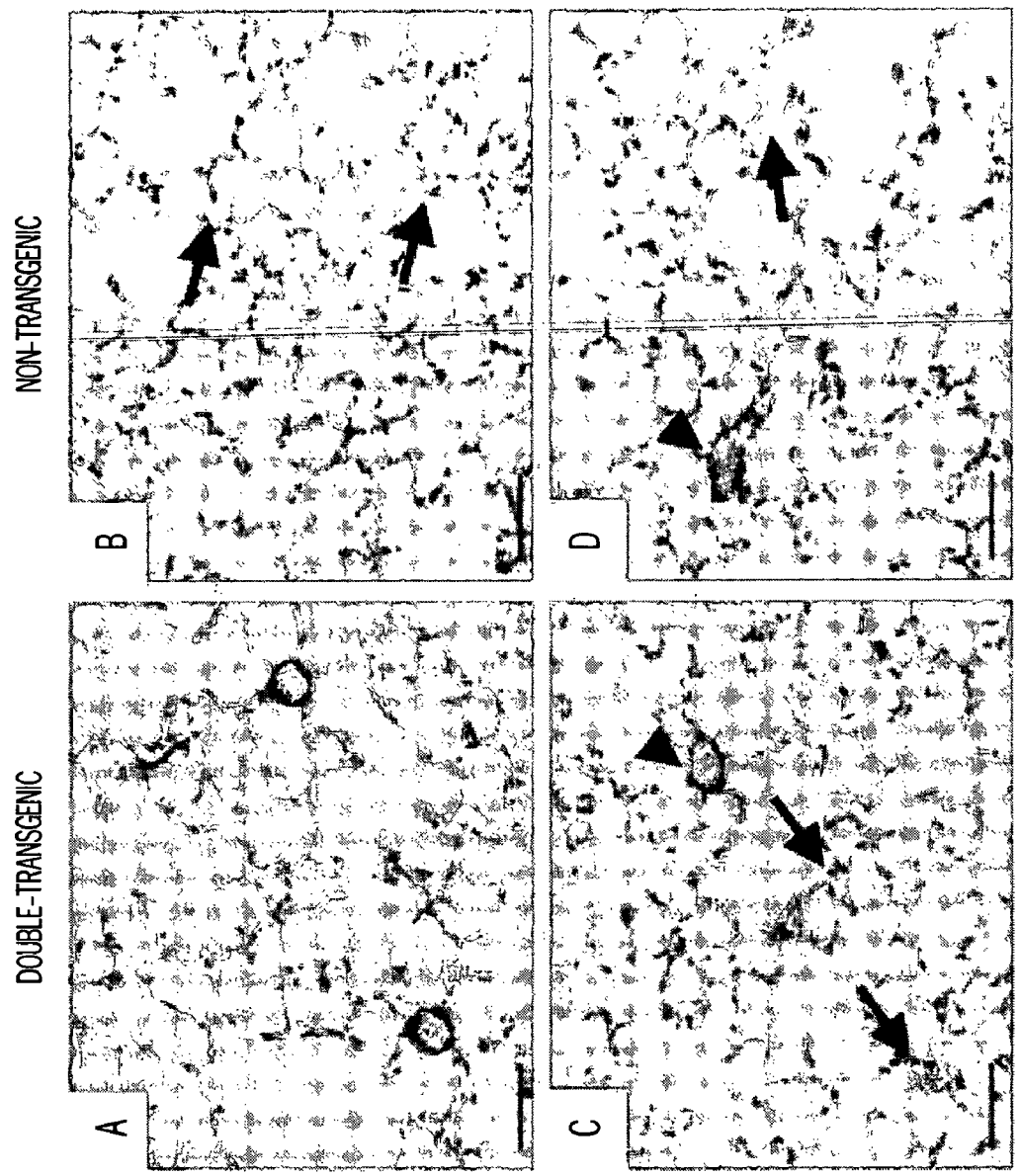
Figure 13A:
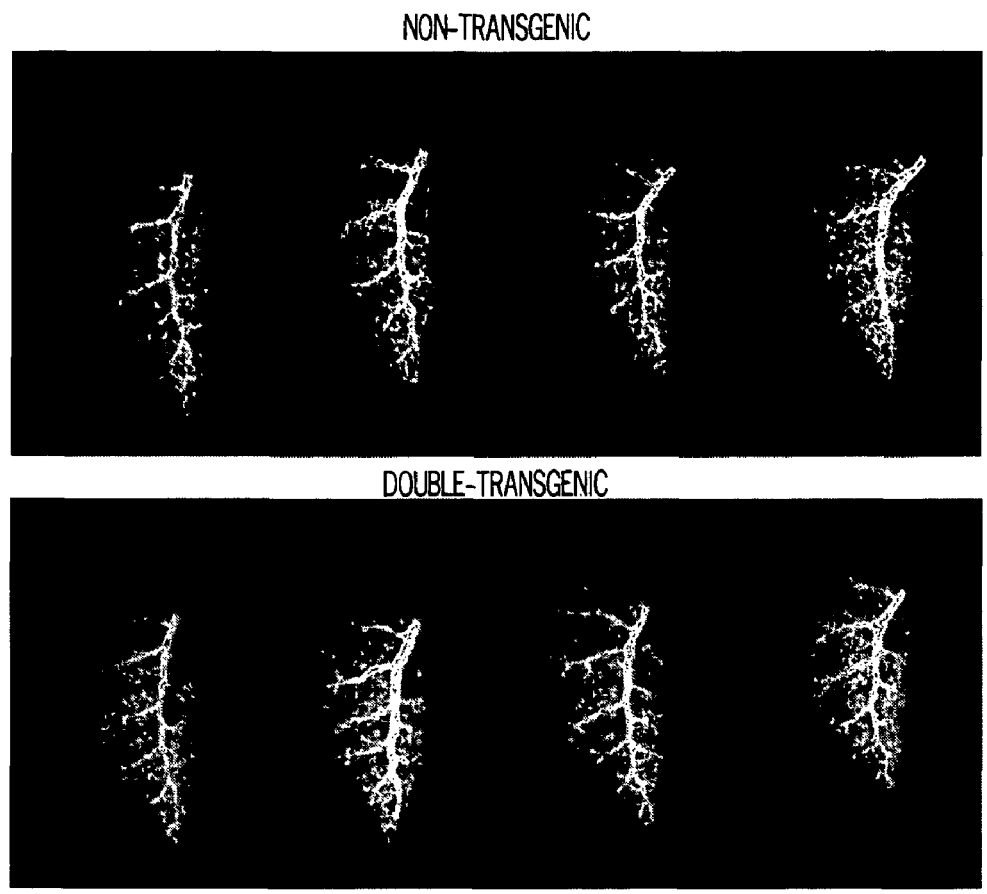
Figure 13B:
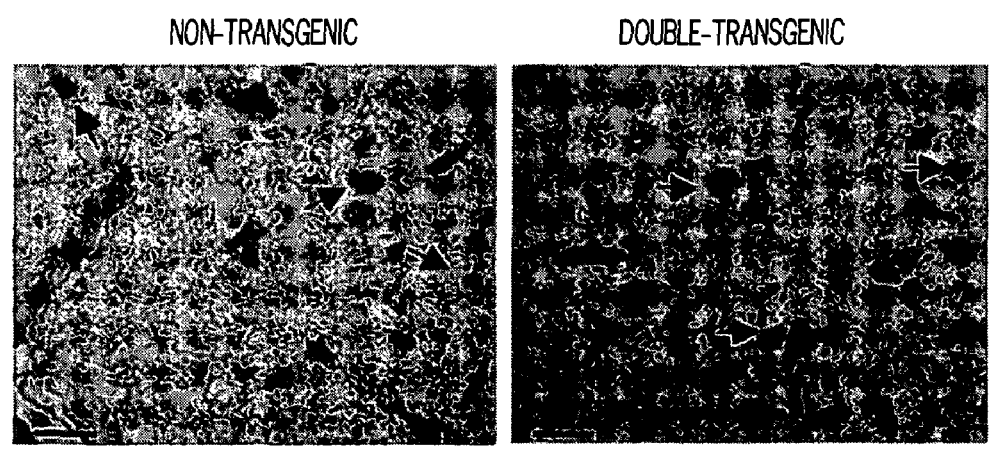
Figure 13C:
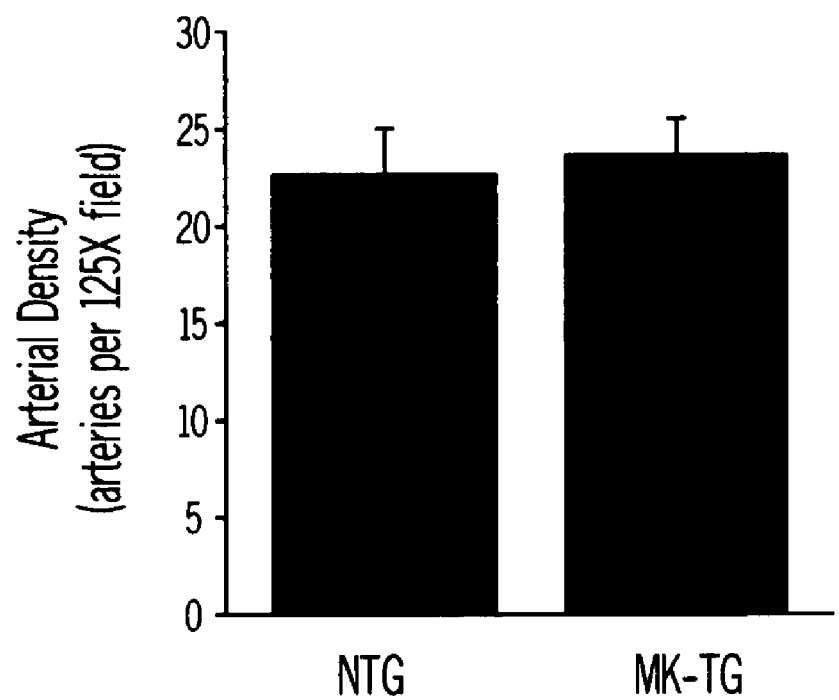
Figure 13D:
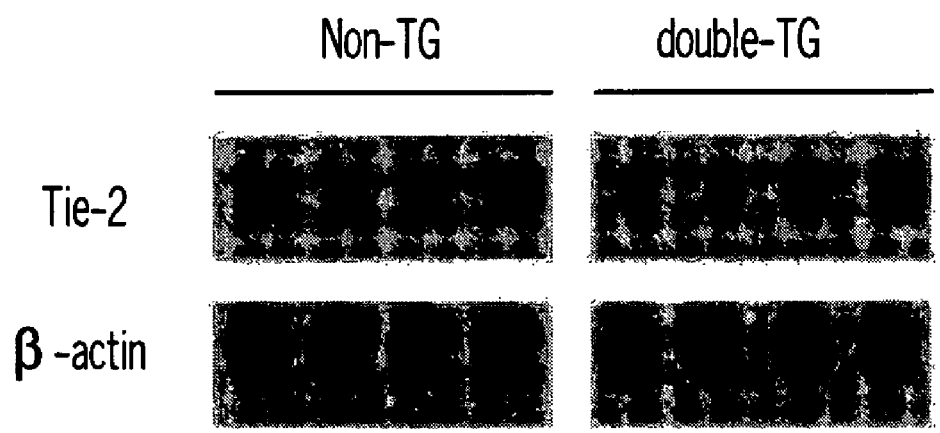

FIG. 12 presents micrographs of tissue sections from double-transgenic and non-transgenic mice stained with α-SMA specific antibodies. Small blood vessels are indicated with arrows. Large blood vessels are indicated with arrowheads. The tissue in panels A and C were obtained from double-transgenic mice. The tissue in panels B and D were obtained from non-transgenic littermates. Panels A and B present tissue from animals fed doxycycline from conception to post-natal day 21. Panels C and D present tissue from animals fed doxycycline from post-natal day 21 to 9 weeks of age. The bar indicates 50 μm.

FIG. 13 presents results of peripheral pulmonary arterial pattern assessments. Panel A presents pulmonary arteriograms performed on adult non-transgenic (top row) and double transgenic (bottom row) mice. Panel B presents hematoxylin and eosin stained pulmonary tissue sections obtained from non-transgenic and double transgenic mice. The bar indicates 100 μm. Panel C presents a summary of pulmonary arterial density in non-transgenic (NTG) and double transgenic (MK-TG) mice. N=8. Panel D presents the results of Western blot analysis of Tie-2 and β-actin expression in whole lung homogenates from non-transgenic (Non-TG) and double transgenic (double-TG) mice.

Figure 14A:
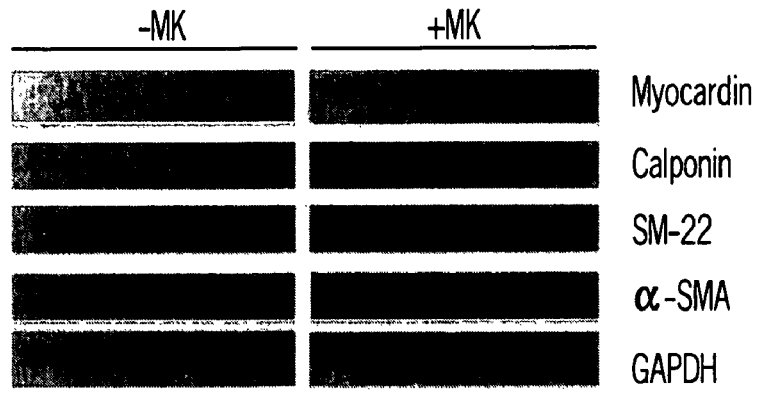
Figure 14B:
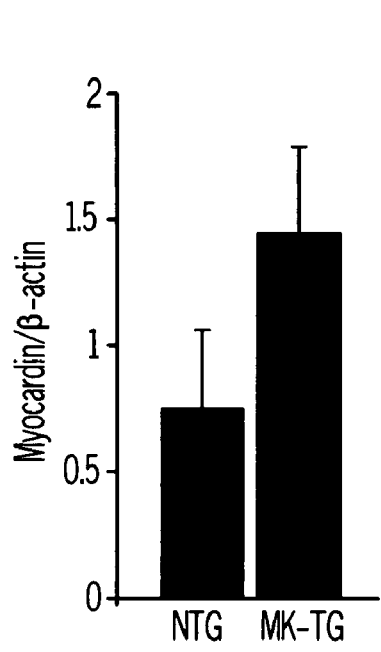
Figure 14C:
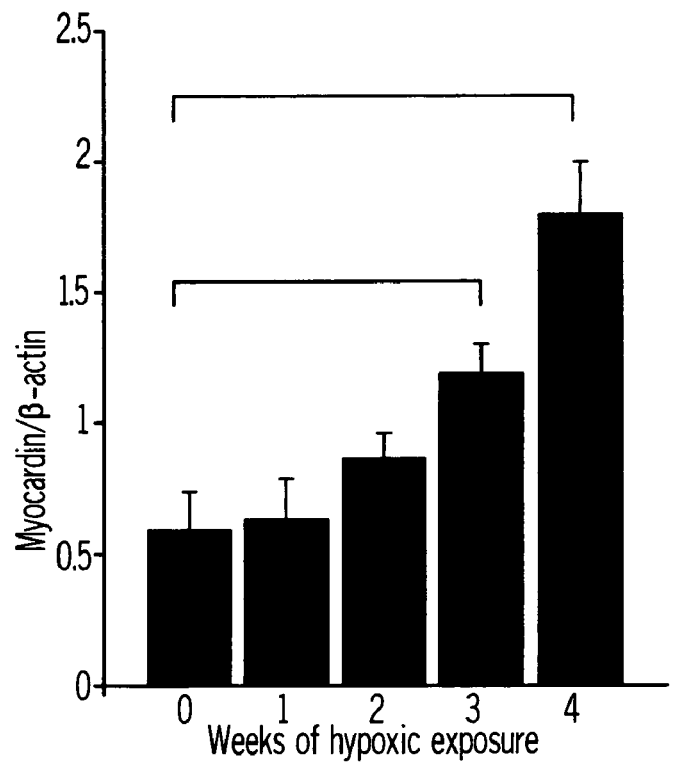

FIG. 14, panel A presents results obtained from RT-PCR analysis of myocardin, calponin, SM-22, α-SMA, and GAPDH expression in MFLM-4 cells incubated with a placebo (−MK) or with midkine (+MK). Panel B presents results of real time RT-PCR analysis of myocardin expression relative to β-actin in lungs of transgenic (MK-TG) and non-transgenic mice (NTG). Panel C presents the myocardin/β-actin expression ratio in the lungs of CAST/eiJ mice exposed to hypoxia for the indicated number of weeks.

DETAILED DESCRIPTION OF THE INVENTION

The present invention provides methods of modulating midkine activity, midkine expression levels, and pulmonary midkine expression levels. The invention further provides methods of modulating smooth muscle cell development, particularly pulmonary smooth muscle cell development, more particularly pulmonary vascular smooth muscle cell development. Additionally the invention provides methods of modulating smooth muscle cell related disorders, pulmonary disorders, pulmonary smooth muscle cell related disorders, and pulmonary vascular smooth muscle cell related disorders. The invention provides methods of detecting midkine pathway abnormalities and pulmonary disorders. Further the invention provides methods of screening for a midkine pathway abnormality and for a pulmonary disorder. The invention provides methods of treating a pulmonary disorder. In addition, the invention provides methods of identifying a midkine modulating agent, smooth muscle cell development modulating agents, and pulmonary disorder modulating agents. Compositions of the invention include transgenic mice expressing midkine, particularly mice expressing midkine in an inducible, pulmonary tissue-preferred manner. Expression of midkine may alter a transgenic animal's susceptibility to smooth muscle cell related disorders or to pulmonary disorders, particularly pulmonary smooth muscle cell related disorders. Additionally the invention provides modified midkine promoters, and kits comprising a modified midkine promoter.

The invention relates to compositions and methods drawn to the murine midkine promoter, modified midkine promoters, and transgenic animals comprising a midkine transgene. The promoter sequences are useful for screening for a midkine pathway abnormality, screening subjects for a pulmonary disorder, evaluating compounds for midkine modulating activity, evaluating compounds for effects on smooth muscle cell development, and evaluating compounds for pulmonary disorder modulating activity. Methods of modulating midkine activity, modulating smooth muscle cell development, pulmonary development, pulmonary smooth muscle development, smooth muscle cell related disorders, pulmonary disorders, and pulmonary smooth muscle cell disorders involve administering a midkine modulating agent to a cell or subject. Particularly, the invention provides methods of modulating midkine expression that involve administering a midkine modulating agent.

A "midkine modulating agent" is a compound that modulates a midkine activity. Modulation may be an increase or decrease in a midkine activity. A midkine modulating compound will modulate a midkine activity by at least 1%, 5%, preferably 10%, 20%, more preferably 30%, 40%, 50%, 60%, yet more preferably 70%, 80%, 90%, or 100% as compared to an untreated or placebo treatment effect. By "midkine activity" is intended any activity exhibited by the wild-type murine midkine described herein. Such activities include, but are not limited to, midkine expression, immunogenicity, midkine receptor binding, heparin binding, modulation of cell differentiation, modulation of cell proliferation, protein tyrosine phosphatase binding, nucleolin binding, retinoic acid responsiveness, immunoreactivity, growth enhancement, neurite outgrowth, chemotactic activity, mitogenesis, angiogenesis modulation, neuron survival modulation, fibrinolysis, myocardin modulation, cell growth, cell migration, and tumorigenesis (Muramatsu et al. (1993) *Dev. Biol.* 159:392-402; Choundhri et al. (1997) *Cancer Res.* 57:1814-1819; Owada et al. (1999) *J. Neurochem* 73:2084-2092; Kojima et al. (1995) *J. Biol. Chem.* 270:9590-9596; Muramatsu & Muramatsu (1991) *Biochem. Biophys. Res. Commun.* 177:652-658; Kurtz et al. (1995) *Crit. Rev. Oncol.* 6:151-177; Tsutsui et al. (1993) *Cancer Res.* 53:1281-1285; Nakagawara et al. (1995) *Cancer Res.* 55:1792-1797; Garver et al. (1993) *Am J. Respir. Cell Biol.* 9:463-466; O'Brien et al. (1996) *Cancer Res.* 56:2515-2518; Kaname et al. (1996) *Biochem. Biophys. Res. Commun.* 219:256-260; Miyashiro et al. (1996) *Cancer Lett* 106:287-291; Miyashiro et al. (1997) *Breast Cancer Res. Treat.* 43:1-6; Takada et al. (1997) *J. Biochem.* 122:453-458; Maeda et al (1999) *J. Biol. Chem.* 274:12474-12479; Horiba et al. (2000) *J. Clin. Invest.* 105:489-495; Aridome et al. (1998) *Br. J Cancer* 78:472-477; Walker, John, ed. (2002) *Protein Protocols on CD-ROM v.* 2; and Ausubel et al., eds. (1995) *Current Protocols in Molecular Biology*, (Greene Publishing and Wiley-Interscience, New York; U.S. patent application Nos. 20020034768 and 20030053989; herein incorporated by reference in their entirety). Modulation of midkine activity includes but is not limited to modulation of a midkine activity such as protein tyrosine phosphatase binding or modulation of midkine expression levels. Thus, modulation of midkine expression is an alteration of a midkine activity. Methods for assaying midkine activity are known in the art and are described elsewhere herein.

In an embodiment, the invention provides compositions with an altered midkine activity and methods of modulating midkine activity. By "altered midkine activity" is intended a change of at least 1%, 5%, preferably 10%, 20%, more preferably 30%, 40%, 50%, 60%, 70%, 80%, 90%, 99% or more in a midkine activity. The change may be an increase or a decrease in the activity. Further, a compound that increases one midkine activity may decrease a different midkine activity.

It is understood that any midkine activity assay can be used to assay midkine modulating activity including, but not limited to, expression assays, immunogenicity, myocardin interaction assays, myocardin activation assays, receptor binding assays, heparin binding assays, cell differentiation assays, cell adhesion assays, FACS analysis, protein tyrosine phosphatase binding assays, growth assays, chemotactic assay, Western blots, EM, SEM, light microscopy, retinoic acid responsiveness assays, nucleolin binding assays, size exclusion chromatography, and capture ELISAs with multiple midkine antibodies. (Reynolds et al. (2004) *J. Biol. Chem.* 279: 37124-37132; Reynolds et al. (2003) *Dev. Dyn.* 227: 227-237; Muramatsu et al. (1993) *Dev. Biol.* 159:392-402; Choundhri et al. (1997) *Cancer Res.* 57:1814-1819; Owada et al. (1999) *J. Neurochem* 73:2084-2092; Kojima et al. (1995) *J. Biol. Chem.* 270:9590-9596; Muramatsu & Muramatsu (1991) *Biochem. Biophys. Res. Commun.* 177:652-658; Kurtz et al. (1995) *Crit. Rev. Oncol.* 6:151-177; Tsutsui et al. (1993) *Cancer Res.* 53:1281-1285; Nakagawara et al. (1995) *Cancer Res.* 55:1792-1797; Garver et al. (1993) *Am J. Respir. Cell Biol.* 9:463-466; O'Brien et al. (1996) *Cancer Res.* 56:2515-2518; Kaname et al. (1996) *Biochem. Biophys. Res. Commun.* 219:256-260; Miyashiro et al. (1996) *Cancer Lett* 106:287-291; Miyashiro et al. (1997) *Breast Cancer Res. Treat.* 43:1-6; Takada et al. (1997) *J. Biochem.* 122:453-458; Maeda et al (1999) *J. Biol. Chem.* 274:12474-12479; Horiba et al. (2000) *J. Clin. Invest.* 105:489-495; Aridome et al. (1998) *Br. J Cancer* 78:472-477; Walker, John, ed. (2002) *Protein Protocols on CD-ROM v.* 2; and Ausubel et al., eds. (1995) *Current Protocols in Molecular Biology*, (Greene Publishing and Wiley-Interscience, New York; U.S. patent application Nos. 20020034768 and 20030053989; herein incorporated by reference in their entirety).

A "HIF-1α modulating agent" is a compound that modulates a HIF-1α activity such as altering midkine activity, modulating the HIF-1α/β interaction, oxygen level responsiveness, DNA binding, nuclear translocation, and degradation susceptibility. A HIF-1α modulating compound will modulate a HIF-1α activity by at least 1%, 5%, preferably 10%, 20%, more preferably 30%, 40%, 50%, 60%, yet more preferably 70%, 80%, 90%, or 100% as compared to an untreated or placebo treatment effect. By "HIF-1α activity" is intended any activity exhibited by the wild-type murine HIF-1α. Such activities include, but are not limited to, HIF-1α expression, interacting with HIF-1β, binding DNA, cellular translocation, degradation susceptibility, and midkine stimulation. Thus, modulation of HIF-1α expression is an alteration of HIF-1α activity. Methods for assaying HIF-1α activity are known in the art and are described elsewhere herein.

In an embodiment, the invention provides compositions with an altered HIF-1α activity and methods of modulating HIF-1α activity. By "altered HIF-1α activity" is intended a change of at least 1%, 5%, preferably 10%, 20%, more preferably 30%, 40%, 50%, 60%, 70%, 80%, 90%, 99% or more in a HIF-1α activity. The change may be an increase or a decrease in the activity. Further, a compound that increases one HIF-1α activity may decrease a different HIF-1α activity.

It is understood that any HIF-1α activity assay can be used to assay HIF-1α modulating activity including, but not limited to, expression assays, DNA binding assays, HIF-1α/β binding assays, HIF-1α/β dimerization assays, Western blots, EM, SEM, light microscopy, DAPI staining, and translocation assays. (Walker, John, ed. (2002) *Protein Protocols on CD-ROM v.* 2; and Ausubel et al., eds. (1995) *Current Protocols in Molecular Biology*, (Greene Publishing and Wiley-Interscience, New York).

An embodiment of the invention provides methods of modulating myocardin activity. In the methods modulating midkine activity modulates myocardin activity. By "myocardin activity" is intended any activity associated with murine myocardin including, but not limited to, smooth muscle gene regulation (Veyssier-Belot & Cacoub (1999) *Cardiovascular Research* 44:274-282), serum response factor interaction, myogenic activity, modulation of α-SMA, modulation of calponin, immunogenicity, and modulation of SM-22. Methods of detecting myocardin activity are known in the art; any method of assaying myocardin activity may be used in the methods of the invention.

In an embodiment, the invention provides a method of altering expression of a native midkine nucleotide sequence in an animal, particularly of modulating midkine expression in a tissue preferred manner. In the embodiment a midkine modulating agent comprising an expression cassette comprising a promoter operably linked to a nucleotide sequence having midkine modulating activity or encoding a polypeptide having midkine modulating activity is administered. In an embodiment the promoter is a tissue preferred promoter such as, but not limited to, a pulmonary tissue preferred promoter or a smooth muscle cell preferred promoter. In an embodiment, the midkine modulating agent alters the HIF-1α/β interaction.

By "alters midkine expression levels" is intended that the expression of the midkine nucleotide sequence in a transgenic cell, transgenic tissue, or transgenic cell or tissue of a transgenic animal of the invention differs from expression levels in a non-transgenic cell, non-transgenic tissue, or a non-transgenic animal by at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100%. The difference may be an increase or decrease in expression levels.

Methods of assaying expression levels are known in the art and include, but are not limited to, qualitative Western blot analysis, immunoprecipitation, radiological assays, polypeptide purification, spectrophotometric analysis, Coomassie staining of acrylamide gels, ELISAs, RT-PCR, 2-D gel electrophoresis, microarray analysis, in situ hybridization, chemiluminescence, silver staining, enzymatic assays, ponceau S staining, multiplex RT-PCR, immunohistochemical assays, radioimmunoassay, colorimetric analysis, immunoradiometric assays, immunochemistry, positron emission tomography, Northern blotting, fluorometric assays, fluorescence activated cell sorter staining of permeabilized cells, radioimmunosorbent assays, real-time PCR, hybridization assays, sandwich immunoassays, flow cytometry, SAGE, differential amplification, or electronic analysis. See, for example, Ausubel et al, eds. (2002) Current Protocols in Molecular Biology, Wiley-Interscience, New York, N.Y.; Coligan et al (2002) Current Protocols in Protein Science, Wiley-Interscience, New York, N.Y.; Sun et al. (2001) *Gene Ther.* 8:1572-1579; de Jager et al. (2003). *Clin. & Diag. Lab. Immun.* 10:133-139; U.S. Pat. Nos. 6,489,4555; 6,551,784; 6,607,879; 4,981,783; and 5,569,584; herein incorporated by reference in their entirety.

An embodiment of the invention is a method of detecting a midkine pathway abnormality. The method comprises obtaining a sample and assaying the midkine expression level in the sample. An increase or decrease in expression level compared to standard midkine expression levels in a similar sample obtained from a healthy subject, either directly or indirectly (for example, a predetermined standard) indicates a midkine pathway abnormality. By "midkine pathway" is intended any pathway that impacts midkine expression, directly or indirectly. A "midkine pathway abnormality" is an alteration in any stage of a midkine pathway that alters midkine expression. Assays for a midkine pathway abnormality include but are not limited to midkine expression assays and midkine promoter expression assays.

Another embodiment provides a method of detecting a pulmonary disorder. The method comprises obtaining a pulmonary tissue sample and assaying the midkine expression levels in the pulmonary tissue sample. By "pulmonary tissue" is intended any tissue obtained from the lungs, including but not limited to, the lungs, bronchi, bronchioles, alveoli, and developmentally related tissues. A tissue is one or more related cells. By "pulmonary smooth muscle cell" is intended any smooth muscle cell associated with pulmonary tissue including, but not limited to, smooth muscle cells associated with bronchial conducting airways and pulmonary arterial cells. By "pulmonary vascular smooth muscle cell" is intended any smooth muscle cell associated with the pulmonary vasculature including, but not limited to, pulmonary vascular cells and their precursors.

Midkine modulating agents include, but are not limited to, midkine, TTF-1, HIF1-α, oxygen, siRNA, anti-sense RNA, midkine binding compounds, midkine receptor binding compounds, and compounds that alter midkine expression such as a HIF 1-α modulating agent. Additional midkine modulating agents may be identified using the methods of the invention.

In several embodiments of the invention, the midkine modulating agent is an isolated nucleic acid molecule comprising an expression cassette. The expression cassette comprises a promoter operably linked to a nucleotide sequence of interest. Nucleotide sequences of interest exhibit a midkine modulating activity or encode a polypeptide having midkine modulating activity. Nucleotide sequences of interest include, but are not limited to, midkine (SEQ ID NO:1; SEQ ID NO:25), thyroid transcription factor-1 (TTF-1; SEQ ID NO:3), and hypoxia inducing factor-1 (HIF-1α; SEQ ID NO: 5), and fragments and variants thereof.

Fragments and variants of the nucleotide sequences of interest and polypeptides encoded thereby are also encompassed by the present invention. Fragments and variants of the modified midkine promoters (discussed elsewhere herein) are also encompassed by the present invention. By "fragment" is intended a portion of the nucleotide sequence or a portion of the amino acid sequence and hence protein encoded thereby. Fragments of a nucleotide sequence may encode protein fragments that retain the biological activity of the native protein and hence exhibit a midkine activity. Fragments of a promoter nucleotide sequence may retain biological activity and drive expression. Alternatively, fragments of a nucleotide sequence that are useful as hybridization probes generally do not retain biological activity. Thus, fragments of a nucleotide sequence may range from at least about 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, up to 881 nucleotides for SEQ ID NO:1; from at least about 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 1050, 1100, up to about 1119 nucleotides for SEQ ID NO:3; from at least about 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350, 3400, 3450, 3500, 3550, 3600, 3650, 3700, 3750, 3800, 3850, 3900, 3950, up to about 3973 nucleotides for SEQ ID NO:5; from at least about 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 1050, 1100, 1150, 1200, 1250, 1300,1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, up to about 2559 nucleotides for SEQ ID NO:7, 11, 12, 13, or 14; from at least about 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, up to about 2074 nucleotides for SEQ ID NO:8, from at least about 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, up to about 1677 nucleotides for SEQ ID NO:9; from at least about 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, up to about 1037 nucleotides for SEQ ID NO:10, from at least about 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, up to about 2566 nucleotides for SEQ ID NO:15 or 16; from at least about 20, 25, 30, 35, 40, 45, 50, 55, 60, 65, 70, 75, 80, 85, 90, 95, 100, 150, 200, 250, 300, 350, 400, 450, 500, 550, 600, 650, up to 695 nucleotides for SEQ ID NO:25.

A fragment of a nucleotide sequence of interest that encodes a biologically active portion of a polypeptide of interest will encode at least 15, 25, 30, 40, 50, 60, 70, 80, 90, 100, 110, 120, 130, or 140 contiguous amino acids, or up to the total number of amino acids present in the full-length protein. Fragments of a nucleotide sequence or interest that are useful as hybridization probes or PCR primers generally need not encode a biologically active portion of a protein.

Thus, a fragment of a nucleotide sequence of interest may encode a biologically active portion of midkine, a midkine promoter, or a midkine modulating agent or it may be a fragment that can be used as a hybridization probe or PCR primer using methods disclosed below. A biologically active portion of a midkine can be prepared by isolating a portion of one of the midkine nucleotide sequences of the invention, expressing the encoded portion of the midkine protein (e.g., by recombinant expression in vitro), and assessing the activity of the encoded portion of the midkine protein. Nucleic acid molecules that are fragments of a midkine nucleotide sequence comprise at least about 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, up to 881 nucleotides for SEQ ID NO:1 or at least about 20, 25, 30, 35, 40, 45, 50, 55, 60, 65, 70, 75, 80, 85, 90, 95, 100, 150, 200, 250, 300, 350, 400, 450, 500, 550, 600, 650, up to 695 nucleotides for SEQ ID NO:25. A biologically active portion of a midkine promoter can be prepared by isolating a portion of the promoter nucleotide sequence disclosed herein, and assessing the activity of the portion of the promoter. Nucleic acid molecules that are fragments of a midkine promoter comprise from at least about 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, up to about 2559 nucleotides for SEQ ID NO:7, 11, 12, 13, or 14; from at least about 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, up to about 2074 nucleotides for SEQ ID NO:8, from at least about 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, up to about 1677 nucleotides for SEQ ID NO:9; from at least about 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, up to about 1037 nucleotides for SEQ ID NO:10, from at least about 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, up to about 2566 nucleotides for SEQ ID NO:15 or 16.

By "variants" is intended substantially similar sequences. For nucleotide sequences, conservative variants include those sequences that, because of the degeneracy of the genetic code, encode the amino acid sequence of one of the midkine polypeptides of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis [but which still encode midkine]. Generally, variants of a particular nucleotide sequence of interest will have at least about 90%, 91%, 92%, 93%, 94%, 95%, 96%, 97%, and more preferably at least about 98%, 99% or more sequence identity to that particular nucleotide sequence as determined by sequence alignment programs described elsewhere herein using default parameters.

By "variant" protein is intended a protein derived from the native protein by deletion (so-called truncation) or addition of one or more amino acids to the N-termial and/or C-terminal end of the native protein; deletion or addition of one or more amino acids at one or more sites in the native protein; or substitution of one or more amino acids at one or more sites in the native protein. Variant proteins encompassed by the present invention are biologically active, that is they continue to possess the desired biological activity of the native protein, that is, a midkine modulating activity as described herein. Such variants may result from, for example, genetic polymorphism or from human manipulation. Biologically active variants of a native midkine modulating protein of the invention will have at least about 90%, 91%, 92%, 93%, 94%, 95%, 96%, 97%, and more preferably at least about 98%, 99% or more sequence identity to the amino acid sequence for the native protein as determined by sequence alignment programs described elsewhere herein using default parameters. A biologically active variant of a protein of the invention may differ from that protein by as few as 1-15 amino acid residues, as few as 1-10, such as 6-10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants of the midkine modulating polypeptides can be prepared by mutations in the DNA. Methods for mutagenesis and nucleotide sequence alterations are well known in the art. See, for example, Kunkel (1985) *Proc. Natl. Acad. Sci. USA* 82:488-492; Kunkel et al. (1987) *Methods in Enzymol.* 154: 367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of protein Sequence and Structure* (Natl. Biomed. Res. Found., Washington, D.C.), herein incorporated by reference. Conservative substitutions, such as exchanging one amino acid with another having similar properties, may be preferable.

Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the midkine modulating activity. Obviously, the mutations that will be made in the DNA encoding the variant must not place the sequence out of reading frame and preferably will not create complementary regions that could produce secondary mRNA structure. See, EP Patent Application Publication No. 75,444.

When it is difficult to predict the exact effect of the substitution, deletion, or insertion in advance of doing so, one skilled in the art will appreciate that the effect will be evaluated by routine screening assays. That is, the activity can be evaluated by suitable assays such as, but not limited to, promoter activity assays or midkine activity assays such as immunogenic activity.

Variant nucleotide sequences also encompass sequences derived from a mutagenic and recombinogenic procedure such as DNA shuffling. With such a procedure, one or more different promoter sequences or nucleotide sequences of interest can be manipulated to create a new sequence possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the modified midkine promoters of the invention and other known promoters to obtain a new promoter with an altered property of interest e.g. altered expression levels or altered midkine activity. Strategies for such DNA shuffling are known in the art. See, for example, Stemmer (1994) *Proc. Natl. Acad. Sci.* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci.* 94:4504-4509; Crameri et al. (1998) *Nature* 391:288-291; Miyazaki (2002) *Nucleic Acids Research* 30:E139-9; Song et al. (2002) *Appl. Environ. Microbiol.* 68:6146-51;

Hayes et al. (2002) *Proc. Natl Acad. Sci.* 99:15926-31; Coco et al. (2001) *Nature Biotechnol.* 19:354-9; Kikuchi et al. (2000) *Gene* 243:133-7; and U.S. Pat. Nos. 5,606,793 and 5,837,458.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence or the complete cDNA or gene sequence.

(b) As used herein "comparison window" makes reference to a contiguous and specified segment of a polynucleotide sequence, wherein the polynucleotide sequence in the comparison window may comprise additions or deletions (i.e. gaps) compared to the reference sequence (which does not comprise additions or deletions) for optimal alignment of the two sequences. Generally the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Preferred, non-limiting examples of such mathematical algorithms are the algorithm of Myers and Miller (1988) *CABIOS* 4:11-17; the local homology algorithm of Smith et al. (1981) *Adv. Appl. Math.* 2:482; the homology alignment algorithm of Needleman and Wunsch (1970) *J. Mol. Biol.* 48:443-453; the search-for-similarity-method of Pearson and Lipman (1988) *Proc. Natl. Acad. Sci.* 85:2444-2448; the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877.

Computer implementations of these mathematical algorithms can be utilized for comparison of sequences to determine sequence identity. For purposes of the present invention, comparison of nucleotide or protein sequences for determination of percent sequence identity to the sequences disclosed herein is preferably made using the GCG program GAP (Version 10.00 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program. Alignment may also be performed manually by inspection.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch (1970) *J. Mol. Biol.* 48:443-453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

For example, an entire promoter sequence or nucleotide sequence of interest disclosed herein, or one or more portions thereof, may be used as a probe capable of specifically hybridizing to corresponding promoter sequences. To achieve specific hybridization under a variety of conditions, such probes include sequences that are unique among the nucleotide sequences of interest or the promoter sequences and are preferably at least about 10 nucleotides in length, and most preferably at least about 20 nucleotides in length. Such probes may be used to amplify corresponding sequences from a chosen animal by PCR. This technique may be used to isolate additional sequences from a desired animal or as a diagnostic assay to determine the presence of the sequences in an animal or animal cell.

In a PCR approach, oligonucleotide primers can be designed for use in PCR reactions to amplify corresponding DNA sequences from cDNA or genomic DNA extracted from any animal of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the nucleotide sequences of interest. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Duration of hybridization is generally less than about 24 hours, usually about 4 to about 12 hours.

Specificity is typically the function of post-hybridization washes, the critical factors being the ionic strength and temperature of the final wash solution. For DNA—DNA hybrids, the $T_m$ can be approximated from the equation of Meinkoth and Wahl (1984) *Anal. Biochem.* 138:267-284: $T_m=81.5°$ C.+16.6 (log M)+0.41 (% GC)-0.61 (% form)-500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with approximately 90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in*

*Molecular Biology*, Chapter 2 (Greene Publishing and Wiley-Interscience, New York). See Sambrook et al. (1989) Molecular Cloning: *A Laboratory Manual* (2d ed., Cold Spring Harbor Laboratory Press, Plainview, N.Y.). Thus, isolated sequences that have midkine modulating activity or promoter activity and which hybridize under stringent conditions to the sequences disclosed herein, or to fragments thereof, are encompassed by the present invention. Such sequences will be at least 85%, 90%, 95% to 98% homologous or more with the disclosed sequences. That is, the sequence identity of sequences may range, sharing at least 85%, 90%, 91%, 92%, 93%, 94%, 95%, 96%, 97%, 98%, 99%, or more sequence identity.

Midkine promoters disclosed in the invention may be isolated from any animal, including but not limited to, rat, hamster, human, rabbit, mouse, monkey, chimpanzee, dog, pig, goat, sheep, cat, and cow. It is recognized that any gene of interest can be operably linked to a promoter of the invention.

As noted, the heterologous nucleotide sequence of interest operably linked to a promoter may be an antisense sequence for a targeted gene (e.g. midkine or a nucleotide sequence encoding a midkine modulating agent). Thus, with these promoters, antisense constructions complementary to at least a portion of the messenger RNA (mRNA) for a targeted nucleotide sequence interest can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence identity to the corresponding antisensed sequences may be used. Furthermore, portions of the antisense nucleotides may be used to disrupt the expression of the target gene. Generally, sequences of at least 50 nucleotides, 100 nucleotides, 200 nucleotides, or greater may be used. Thus, a tissue-preferred promoter sequence may be operably linked to antisense DNA sequences to reduce or inhibit expression of native midkine in a tissue of interest.

By "nucleotide sequence of interest" is intended a sequence that is not naturally occurring with the promoter sequence. While this nucleotide sequence is heterologous to the promoter sequence, it may be homologous, or native, or heterologous, or foreign, to the animal host.

It is recognized that the promoters may be used with their native coding sequences to increase or decrease expression resulting in a change in phenotype in the transformed animal or subject.

A number of promoters can be used in the practice of the invention. The promoters can be selected based on the desired outcome. In various embodiments of the invention, a midkine modulating agent is an isolated nucleic acid molecule comprising an expression cassette comprising a promoter operably linked to a nucleotide sequence of interest.

By "promoter" or "transcriptional initiation region" is intended a regulatory region of DNA usually comprising a TATA box capable of directing RNA polymerase II to initiate RNA synthesis at the appropriate transcription initiation site for a particular coding sequence. A promoter may additionally comprise other recognition sequences generally positioned upstream or 5' to the TATA box, referred to as upstream promoter elements, which influence the transcription initiation rate. It is recognized that having identified the nucleotide sequences for the promoter regions disclosed herein, it is within the state of the art to isolate and identify further regulatory elements in the 5' untranslated region. Thus, the promoter regions disclosed herein are generally further defined by comprising upstream regulatory elements such as those responsible for tissue and temporal expression of the coding sequence, enhancers and the like. Such elements are typically linked via a 5' untranslated region, which may further modulate gene expression, to a coding region of interest. In the same manner, the promoter elements that enable expression in the desired tissue such as pulmonary-tissue or smooth muscle cells can be identified, isolated, and used with other core promoters to confirm tissue-preferred expression. For genes in which the 5' untranslated region does not affect cell specificity, alternative sources of 5' untranslated leaders may be used in conjunction with these promoter elements.

A number of promoters can be used in the practice of the invention. The promoters can be selected based on the desired outcome. Where low level expression is desired, weak promoters will be used. Generally, by "weak promoter" is intended a promoter that drives expression of a coding sequence at a low level. By "low level" is intended at levels of about $1/10,000$ transcripts to about $1/100,000$ transcripts to about $1/500,000$ transcripts; conversely, a strong promoter drives expression of a coding sequence at a high level, or at about $1/10$ transcripts to about $1/100$ transcripts to about $1/1000$ transcripts. Alternatively, it is recognized that weak promoters also encompasses promoters that are expressed in only a few cells and not in others to give a total low level of expression. Where a promoter is expressed at unacceptably high levels, portions of the promoter sequence can be deleted or modified to decrease expression levels.

It is recognized that to increase transcription levels or to alter tissue specificity, enhancers and/or tissue-preference elements may be utilized in combination with the nucleotide sequences of interest. For example, quantitative or tissue specificity upstream elements from other pulmonary tissue-preferred or smooth muscle cell preferred promoters may be combined with the promoter regions of the invention to augment tissue-preferred transcription. The human surfactant protein C promoter is a pulmonary tissue preferred promoter (Perl et al. (2002) *Transgenic Res.* 11:21-29, herein incorporated by reference in its entirety). The murine smooth muscle 22 α (SM22α) promoter is a smooth muscle cell preferred promoter (U.S. Pat. Nos. 6,015,711 and 5,837,534, herein incorporated by reference in their entirety).

In other embodiments, the coding region is operably linked to an inducible regulatory element or elements. A variety of inducible promoter systems have been described in the literature and can be used in the present invention. These include, but are not limited to, tetracycline-regulatable systems (WO 94/29442, WO 96/40892, WO 96/01313, U.S. application Ser. No. 10/613,728); hormone responsive systems, interferon-inducible systems, metal-inducible systems, and heat-inducible systems, (WO 93/20218); and ecdysone inducible systems. Some of these systems, including ecdysone inducible and tetracycline inducible systems are commercially available from Invitrogen (Carlsbad, Calif) and Clontech (Palo Alto, Calif), respectively.

By "inducible" is intended that a chemical stimulus alters expression of the operably linked nucleotide sequence of interest by at least 1%, 5%, preferably 10%, 20%, more preferably 30%, 40%, 50%, 60%, 70%, 80%, 90%, 99% or more. The difference may be an increase or decrease in expression levels. Methods for assaying expression levels are described elsewhere herein. The chemical stimulus may be administered or withdrawn. Various chemical stimuli are known in the art. In an embodiment, the chemical stimulus is tetracycline, or an analog thereof.

One of the most widely used conditional systems is the binary, tetracycline-based system, which has been widely used in both cells and animals to reversibly induce expression by the addition or removal of tetracycline or its analogues (See Bujard (1999). *J. Gene Med.* 1:372-374; Furth, et al. (1994). *Proc. Natl. Acad. Sci. USA* 91:9302-9306; and Mansuy & Bujard (2000). *Curr. Opin. Neurobiol.* 10:593-596, herein incorporated by reference in their entirety.).

Another class of promoter elements includes those which activate transcription of an operably linked nucleotide sequence of interest in response to hypoxic conditions. These include promoter elements regulated at least in part by hypoxia inducible factor-1. Hypoxia response elements include, but are not limited to, the erythropoietin hypoxia response enhancer element (HREE1), the muscle pyruvate kinase HRE; the β-enolase HRE; and endothelin-1 HRE element, and chimeric nucleotide sequence comprising these sequences. See Bunn and Poynton (1996) *Physiol. Rev.* 76:839-885; Dachs and Stratford (1996) *Br. J. Cancer* 74:S126-S132; Guillemon and Krasnow (1997) *Cell* 89:9-12; Firth et al. (1994) *Proc. Natl. Acad. Sci.* 91:6496-6500; Jiang et al. (1997) *Cancer Res.* 57:5328-5335; U.S. Pat. No. 5,834,306) herein incorporated by reference in their entirety.

In an embodiment, the invention provides methods of preferentially modulating midkine activity in a tissue preferred manner (for example, pulmonary tissue or smooth muscle cells). It is recognized that the nucleotide sequence of interest of a midkine modulating agent which is an isolated nucleic acid molecule comprising an expression cassette comprising a nucleotide sequence of interest can be operably linked to any tissue preferred promoter. The tissue preferred promoter allows expression of the nucleotide sequence of interest in a tissue preferred manner. Tissues of particular interest include pulmonary tissue, smooth muscle cells, pulmonary smooth muscle cells, and pulmonary vascular smooth muscle cells.

By "pulmonary tissue-preferred" is intended that expression of the heterologous sequence is most abundant in pulmonary tissue, while some expression may occur in other tissue types, particularly in tissues developmentally related to pulmonary tissue. Pulmonary-preferred expression of a heterologous nucleotide sequence of interest occurs at levels at least 1%, 5%, 10%, 20%, 30%, 40%, 50%, 60%, 70%, 80%, 90%, or 100% greater than expression of the nucleotide sequence of interest in non-pulmonary tissue. By "pulmonary vascular tissue-preferred" is intended that expression of the heterologous sequence is most abundant in pulmonary vascular tissue, while some expression may occur in other tissue types, particularly in tissues developmentally related to pulmonary vascular tissue. Pulmonary vascular-preferred expression of a heterologous nucleotide sequence of interest occurs at levels at least 1%, 5%, 10%, 20%, 30%, 40%, 50%, 60%, 70%, 80%, 90%, or 100% greater than expression of the nucleotide sequence of interest in non-pulmonary vascular tissue. In an embodiment, tissue-preferred expression of a heterologous nucleotide sequence natively expressed in other tissue may be desired. Expression of a heterologous nucleotide sequence from a tissue-preferred promoter may not impact expression of the nucleotide sequence operably linked to its native promoter in other tissues.

By "smooth muscle cell-preferred" is intended that expression of the heterologous sequence is most abundant in smooth muscle cells, while some expression may occur in other cell types. Smooth muscle cell-preferred expression of a nucleotide sequence of interest occurs at levels at least 1%, 5%, 10%, 20%, 30%, 40%, 50%, 60%, 70%, 80%, 90%, or 100% greater than expression of the heterologous nucleotide sequence of interest in non-smooth muscle cells. In an embodiment, smooth muscle cell-preferred expression of a heterologous nucleotide sequence natively expressed in other tissue may be desired. Expression of a heterologous nucleotide sequence from a smooth muscle cell-preferred promoter may not impact expression of the nucleotide sequence operably linked to its native promoter in other tissues.

The invention provides methods of preferentially modulating midkine activity or expression levels in a tissue of interest. In an embodiment, a midkine modulating agent is administered to the tissue of interest. In an embodiment the midkine modulating agent is an isolated nucleic acid molecule comprising an expression cassette comprising a nucleotide sequence of interest operably linked to a tissue preferred promoter.

By "preferentially modulating pulmonary tissue midkine expression levels" is intended that the expression of midkine in a transgenic cell, pulmonary tissue of a transgenic animal of the invention, or pulmonary tissue of a subject administered a midkine modulating agent differs from expression levels in a non-pulmonary transgenic cell or pulmonary tissue of a non-transgenic animal or untreated subject by at least 1%, 5%, preferably 10%, 20%, more preferably 30%, 40%, 50%, 60%, 70%, 80%, 90%, 99%, or more. The difference may be an increase or decrease in expression levels.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

Such expression cassettes will comprise a transcriptional initiation region comprising a promoter nucleotide sequence operably linked to the heterologous nucleotide sequence whose expression is to be controlled by the promoter. Such an expression cassette is provided with at least one restriction site for insertion of the nucleotide sequence to be under the transcriptional regulation of the regulatory regions. The expression cassette may additionally contain selectable marker genes.

The expression cassette will include in the 5'-to-3' direction of transcription, a transcriptional and translational initiation region, and a heterologous nucleotide sequence of interest. In addition to containing sites for transcription initiation and control, expression cassettes can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al. (1989) *Molecular Cloning: A Laboratory Manual* 2nd. ed., Cold Spring Harbor Laboratory Press, Cold Spring Harbor, N.Y.).

The expression cassette comprising a promoter sequence of the present invention operably linked to a heterologous nucleotide sequence or a promoter operably linked to midkine may also contain at least one additional nucleotide sequence for a gene to be co-transformed into the organism. Alternatively, the additional sequence(s) can be provided on another expression cassette.

The regulatory sequences to which the polynucleotides described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

The isolated modified midkine promoter sequences of the present invention can be modified to provide assays for a range of expression levels of a compound of interest or a midkine modulating agent. Thus, less than the entire promoter regions may be utilized and the ability to drive expression retained. However, it is recognized that expression levels of mRNA may be altered and usually decreased with deletions of portions of the promoter sequences. Generally, at least about 20 nucleotides of an isolated promoter sequence will be used to drive expression of a nucleotide sequence. Truncated forms of the midkine promoter sequence may also be used to assay compounds for midkine modulating activity, particularly midkine expression modulating activity.

The invention encompasses isolated or substantially purified nucleic acid or protein compositions. An "isolated" or substantially "purified" nucleic acid molecule, polypeptide, or biologically active portion thereof, is substantially free of other cellular material, or culture medium when produced by recombinant techniques or substantially free of chemical precursors or other chemicals when chemically synthesized. Preferably, an "isolated" nucleic acid molecule is free of sequences (preferably polypeptide encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4kb, 3 kb, 2 kb, 1 kb, 0.5 kb, or 0.1 kb of nucleotide sequences that naturally flank the nucleic acid molecule in genomic DNA of the cell from which the nucleic acid is derived.

The promoters for midkine genes from alternative species may generally be isolated from the 5' untranslated region flanking their respective transcription initiation sites. Methods for isolation of promoter regions are well known in the art. By "isolated" is intended that the promoter sequences have been determined and can be extracted by molecular techniques or synthesized by chemical means. In either instance, the promoter is removed from at least one of its flanking sequences in its native state.

Where appropriate, the heterologous nucleotide sequence whose expression is to be under the control of a promoter sequence and any additional nucleotide sequence(s) may be optimized for increased expression in the transformed animal. That is, these nucleotide sequences can be synthesized using species preferred codons for improved expression, such as rabbit-preferred codons for improved expression in rabbits or mouse-preferred codons in mice. Methods are available in the art for synthesizing species-preferred nucleotide sequences. See, for example, Wada et al. (1992) *Nucleic Acids Res.* 20 (Suppl.), 2111-2118; Butkus et al. (1998) *Clin Exp Pharmacol Physiol Suppl.* 25:S28-33; and Sambrook et al. (1989) *Molecular Cloning: A Laboratory Manual* 2nd. ed., Cold Spring Harbor Laboratory Press, Cold Spring Harbor, N.Y., herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the heterologous nucleotide sequence may be adjusted to levels average for a given cellular host, as calculated by reference to known genes expressed in the host cell. In an embodiment, the sequence is modified to avoid predicted hairpin secondary mRNA structures. In an embodiment the sequence is modified to yield hairpin RNA structures for use in siRNA.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Nat. Acad. Sci. USA* 86:6126-6130); potyvirus leaders, for example, TEV leader (Tobacco Etch Virus) (Allison et al. (1986)); MDMV leader (Maize Dwarf Mosaic Virus) (*Virology* 154:9-20); and human immunoglobulin heavy-chain binding protein (BiP) (Macejak et al (1991) *Nature* 353:90-94). Other methods known to enhance translation and/or mRNA stability can also be utilized, for example, introns, and the like.

In those instances where it is desirable to have the expressed product of the heterologous nucleotide sequence directed to a particular organelle, particularly the mitochondria, the nucleus, the endoplasmic reticulum, the Golgi apparatus; or secreted at the cell's surface or extracellularly; the expression cassette may further comprise a coding sequence for a transit peptide. Such transit peptides are well known in the art and include, but are not limited to, the transit peptide for the acyl carrier protein, the small subunit of RUBISCO, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose; in vitro mutagenesis; primer repair; restriction; annealing; substitutions, for example, transitions and transversions; or any combination thereof may be involved.

Reporter genes or selectable marker genes may be included in the expression cassettes. Examples of suitable reporter genes known in the art can be found in, for example, Ausubel et al. (2002) *Current Protocols in Molecular Biology*. John Wiley & Sons, New York, N.Y., herein incorporated by reference. The reporter utilized in the invention can be any reporter known in the art including, but not limited to, luciferases, blue fluorescent proteins, green fluorescent proteins, CAT, GUS, β-galactosidases, and midkine.

Selectable marker genes for selection of transformed cells or tissues can include genes that confer antibiotic resistance. Examples of suitable selectable marker genes include, but are not limited to, genes encoding resistance to neomycin (Schwartz et al (1991) *Proc. Natl. Acad. Sci.*88:10416-20); chloramphenicol (Herrera Estrella et al. (1983) *EMBO J.* 2:987-992); methotrexate (Herrera Estrella et al. (1983) *Nature* 303:209-213; Meijer et al. (1991) *Plant Mol. Biol.* 16:807-820); hygromycin (Waldron et al. (1985) *Plant Mol. Biol.* 5:103-108; Zhijian et al. (1995) *Plant Science* 108:219-227); streptomycin (Jones et al. (1987) *Mol. Gen. Genet.* 210:86-91); spectinomycin (Bretagne-Sangard et al. (1996) *Transgenic Res.* 5:131-137); bleomycin (Hille et al. (1990) *Plant Mol. Biol.* 7:171-176); sulfonamide (Guerineau et al. (1990) *Plant Mol. Biol.* 15:127-136); puromycin (Abbate et al (2001) *Biotechniques* 31:336-40; cytosine arabinoside (Eliopoulos et al. (2002) *Gene Ther.* 9:452-462); 6-thioguanine (Tucker et al. (1997) *Nucleic Acid Research* 25:3745-46).

Other genes that could serve utility in the recovery of transgenic events but might not be required in the final product would include, but are not limited to, examples such as GUS (b-glucuronidase; Jefferson (1987) *Plant Mol. Biol. Rep.* 5:387); GFP (green fluorescence protein; Wang et al.

(2001) *Anim Biotechnol* 12:101-110; Chalfie et al. (1994) *Science* 263:802), BFP (blue fluorescence protein; Yang et al. (1998) *J. Biol. Chem.* 273:8212-6), CAT; and luciferase (Riggs et al. (1987) *Nucleic Acid Res.* 15 (19):8115; Luchrsen et al. (1992) *Methods Enzymol.* 216: 397-414). These genes are also suitable as reporters when operably linked to a midkine promoter or modified midkine promoter of the invention.

Embodiments of the invention provide methods of screening for a midkine pathway abnormality, screening subjects for a pulmonary disorder, and identifying a midkine modulating agent. In these embodiments, the invention provides isolated nucleic acid molecules comprising an expression cassette comprising a modified midkine promoter of the invention operably linked to a reporter. In the embodiments, the isolated nucleic acid molecule comprising a modified midkine promoter operably linked to a reporter is incubated with a test sample or compound of interest. By test sample is intended a biological sample such as, but not limited to, a subject exhibiting a smooth muscle cell related disorder or pulmonary disorder, cells, cell lysates, cellular fractions, tissues, mucosa, and secretions. In an embodiment, an isolated nucleic acid molecule comprising a modified midkine promoter operably linked to a reporter is transformed into a cell and incubation of the modified midkine promoter with the test sample occurs within the cell. In an embodiment, the isolated nucleic acid molecule is incubated with the test sample in vitro. Methods of assaying reporter expression levels are known in the art and described elsewhere herein. Reporter expression levels are measured by any means known to one skilled in the art.

The invention provides methods of screening subjects for a pulmonary disorder, a smooth muscle cell related disorder, a pulmonary smooth muscle cell related disorder, and a pulmonary vascular smooth muscle cell related disorder. In the methods an isolated nucleic acid molecule comprising a modified midkine promoter operably linked to a reporter is incubated with a test sample obtained from a tissue of interest. Reporter expression levels are measured by any means known to one skilled in the art.

Any of the regulatory or other sequences useful in expression vectors can form part of the transgenic sequence. This includes intronic sequences and polyadenylation signals, if not already included.

Modulation of a midkine activity, smooth muscle cell development, pulmonary development, smooth muscle cell related disorder, pulmonary disorder, a pulmonary smooth muscle cell related disorder, or a pulmonary vascular smooth muscle cell related disorder can be achieved by providing expression of heterologous products or increased expression of endogenous products in a tissue of interest. Alternatively, the results can be achieved by providing for a reduction of expression of one or more endogenous products, particularly enzymes and cofactors in the tissue of interest. These changes result in a change in phenotype of the transgenic animal. For example, a nucleotide sequence of interest can be used to preferentially express midkine in a tissue of interest and alter the midkine expression pattern. In an embodiment, the nucleotide sequence of interest encodes a polypeptide having a midkine modulating activity that alters midkine expression (e.g. TTF-1 and HIF1-α). Alternatively, the promoter is operably linked to a heterologous nucleotide sequence of interest from which antisense mRNA complementary to the coding sequence of a polypeptide of interest can be produced. The antisense RNA inhibits production of the protein or polypeptide of interest. Alternatively, the promoter sequences of the invention can be used to produce small interfering RNAs.

Products of the heterologous nucleotide sequence include structural proteins, enzymes, cofactors, hormones, signaling proteins, and the like.

Nucleotide sequences of interest disclosed in the present invention, as well as variants and fragments thereof, are useful in the genetic manipulation of any animal when operably linked with a promoter capable of initiating transcription in the animal. The midkine sequences are provided in expression cassettes for expression in a transgenic animal of the invention. The cassette will include 5' to 3' regulatory sequences operably linked to a heterologous nucleotide sequence. By "operably linked" is intended the transcription of the nucleotide sequence of interest is under the influence of the promoter sequence. In this manner, promoter nucleotide sequences may be provided in expression cassettes along with nucleotide sequences of interest for expression in the animal of interest, more particularly for tissue-preferred expression in the animal. In an embodiment, heterologous nucleotide sequences of interest suitable for use in the invention include midkine modulating agents including, but not limited to, nucleotide sequences encoding thyroid transcription factor-1 (TTF-1, SEQ ID NO:3), midkine (SEQ ID NO:1, SEQ ID NO:25), hypoxia inducing factor-1 (HIF1-α, SEQ ID NO:5), transcription factors, midkine promoter binding polypeptides, antisense nucleotide sequences, and small interfering RNA (siRNA) sequences. In another embodiment heterologous nucleotide sequences suitable for use in the methods of the invention include nucleotide sequences encoding reporters or reporter genes. Reporters are described elsewhere herein.

By "stably transformed" is intended that the nuclear genome of the animal cell or the nuclear genome of at least one cell of the animal has incorporated at least one copy of the transgene. By "transgene" is intended a nucleic acid molecule having a nucleotide sequence comprising either an expression cassette or a disruption cassette. A transgenic animal of the invention comprises at least one stably transformed cell comprising the nucleotide sequence of interest. In an embodiment, the genome of a germ-line cell of a transgenic animal comprises the nucleotide sequence of interest. A transgenic cell, e.g. a smooth muscle cell, is a cell comprising at least one expression cassette or disruption cassette isolated from a transgenic animal of the invention. Transgenic tissue, e.g. pulmonary tissue and pulmonary smooth muscle cell, is tissue comprising transgenic cells. Transgenic tissue is isolated from a transgenic animal of the invention.

Transgenic animals of the invention are useful for studying the function of midkine and identifying and evaluating modulators of midkine activity, smooth muscle cell development, pulmonary development, smooth muscle cell disorders, pulmonary disorders and pulmonary smooth muscle cell disorders. A transgenic animal is preferably a mammal, for example a mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. A genetically engineered host cell can be used to produce non-human transgenic animals.

Transgenic animals that exhibit altered midkine expression are useful to conduct assays that identify compounds that affect midkine function such as, but not limited to, vascular remodeling. Assays to determine vascular remodeling are known in the art and include, but are not limited to, immunohistochemical analysis and morphometric analysis. The altered midkine expression may result in altered susceptibility to a smooth muscle cell related disorder, pulmonary disorder, or pulmonary smooth muscle cell related disorder.

Methods for generating transgenic animals via embryo manipulation and microinjection, particularly animals such as mice, have become conventional in the art and are described, for example, in U.S. Pat. Nos. 4,736,866; 4,870,009; 4,873,191; 6,201,165 and in Nagy et al Ed. (2003) *Manipulating the Mouse Embryo* Cold Spring Harbor Press, Cold Spring Harbor, N.Y.), herein incorporated by reference in their entirety.

Similar methods are used for production of other transgenic animals. A transgenic animal can be produced by introducing nucleic acid into the male pronuclei of a fertilized oocyte, e.g., by microinjection, retroviral infection, and allowing the oocyte to develop in a pseudopregnant female foster animal. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein. Methods for providing transgenic rabbits are described in Marian et al. (1999) *J. Clin. Invest.* 104:1683-1692 and James et al. (2000) *Circulation* 101:1715-1721, herein incorporated by reference in their entirety.

Other examples of transgenic animals include non-human primates, sheep, dogs, pigs, cows, goats, rats, rabbits, and hamsters.

In an embodiment, the invention provides a method of altering expression of a heterologous midkine nucleotide sequence in an animal, particularly of altering tissue preferred expression of the heterologous nucleotide sequence. In an embodiment the tissue preferred expression is pulmonary tissue preferred expression. In another embodiment, the tissue preferred expression is smooth muscle cell preferred expression. In an embodiment the heterologous nucleotide sequence is operably linked to a tissue preferred promoter. An expression cassette comprising the tissue preferred promoter operably linked to the heterologous nucleotide sequence is used to transform an animal. In an embodiment a tissue preferred promoter is operably linked to a nucleotide sequence encoding a polypeptide that enhances expression from a second promoter. The second promoter is operably linked to a nucleotide sequence encoding midkine (SEQ ID NO:25). Animal transformation methods are known in the art and reviewed elsewhere herein. The method yields a stably transformed transgenic animal exhibiting altered expression of a heterologous nucleotide sequence.

In another embodiment, transgenic non-human animals can be produced which contain selected systems, which allow for regulated expression of the transgene. Examples of such systems include, but are not limited to, the cre/loxP recombinase system, the FLP recombinase system, and the tetracycline based system described elsewhere herein. If a tetracycline based system is used to regulate expression of the transgene, animals containing transgenes encoding both a transactivator and a selected protein are required. Such animals can be provided through the construction of "double" transgenic animals, e.g., by mating two transgenic animals, one containing a transgene encoding a selected protein and the other containing a transgene encoding a transactivator.

Clones of the non-human transgenic animals described herein can also be produced according to the methods described in Wilmut et al. (1997) *Nature* 385:810-813 and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to a pseudopregnant female foster animal. The offspring born of this female foster animal will be a clone of the animal from which the cell, e.g., the somatic cell, is isolated.

In one embodiment, a transgenic animal cell can be a fertilized oocyte or embryonic stem cell that can be used to produce a transgenic animal comprising at least one stably transformed expression cassette comprising the heterologous nucleotide sequence. Alternatively, a transgenic cell can be a stem cell or other early tissue precursor that gives rise to a specific subset of cells and can be used to produce transgenic tissues in an animal. See also Thomas et al., (1987) *Cell* 51:503 for a description of homologous recombination vectors. The vector is introduced into an embryonic stem cell line (e.g., by electroporation) and cells in which the introduced gene has recombined with the genome are selected (see e.g., Li, E. et al. (1992) *Cell* 69:915). The selected cells are then injected into a blastocyst of an animal (e.g., a mouse) to form aggregation chimeras (see e.g., Bradley, A. in Teratocarcinomas and Embryonic Stem Cells: A Practical Approach, E. J. Robertson, ed. (IRL, Oxford, 1987) pp. 113-152). A chimeric embryo can then be implanted into a suitable pseudopregnant female foster animal and the embryo brought to term. Progeny harboring the recombined DNA in their germ cells can be used to breed animals in which all cells of the animal contain the recombined DNA by germ line transmission of the transgene. Methods for constructing homologous recombination vectors and homologous recombinant animals are described further in Bradley, A. (1991) Current Opinion in Biotechnology 2:823-829 and in PCT International Publication Nos. WO 90/11354; WO 91/01140; and WO 93/04169, herein incorporated by reference in their entirety.

Delivery vehicles suitable for incorporation of a polynucleotide for introduction into a host cell include, but are not limited to, viral vectors and non-viral vectors (Verma and Somia (1997) *Nature* 389:239-242).

A wide variety of non-viral vehicles for delivery of a polynucleotide are known in the art and are encompassed in the present invention. An isolated nucleic acid molecule can be delivered to a cell as naked DNA (WO 97/40163). Alternatively, a polynucleotide can be delivered to a cell associated in a variety of ways with a variety of substances (forms of delivery) including, but not limited to, cationic lipids; biocompatible polymers, including natural and synthetic polymers; lipoproteins; polypeptides; polysaccharides; lipopolysaccharides; artificial viral envelopes; metal particles; and bacteria. A delivery vehicle can be a microparticle. Mixtures or conjugates of these various substances can also be used as delivery vehicles. A polynucleotide can be associated non-covalently or covalently with these forms of delivery. Liposomes can be targeted to a particular cell type, e.g., to a smooth muscle cell or a pulmonary cell.

Viral vectors include, but are not limited to, DNA viral vectors such as those based on adenoviruses, herpes simplex virus, poxvirus such as vaccinia virus, and parvoviruses, including adeno-associated virus; and RNA viral vectors, including but not limited to, the retroviral vectors. Retroviral vectors include murine leukemia virus, and lentiviruses such as human immunodeficiency virus. See Naldini et al. (1996) *Science* 272:263-267.

Non-viral delivery vehicles comprising a polynucleotide can be introduced into host cells and/or target cells by any method known in the art, such as transfection by the calcium phosphate co-precipitation technique; electroporation; electropermeablization; liposome-mediated transfection; ballistic transfection; biolistic processes including microparticle bombardment, jet injection, and needle and syringe injection, or by microinjection. Numerous methods of transfection are known to the skilled worker in the field.

Viral delivery vectors can be introduced into cells by infection. Alternatively, viral vectors can be incorporated into any of the non-viral delivery vectors described above for delivery into cells. For example, viral vectors can be mixed with cationic lipids (Hodgson and Solaiman (1996) *Nature Biotechnol.* 14:339-342); or lamellar liposomes (Wilson et al. (1977) *Proc. Natl. Acad. Sci.* 74:3471-3475; and Faller et al. (1984) *J. Virol.* 49:269-272).

For in vivo delivery, the vector can be introduced into an individual or organism by any method known to the skilled artisan.

Transgenic animals that exhibit altered midkine expression of the heterologous nucleotide sequence are useful to conduct assays that identify compounds that modulate midkine activity, smooth muscle cell development, pulmonary development, smooth muscle cell related disorders, pulmonary disorders, and pulmonary smooth muscle cell related disorders. The altered midkine expression may result in altered susceptibility to a pulmonary disorder or a smooth muscle cell related disorder.

Disorders of interest include, but are not limited to, pulmonary disorders, smooth muscle cell related disorders, pulmonary smooth muscle cell related disorders, and pulmonary vascular smooth muscle cell related disorders.

A "pulmonary disorder" is any disorder or condition involving pulmonary tissue. Pulmonary disorders include but are not limited to, pulmonary hypertension, asthma, primary pulmonary hypertension, secondary pulmonary hypertension, pulmonary arterial hyperplasia, hypoxemia, airway hyperactivity, idiopathic pulmonary hypertension, hypertrophy, hyperplasia, pulmonary hypertension secondary to hypoxemia, bronchopulmonary dysplasia, heart disease associated with pulmonary vascular remodeling, lung inflammation associated with pulmonary vascular remodeling, persistent pulmonary hypertension of the newborn, Eisenmenger's complex, congenital anomalies; atelectasis; diseases of vascular origin, such as pulmonary congestion and edema, including hemodynamic pulmonary edema and edema caused by microvascular injury, adult respiratory distress syndrome (diffuse alveolar damage), pulmonary embolism, hemorrhage, and infarction, and pulmonary hypertension and vascular sclerosis; chronic obstructive pulmonary disease, such as emphysema, chronic bronchitis, bronchial asthma, and bronchiectasis; cor pulmonale associated severe pulmonary diseases, such as emphysema and cystic fibrosis; diffuse interstitial (infiltrative, restrictive) diseases, such as pneumoconioses, sarcoidosis, idiopathic pulmonary fibrosis, desquamative interstitial pneumonitis, hypersensitivity pneumonitis, pulmonary eosinophilia (pulmonary infiltration with eosinophilia), Bronchiolitis obliterans-organizing pneumonia, diffuse pulmonary hemorrhage syndromes, including Goodpasture syndrome, idiopathic pulmonary hemosiderosis and other hemorrhagic syndromes, pulmonary involvement in collagen vascular disorders, and pulmonary alveolar proteinosis; bronchopulmonary dysplasia; complications of therapies, such as drug-induced lung disease, radiation-induced lung disease, and lung transplantation; tumors, such as bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma. Secondary pulmonary hypertension is caused by numerous diseases and conditions including emphysema, bronchitis, scleroderma, CREST syndrome, systemic lupus erythematosus, ventricular septal defects, atrial septal defects, chronic pulmonary thromboembolism, HIV infection, liver disease, fenfluramine use and dexfenfluramine use.

Phenotypes associated with pulmonary disorders include, but are not limited to, altered midkine expression levels, dyspnea on exertion, oxygenation levels, tricuspid regurgitation, right ventricular dilation, ventricular hypertrophy, and morphology.

Assays to assess pulmonary disorders or phenotypes associated with pulmonary disorders include, but are not limited to, two-dimensional echocardiography, assessment of oxygenation, pulmonary function testing, high resolution computed tomography of the chest, ventilation-perfusion lung scanning, and cardiac catheterization, electrocardiogram, chest radiography, 2-D echocardiography with Doppler flow studies, arterial blood gas analysis, pulmonary angiography, EIAs, light microscopy, multiplex RT-PCR, positron emission tomography, MRI, pulmonary ultrasound, and hematoxylin and eosin staining.

A "smooth muscle cell related disorder" is any disorder or condition involving smooth muscle cells including, but not limited to, smooth muscle cell proliferation, smooth muscle cell differentiation, asthma, airway hyperactivity, idiopathic pulmonary hypertension, pulmonary hypertension secondary to hypoxemia, and heart disease or lung inflammation that is associated with pulmonary vascular remodeling and pulmonary hypertension.

Phenotypes associated with smooth muscle cell related disorders include, but are not limited to, percent actinization, distal pulmonary vessel counts, angiogenic activity, and midkine expression.

Assays to assess smooth muscle cell related disorders include but are not limited to actin staining, morphometric analysis, and midkine expression analysis.

A "pulmonary smooth muscle related disorder" is any disorder or condition involving smooth muscle cells in pulmonary tissue including, but not limited to, smooth muscle cell proliferation, smooth muscle cell differentiation, asthma, airway hyperactivity, idiopathic pulmonary hypertension, pulmonary hypertension secondary to hypoxemia, heart disease or lung inflammation that is associated with pulmonary vascular remodeling and pulmonary hypertension. Pulmonary smooth muscle related disorders and phenotypes associated with pulmonary smooth muscle related disorders may be assayed by any means known to one skilled in the art, including but not limited to, the smooth muscle cell related disorder assays and the pulmonary disorder assays.

In various embodiments, the invention provides methods of modulating a pulmonary disorder, smooth muscle cell related disorder, a pulmonary smooth cell related disorder, or a pulmonary vascular smooth muscle cell related disorder. The methods comprise the steps of identifying a subject exhibiting the disorder of interest and administering a midkine modulating agent to the subject. In an embodiment a clinician identifies a subject of interest based on a physical examination, a potential subject's description of the symptoms, or review of a description of the potential subject's symptoms; or a potential subject correlates his symptom or symptoms with a description of the symptoms associated with a disorder of interest. The midkine modulating agent may increase or decrease the one or more symptoms associated with the disorder. In an embodiment, the midkine modulating agent is administered directly to the tissue of interest. In an embodiment, a cell in the tissue of interest is transformed with an isolated nucleic acid molecule comprising an expression cassette comprising a promoter operably linked to a nucleotide sequence of interest. Promoters and nucleotide sequences of interest are discussed elsewhere herein. In various aspects, the midkine modulating agent functions by binding midkine, binding a midkine receptor, or altering midkine expression levels; the invention is not limited by the midkine modulating agents' method of function. A midkine modulating agent may function by altering HIF1-α expression, HIF-1α/β binding, nuclear localization, or other HIF-1α activity.

By "subject" is intended a mammal, e.g., a human, or an experimental or animal or disease model or mammalian tissue or mammalian cells. Suitable subjects include mammals, particularly humans, exhibiting a pulmonary disorder, a smooth muscle cell related disorder, or a pulmonary smooth muscle cell related disorder; tissue obtained from a mammal exhibiting a exhibiting a pulmonary disorder, a smooth muscle cell related disorder, or a pulmonary smooth muscle cell related disorder; cells obtained from a mammal exhibiting a exhibiting a pulmonary disorder, a smooth muscle cell related disorder, or a pulmonary smooth muscle cell related disorder; and cells cultured from a mammal exhibiting a exhibiting a pulmonary disorder, a smooth muscle cell related disorder, or a pulmonary smooth muscle cell related disorder. The subject can also be a non-human mammal such as, but not limited to, a horse, hamster, guinea pig, mouse, rabbit, dog, pig, goat, cow, rat, monkey, chimpanzee, sheep, or other domestic animal.

By "altered susceptibility" is intended that a transgenic animal of the invention differs from a non-transgenic animal in the extent to which the transgenic animal of the invention exhibits a pulmonary disorder associated phenotype, smooth muscle cell disorder related phenotype, or a pulmonary smooth muscle cell related disorder phenotype. The disorder phenotype may present during any stage of development including, but not limited to, embryonically, post-natally, in the adult, and as the animal nears end of lifespan. In an embodiment, the disorder phenotype may be induced by external stimuli such as, but not limited to, diet, exercise, chemical treatment, or surgical procedure.

In an embodiment, a transgenic animal or cell of the invention may be used to identify midkine modulating agents. To identify midkine modulating agent, multiple transgenic animals of the invention, e.g. at least a first and second transgenic animal, are provided. The terms "first," "experimental," or "test" transgenic animal refer to a transgenic animal to which a compound of interest is administered. The terms "second" or "control" transgenic animal refer to a transgenic animal to which a placebo is administered. In an embodiment, the first and second transgenic animals are clonal, age-matched, gender-matched, and subject to similar environmental conditions. In an embodiment, more than one animal may be a first transgenic animal. In an embodiment more than one animal may be a second transgenic animal.

After administration of either the compound of interest or the placebo, the first and second transgenic animals are incubated for a period of time. The period of time will have a predetermined duration appropriate to analysis of the phenotype. Such durations include, but are not limited to, 30 seconds; 1, 5, 10, 30, or 60 minutes; 8, 12, 24, 36,or 48hours; 3, 4, 5, 6, or 7 days; 2, 3, or 4 weeks; 2, 3, 4, 5, 6, 7, 8, 9, 10, 11, or 12 months; up to 3 years. Monitoring of a midkine activity may occur continuously; at a single interval; or at multiple intervals, such as, but not limited to, hourly, daily, weekly, and monthly. Any method of assaying a midkine activity known in the art may be used to monitor the effects of the compound of interest on a transgenic animal of the invention.

In an embodiment, the midkine promoter and the modified midkine promoters of the invention are used to identify a midkine modulating agent. An isolated nucleic acid molecule comprising an expression cassette comprising a midkine promoter or a modified midkine promoter operably linked to a reporter is provided. The isolated nucleic acid molecule is incubated with a compound of interest, and the reporter is assayed. Suitable reporters are described elsewhere herein. The period of time will have a predetermined duration appropriate to analysis of the phenotype. Such durations include, but are not limited to, 30 seconds; 1, 5, 10, 30, or 60 minutes; 8, 12, 24, 36, or 48 hours; 3, 4, 5, 6, or 7 days; 2, 3, or 4 weeks; 2, 3, 4, 5, 6, 7, 8, 9, 10, 11, or 12 months; up to 3 years. Monitoring of a midkine activity may occur continuously; at a single interval; or at multiple intervals, such as, but not limited to, hourly, daily, weekly, and monthly. Any method of assaying a reporter activity known in the art may be used to monitor the effects of the compound of interest.

In an embodiment, a transgenic animal of the invention may be used to identify pulmonary disorder modulating agents, smooth muscle cell related disorder modulating agents, pulmonary smooth muscle cell related disorder modulating agents, pulmonary development modulating agents, smooth muscle cell development modulating agents, and pulmonary smooth muscle cell development modulating agents. A "disorder modulating agent" is a compound that modulates a phenotype associated with a disorder of interest. A "development modulating agent" is a compound that modulates a phenotype associated with development of a tissue of interest. Modulation may be an increase or decrease in the phenotype. A modulating agent will modulate a development or disorder associated phenotype by at least 1%, 5%, preferably 10%, 20%, more preferably 30%, 40%, 50%, 60%, yet more preferably 70%, 80%, 90%, or 100% as compared to an untreated or placebo treatment effect. Methods for assaying development and disorder associated phenotypes are described elsewhere herein. Any method of assaying a development or disorder of interest associated phenotype known in the art may be used to monitor the effects of the compound of interest on a transgenic animal of the invention.

To identify modulating agents, multiple transgenic animals of the invention, e.g. at least a first and second transgenic animal, are provided. The terms "first," "experimental," or "test " transgenic animal refer to a transgenic animal to which a compound of interest is administered. The terms "second" or "control" transgenic animal refer to a transgenic animal to which a placebo is administered. In an embodiment, the first and second transgenic animals are clonal, age-matched, gender-matched, and subject to similar environmental conditions. In an embodiment, more than one animal may be a first transgenic animal. In an embodiment more than one animal may be a second transgenic animal.

After administration of either the compound of interest or the placebo, the first and second transgenic animals are incubated for a period of time. Compounds of particular interest are midkine modulating agents. The period of time will have a predetermined duration appropriate to analysis of the phenotype. Such durations include, but are not limited to, 30 seconds; 1, 5, 10, 30, or 60 minutes; 8, 12, 24, 36, or 48 hours; 3, 4, 5, 6, or 7 days; 2, 3, or 4 weeks; 2, 3, 4, 5, 6, 7, 8, 9, 10, 11, or 12 months; up to 3 years. Monitoring of a development or disorder associated phenotype may occur continuously; at a single interval; or at multiple intervals, such as, but not limited to, hourly, daily, weekly, and monthly. Any method of assaying a development or disorder associated phenotype known in the art may be used to monitor the effects of the compound of interest on a transgenic animal of the invention.

By "development associated phenotype" is intended any phenotype associated with the development of a cell or tissue of interest. Development associated phenotypes include, but are not limited to, cell surface marker expression, proliferation, differentiation, cellular morphology, tissue morphology, percent actinization, percent muscularization, pulmonary arterial hyperplasia, α-smooth muscle actin expression, platelet-endothelial cell adhesion molecule expression, vessel formation, expression of cell or tissue specific polypeptides, and air vessel formation.

Development associated phenotype assays include, but are not limited to, scanning electron microscopy, light microscopy, hematoxylin and eosin staining, immunostaining, gross dissection, antibody reactivity, expression pattern analysis, in situ hybridization, FACS analysis, and confocal microscopy.

By "smooth muscle cell development associated phenotype" is intended any phenotype associated with the development of smooth muscle cells including, but not limited to, differentiation, proliferation, cellular morphology, percent actinization, percent muscularization, a-smooth muscle actin expression, and expression of smooth muscle cell-specific markers (Glukhova et al (1991) *Am. J. Physiol.* 261:78-80; Frid et al (1992) *Dev. Biol.* 153:185-193; herein incorporated by reference).

By "pulmonary development associated phenotype" is intended any phenotype associated with pulmonary tissue or pulmonary cells including but not limited to, cell surface marker expression, expression of pulmonary specific markers, tissue morphology, proliferation, differentiation, cellular morphology, percent muscularization, percent vascularization, pulmonary arterial hyperplasia, vessel formation, and pulmonary phenotypes discussed elsewhere herein.

An embodiment of the invention provides methods of modulating smooth muscle development, particularly pulmonary smooth muscle development. The method comprises the step of administering a midkine modulating agent to a mammal. Modulation of smooth muscle development can be assayed by monitoring a development associated phenotype. In an embodiment, the smooth muscle development associated phenotype that is altered is proliferation. In an embodiment, the smooth muscle development associated phenotype that is altered is differentiation. Administration of a midkine modulating agent increases or decreases the development associated phenotype. By "proliferation" is intended a mitotic increase in cell number or an increase in the average size of the cell. By "differentiation" is intended the progression of a pluripotent cell to a cell type from which fewer cell types can emerge.

The term "administer" is used in its broadest sense and includes any method of introducing a compound into a transgenic animal of the present invention. This includes producing polypeptides or polynucleotides in vivo as by transcription or translation in vivo of polynucleotides that have been exogenously introduced into a subject. Thus, polypeptides or nucleic acids produced in the subject from the exogenous compositions are encompassed in the term "administer."

A "compound" comprises, but is not limited to, nucleic acid molecules, small interfering RNAs, peptides, polypeptides, small molecules, glycoproteins, chemokine receptor inhibitors, antisense nucleotide sequences, peptidomimetics, lipids, antibodies, receptor inhibitors, ligands, sterols, steroids, hormones, kinases, kinase inhibitors, agonists, antagonists, ion-channel modulators, diuretics, enzymes, enzyme inhibitors, carbohydrates, deaminases, deaminase inhibitors, G-proteins, G-protein receptor inhibitors, calcium channel modulators, hormone receptor modulators, alcohols, phosphatases, lactones, neurotransmitter inhibitors, angiotensin converting enzyme inhibitors, vasodilators, anticoagulants, neurotransmitter receptor modulators, negative inotropic agents, β-blockers, $Ca^{2+}$ antagonists, anti-arrhythmia agents, vasodilators, midkine promoter binding agents, transcription factors, TTF-1, and HIF-1α. A compound may additionally comprise a pharmaceutically acceptable carrier.

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions. A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELTM (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a carboxypeptidase protein or anti-carboxypeptidase antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For oral administration, the agent can be contained in enteric forms to survive the stomach or further coated or mixed to be released in a particular region of the GI tract by known methods. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer. Compounds may also be delivered with supplemental oxygen administered to a subject.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. "Dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Midkine modulating agents identified by the methods of this invention may be used in the treatment of human individuals. Embodiments of the invention provide methods of treating a pulmonary disorder, a smooth muscle cell related disorder, and a pulmonary smooth muscle cell related disorder. The methods comprise -administering a therapeutically effective amount of a midkine modulating agent to a subject exhibiting a disorder of interest. In an embodiment at least one cell of a tissue of interest is transformed with an isolated nucleic acid molecule comprising an expression cassette comprising a promoter operably linked to a nucleotide sequence of interest. In an aspect, the promoter is a tissue-preferred promoter. Midkine modulating agents useful in the treatment of a disorder discussed herein are provided in therapeutically effective amounts. By "therapeutically effective amounts" is intended an amount sufficient to modulate the desired response. Appropriate therapeutically effective amounts vary depending upon the actual midkine modulating agent utilized, the delivery mode, and the agent's mode of action.

The following examples are offered by way of illustration and not limitation.

EXPERIMENTAL

EXAMPLE 1

Tissue Preparation

Mice were sacrificed by an intraperitoneal injection of a ketamine, xylazine, and acepromazine cocktail and exsanguinated by severing the inferior vena cava and descending aorta. Midline sternotomies were performed. Lungs were inflation fixed with 4% paraformaldehyde in PBS and stored in identical fixative at 4° C. Tissues were washed in PBS, dehydrated in a series of alcohols, and embedded in paraffin. Blocks were sectioned into 5 µm sections using standard techniques. Prior to immunohistochemical staining, the sections were deparaffinized and rehydrated.

EXAMPLE 2

Immunohistochemical Analysis of Midkine, Clara Cell Secretory Protein (CCSP), and Platelet-Endothelial Cell Adhesion Molecule (PECAM)-1

Rehydrated tissue sections were treated with 3% hydrogen peroxide in methanol for 15 minutes. The sections were incubated with 2.5% horse serum in 0.1% TBS for 2 hours at room temperature. The sections were incubated with midkine, CCSP, or PECAM-1 primary antibody at 4° C. overnight at appropriate dilutions. Control sections were incubated overnight at 4° C. in blocking serum alone. The midkine primary antibody was an affinity-purified goat polyclonal antibody targeted to the carboxy-terminus of midkine (Santa Cruz Biotechnology, Inc. Santa Cruz Calif.). Additional commercially available midkine antibodies include, but are not limited to, AF-258-PB, Lot WE02 (R&D Systems Inc.). The anti-CCSP antibody was a goat polyclonal antibody targeted to recombinant mouse CCSP. The PECAM-1 primary antibody was monoclonal rat anti-mouse platelet-endothelial cell adhesion molecule antibody obtained from Pharmigen, San Diego, Calif.

After application of primary antibody, sections were developed with a biotinylated horse anti-goat secondary antibody and a Vector Elite ABC kit (Vector Laboratories; Burlingame Calif.). Development in NiDAB was followed by incubation with Tris-cobalt and counterstaining with nuclear fast red.

The sections were then dehydrated in an increasing series of ethanols, washed in three changes of xylene, and mounted under coverslips with Permount®. Colocalization was determined by analyzing serial sections to compare immunolabeling of the various polypeptides.

EXAMPLE 3

Immunohistochemical Analysis of Pro-surfactant Protein (ProSP-C) and $T_1\alpha$ Rehydrated tissue sections were treated with 3% hydrogen peroxide in methanol for 15 minutes. The sections were incubated with 4% goat serum in 0.1% TBS for 2 hours at room temperature. The sections were incubated with ProSP-C and $T_1\alpha$ primary antibody at 4° C. overnight at appropriate dilutions. Control sections were incubated overnight at 4° C. in blocking serum alone. The ProSP-C primary antibody was a rabbit polyclonal antibody targeted to the first 35 residues of the amino terminus of the human SPC pro protein (ChemiCon, Inc. AB 34.28); this antibody detects the proSP-C polypeptide in mouse lung tissue. The $T_1\alpha$ primary antibody was monoclonal hamster anti-mouse $T_1\alpha$ antibody (The Developmental Studies Hybridoma Bank, University of Iowa; see Farr et al. (1992) *J. Histochem Cytochem* 40:651-664, herein incorporated by reference in its entirety).

After application of primary antibody, sections were developed with a biotinylated goat anti-rabbit secondary antibody and a Vector Elite ABC kit (Vector Laboratories; Burlingame Calif.). Development in NiDAB was followed by incubation with Tris-cobalt and counterstaining with nuclear fast red.

Figure 6:
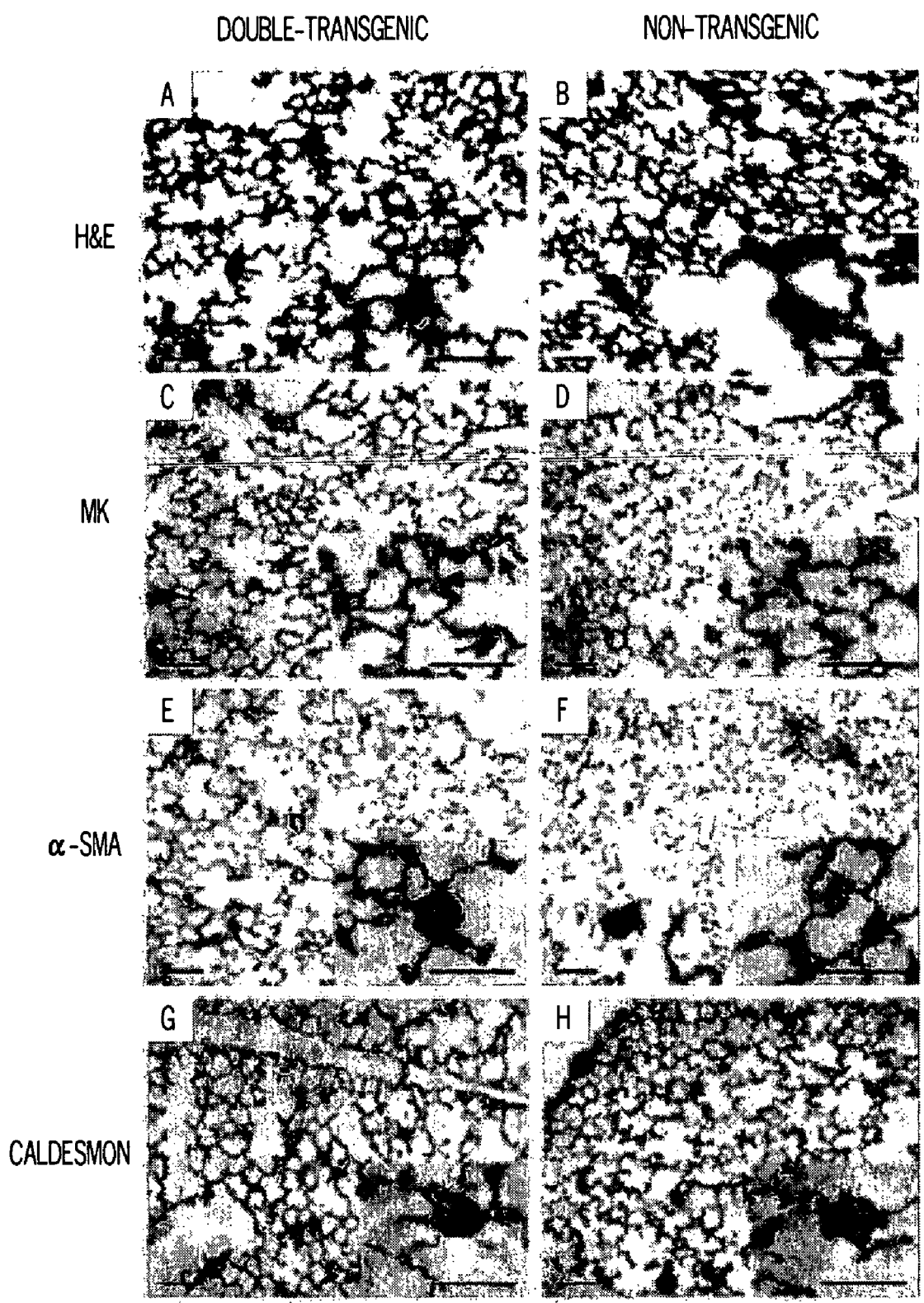
FIG. 6 presents histology and immunohistochemical results from pulmonary tissue of double transgenic mice and wild type mice for comparison. Tissue from wild-type mice (Non-transgenic) is presented in the right column; tissue from SP-C-rtTa$^{+/tg}$, (tetO)$_7$-CMV-MK$^{+/tg\ or\ tg/tg}$ mice (Double-transgenic) is presented in the left column. The tissue sections in panels A and B were stained with hematoxylin and eosin. The tissue sections in panels C and D were incubated with anti-midkine antibodies (anti-MK). The tissue sections in panels E and F were incubated with anti-α smooth muscle actin antibodies (anti-α-SMA). The tissue sections in panels G and H were incubated with anti-Caldesmon antibodies (anti-Caldesmon). The bar indicates 50 μm.
Figure 9:
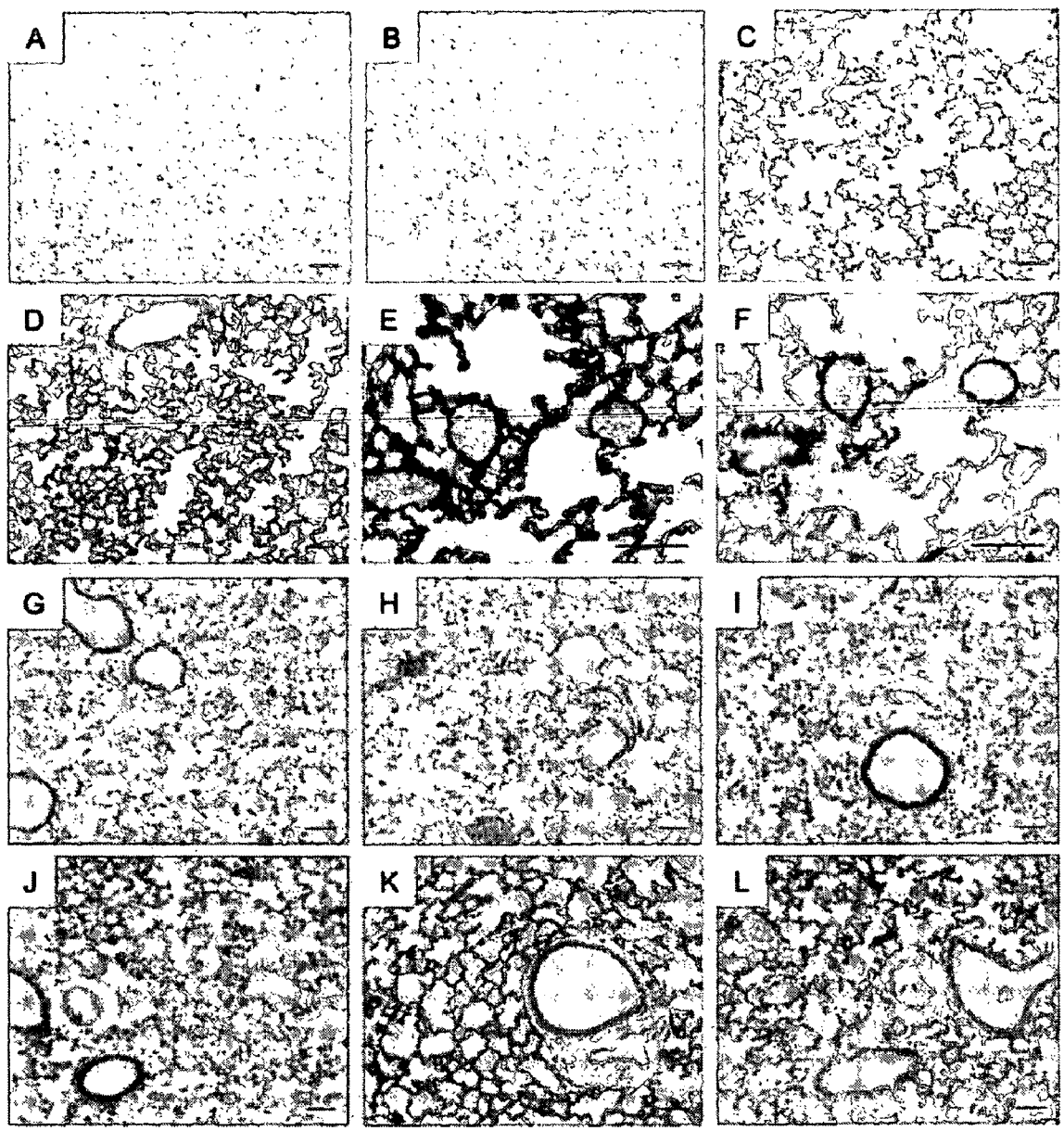
FIG. 9 presents immunohistochemical results from pulmonary tissue of FVB/N and CAST/eiJ mice. Panel A and Panel B present midkine staining of FVB/N pulmonary tissue after exposure to normoxia (A) and hypoxia (B) for five weeks. Panel C and Panel D present midkine staining of CAST/eiJ pulmonary tissue after exposure to normoxia (C) and hypoxia (D) for five weeks. Panels E and F present midkine (E) and α-SMA (F) staining of CAST/eiJ pulmonary tissue after exposure to hypoxia for four weeks. Panels G, H, I, J, K, and L present midkine staining of CAST/eiJ pulmonary tissue after exposure to hypoxia for 1 day (G), 3 days (H), 1 week (I), 2 weeks (J), 3 weeks (K), and 4 weeks (L). Images are at 40× (Panels A-D, G-L) and 100× (Panels E-F). The bar indicates 100 μM.

The sections were then dehydrated in an increasing series of ethanols, washed in three changes of xylene, and mounted under coverslips with Permount®. Colocalization was determined by analyzing serial sections to compare immunolabeling of the various polypeptides. Results from such experiments are presented in FIGS. 6 and 9.

EXAMPLE 4

Immunohistochemical Analysis of α-smooth Muscle Actin (αSMA) and Caldesmon

Rehydrated tissue sections were treated with 3% hydrogen peroxide in methanol for 15 minutes. Inmmunohistochemistry was performed as outlined in the Mouse on Mouse (M.O.M.) monoclonal kit obtained from the manufacturer (Vector Laboratories, Burlingame Calif.). The sections were incubated with blocking serum for one hour at room temperature. The sections were incubated with αSMA or caldesmon primary antibody at appropriate dilutions for 30 minutes. Control sections were incubated with blocking serum alone.

After application of primary antibody, sections were developed with a biotinylated mouse secondary antibody and a Vector Elite ABC kit (Vector Laboratories; Burlingame Calif.). Development in NiDAB was followed by incubation with Tris-cobalt and counterstaining with nuclear fast red.

The sections were then dehydrated in an increasing series of ethanols, washed in three changes of xylene, and mounted under coverslips with Permount®. Colocalization was determined by analyzing serial sections to compare immunolabeling of the various polypeptides. Results from such experiments are presented in FIGS. 6 and 9.

EXAMPLE 5

Immunohistochemical Analysis of Midkine Expression in TTF-1 Null Mice

Figure 1B:
FIG. 1 presents the results of immunostaining for midkine in mouse lung tissue. The tissue in Panel A is from a TTF-1 null mouse embryo. For comparison, the tissue in Panel B is from a wild-type littermate embryo. In Panel A, the esophagus is indicated with an arrow and the vertebral column is indicated with an arrowhead.
Figure 1A:
Figure 2A:
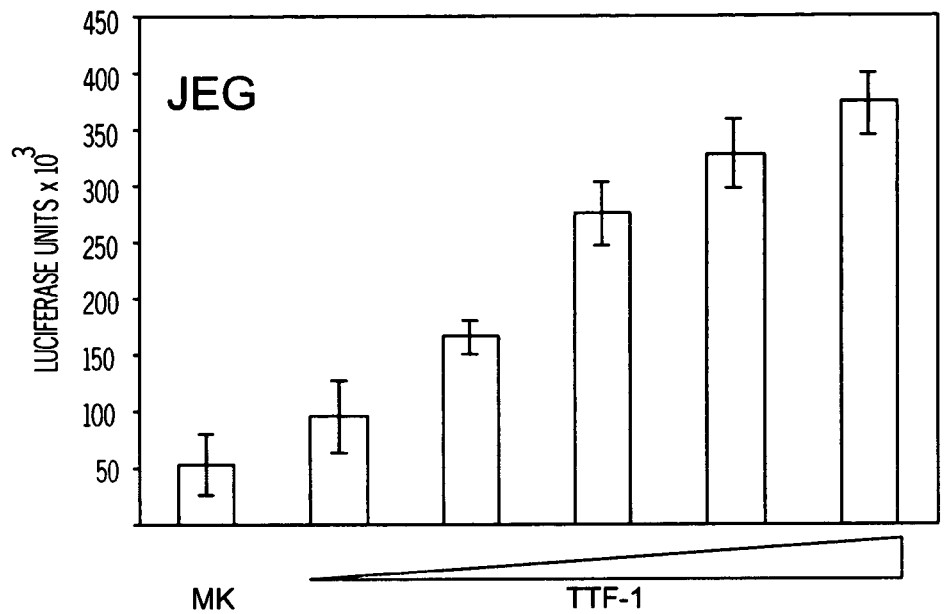
FIG. 2 depicts the results obtained from a midkine promoter activity assay. The expression constructs contained the midkine promoter (SEQ ID NO:7) operably linked to a luciferase reporter gene. The results in Panel A were obtained from JEG cells. JEG is a transformed human placental cell line with significantly reduced TTF-1 expression. The results in Panel B were obtained from H-441 cells. The H-441 cell line is a human epithelial cell line expressing TTF-1. Increasing amounts (0 to 500 ng) of a pCMV-TTF-1 expression plasmid were transfected into the cells.
Figure 2B:
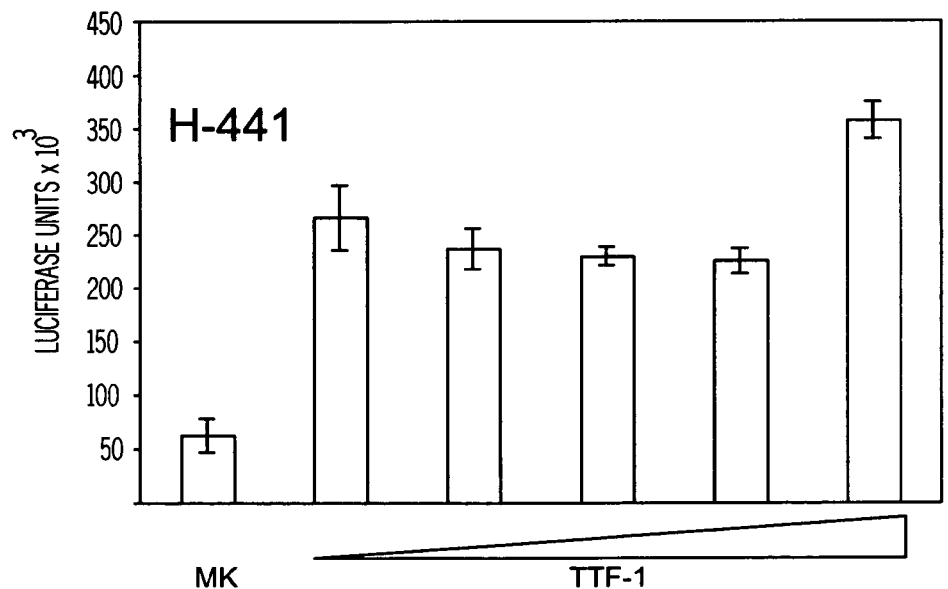

TTF-1 null transgenic mice were bred and maintained as previously described (Kimura et al. (1996) *Genes Dev.* 10:60-69, Wert et al. (2002) *Developmental Biol.* 242:75-87; herein incorporated by reference in their entirety). Sections of the TTF-1 null mice were prepared as described elsewhere herein. Immunohistochemical analysis of midkine expression was performed on the sections as described elsewhere herein. Results from such an experiment are presented in FIG. 1.

EXAMPLE 6

Northern Blot Analysis of Midkine Expression

Total RNA was isolated from lung tissue using Trizol® Reagent and according to the manufacturer's recommended protocol (Invitrogen, Carlsbad Calif.). RNA was stored at −80° C. until further analysis. Northern blot analyses were performed as described in Wikenheiser et al. (1993) *Proc. Natl. Acad. Sci* 90:11029-11033, herein incorporated by reference, with the following modifications. Ten micrograms of total RNA was electrophoresed through 1% agarose/18% formaldehyde gels and transferred to Hybond-N membranes (Amersham, Arlington Heights Ill). The membranes were exposed to UV light.

Figure 5B:
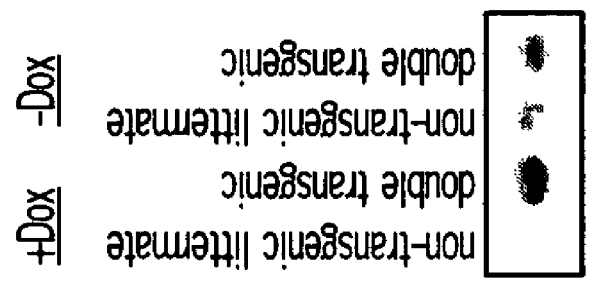
FIG. 5, panel A depicts a schematic of the pulmonary tissue preferred midkine expression system used in the transgenic mice of the invention. The box labeled hSPC indicates the human surfactant protein C promoter operably linked to the reverse tetracycline transactivator cDNA (rtTA, striped box). rtTA molecules are indicated by rectangles overlayed with triangles. Tetracycline-like molecules are indicated by speckled triangles (Dox). Activated rtTA molecules are indicated by a combination of the rtTA shapes and tetracycline-like molecule speckled triangles. The tetO-MK transgene consists of the murine midkine cDNA (SEQ ID NO:25, white box) operably linked to the minimal cytomegalovirus (CMV) promoter containing seven concatemerized tetracycline operon binding sites (rectangles overlayed with speckled triangles). Midkine molecules are depicted as white ovals labeled MK.
Figure 5A:
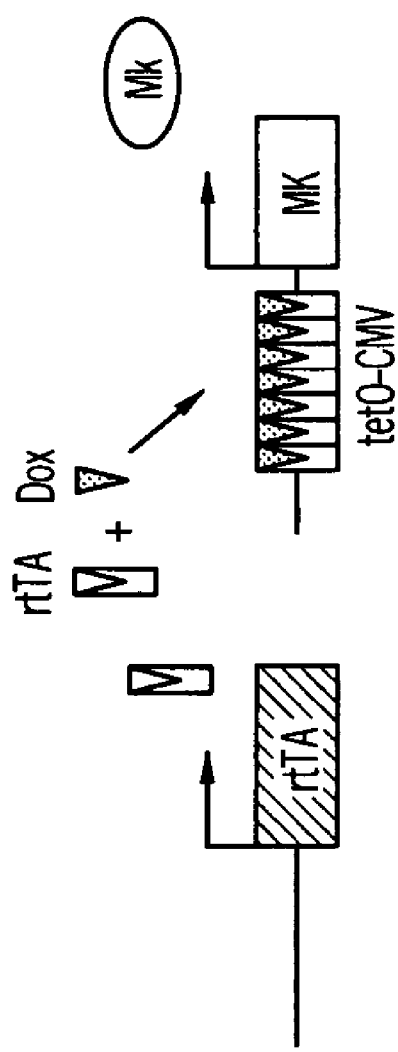

$\alpha^{12}P$ labeled DNA probes were generated using the StripEZ™ DNA kit (Ambion, Austin Tex.). The midkine probe was derived from the 881 base pair mouse cDNA (accession number:AA163237, SEQ ID NO:1) cloned into the pT3T7-Pac vector. The membranes were sequentially hybridized with $\alpha^{32}P$ labeled DNA probes in hybridization buffer (0.5 M phosphate buffer, pH 7.2, 3.5% SDS, 33% formamide, 1 mg/ml BSA, 1 mM EDTA, 20 mg/ml yeast tRNA) at 55° C. overnight. The Hybond-N membranes were washed in 2×SSC, 0.1 % SDS at room temperature twice for 30 minutes, then in 0.2×SSC, 0.1% SDS twice for one hour at 55° C. The blots were exposed to X-AR film with an intensifying screen and stored at −80° C. Results from one such experiment are presented in FIG. 5.

EXAMPLE 7

In Situ Hybridization of Midkine

Mouse midkine cDNA was incubated with EcoR1 and Not1 to yield an 881 base pair fragment (SEQ ID NO:1). The EcoR1/Not1 fragment was ligated into the pGEM-11f(+) plasmid (Promega, Madison Wis.) using methods known to one skilled in the art. $^{35}$S-UTP labeled single-stranded sense and anti-sense RNA probes were prepared with a T7/SP6 Riboprobe® Combination System and using the manufacturer's recommended protocol (Promega, Madison, Wis.). The labeled probes were precipitated with ethanol and resuspended in 100 nm dithiothreitol. The probes were diluted in hybridization solution (60% deionized formamide, 20 mM Tris-HCl, 5 mM EDTA pH 8.0, 0.3 M NaCl, 1× Denhardt's solution, 0.5 mg/ml yeast RNA, and 10% dextran sulfate).

In situ hybridization was performed according to the method of Wilkinson and Green (1990) *Postimplantation Mammalian Embryos* (ed. A. J. Copp and D. L. Cockroft) London: Oxford University Press, pp. 155-171, herein incorporated by reference in its entirety). Slides were immersed in 50% Ilford K5 nuclear track emulsion in 0.3 M ammonium acetate, dried, and exposed to autoradiography film for 7-21 days at 4° C. Hybridization was visualized after development of the slides with Kodak D19 developer at 16° C. After development, sections were examined and photographed under phase optic and dark field illumination.

EXAMPLE 8

Figure 3A:
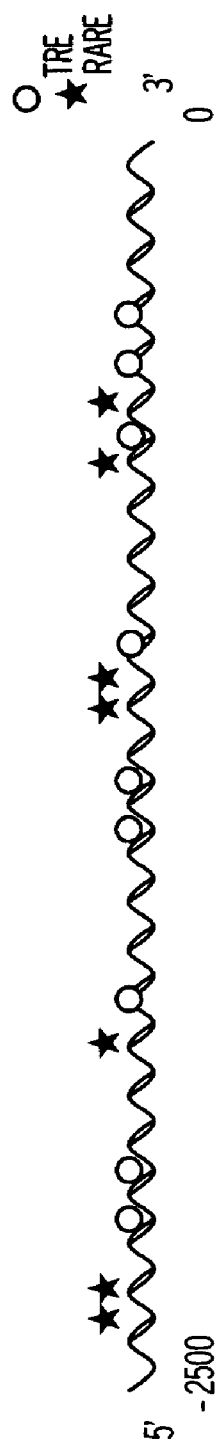
FIG. 3 depicts the wild-type mouse midkine promoter (Panel A), a series of modified midkine promoter-reporter constructs (Panel B), and the results obtained from promoter assays (Panel C). In panel A, circles represent potential TTF-1 responsive elements (TREs), and stars represent consensus retinoic acid receptor sites. The modified midkine promoter sequences represented by the diagram in panel B are provided as SEQ ID NO:7, SEQ ID NO:8, SEQ ID NO:9, and SEQ ID NO:10. The promoters were operably linked to a luciferase reporter gene. The promoter assays presented in panel C were performed in JEG cells in the presence (300) or absence (0) of pCMV-TTF-1. The assays were performed using the full length midkine promoter (SEQ ID NO:7), and the deletion constructs (2.0 kb SEQ ID NO:8, 1.7 kb SEQ ID NO:9, and 1.0 kb SEQ ID NO:10).
Figure 3B:
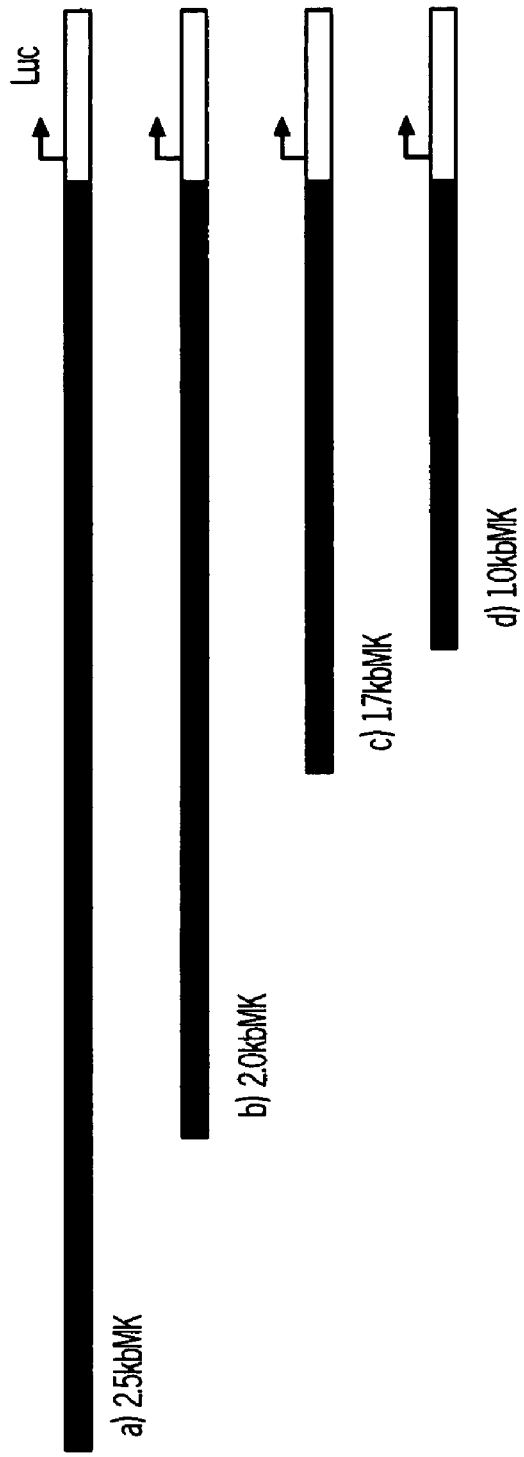
Figure 3C:
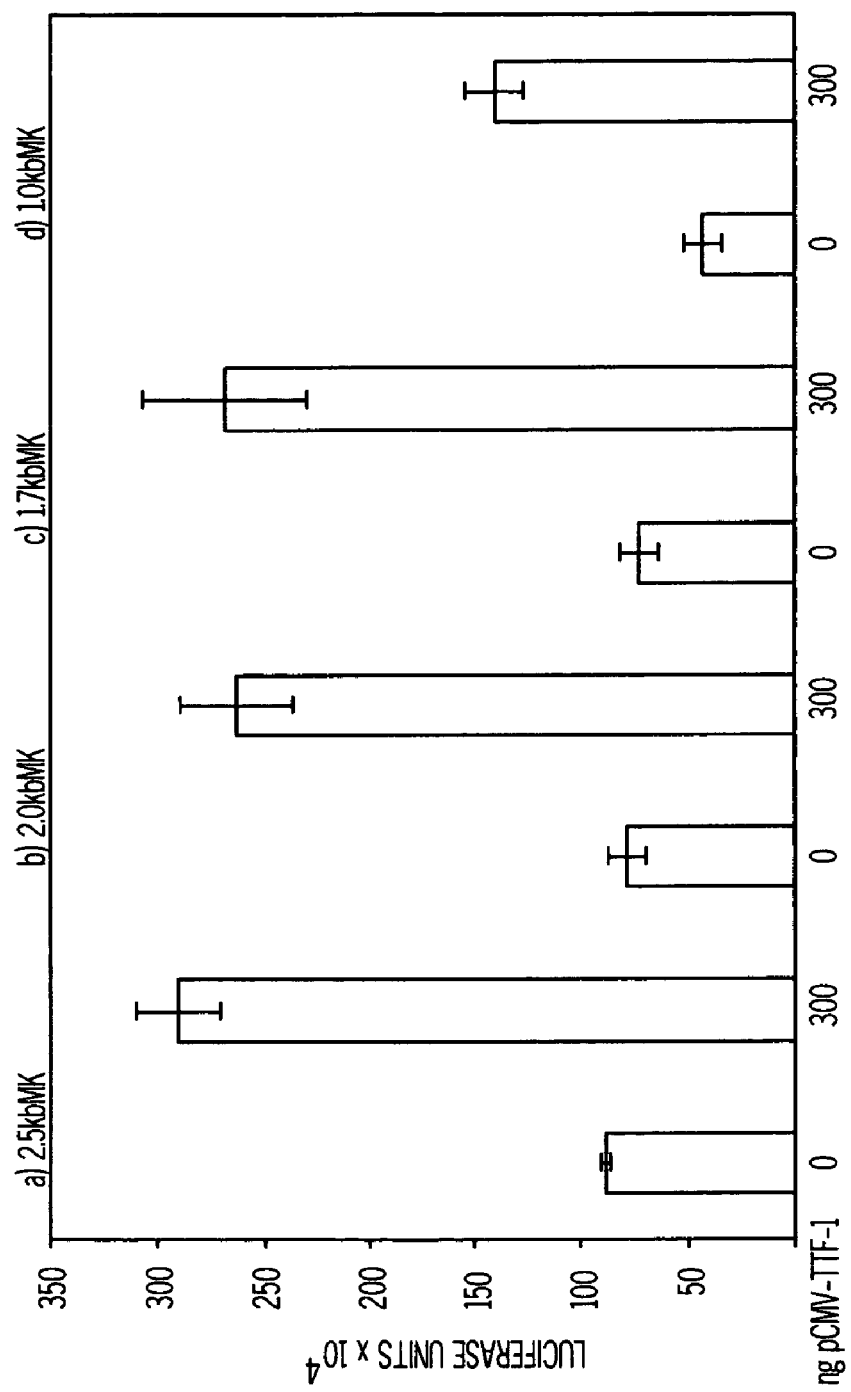

Identification and Isolation of the Murine Midkine Promoter and Truncated Modified Midkine Promoters High fidelity polymerase chain reactions were performed with the Expand Long Template PCR System (Roche, Indianapolis, Ind.). Oligonucleotide primer sequences with Mlu1 restriction sites were designed. The sequence of the upstream primer is set forth in SEQ ID NO:17. The sequence of the downstream primer is set forth in SEQ ID NO:18. After an initial incubation at 94° C. for 1 minute, the reaction mixture underwent 35 cycles of 20 seconds at 94° C., 30 seconds at 57° C., and 2 minutes at 70°C. The amplified fragment was incubated with Mlul to yield a 2.5 kb fragment (SEQ ID NO:7). Subsequently the 2.5 kb fragment was ligated into the pGL3-basic luciferase reporter plasmid (Promega). The construct was sequenced. Three truncated midkine promoter constructs (SEQ ID NO:8, SEQ ID NO:9, and SEQ ID NO:10) were generated with the appropriate upstream primers. The deletion promoters were sequenced also. The modified promoters are diagrammed in FIG. 3.

EXAMPLE 9

Generation of Site Directed Modified Midkine Promoters

For generation of site directed mutations of the midkine promoter, the 2.5 kb Midkine promoter pGL3 -basic reporter construct was used as a template. The site directed alterations were made using the QuickChange™ Site-Directed Mutagenesis kit and following the manufacturer's recommended protocol. Synthetic oligonucleotides comprising the desired mutations were designed to replace six different regions of the promoter. The modified midkine promoters set forth in SEQ ID NOS:11, 12, 13, and 14 each contain a CAAG->CCCC alteration. The modified midkine promoters set forth in SEQ ID NOS:15 and 16 each contain a RCGTG->CTTGC alteration.

Figure 4A:
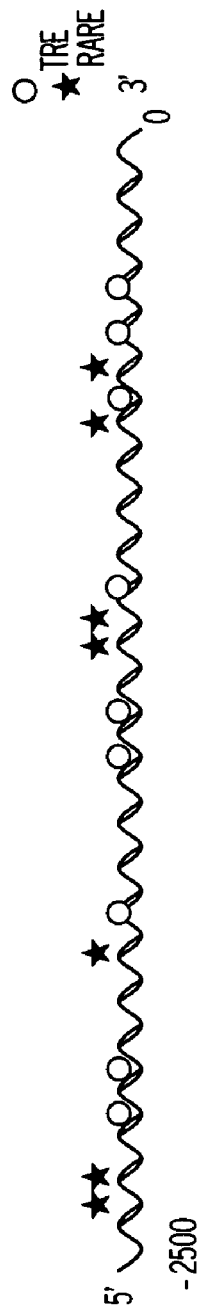
FIG. 4 depicts the wild-type mouse midkine promoter (Panel A), a series of modified midkine promoter constructs (Panel B), and the results obtained from promoter assays (Panel C). In panel A, circles represent potential TTF-1 responsive elements (TREs), and stars represent consensus retinoic acid receptor sites. The modified midkine promoter sequences represented by the diagram in panel B are provided as SEQ ID NO:11 (a), SEQ ID NO:12 (b), SEQ ID NO:13 (c), and SEQ ID NO:14 (d). The promoters were operably linked to a luciferase reporter gene. The promoter assays presented in panel C were performed in JEG cells in the presence (300) or absence (0) of pCMV-TTF-1. The assays were performed using the full length midkine promoter (SEQ ID NO:7), and site directed mutation constructs (SEQ ID NO:11, SEQ ID NO:12, SEQ ID NO:13, and SEQ ID NO:14).
Figure 4B:
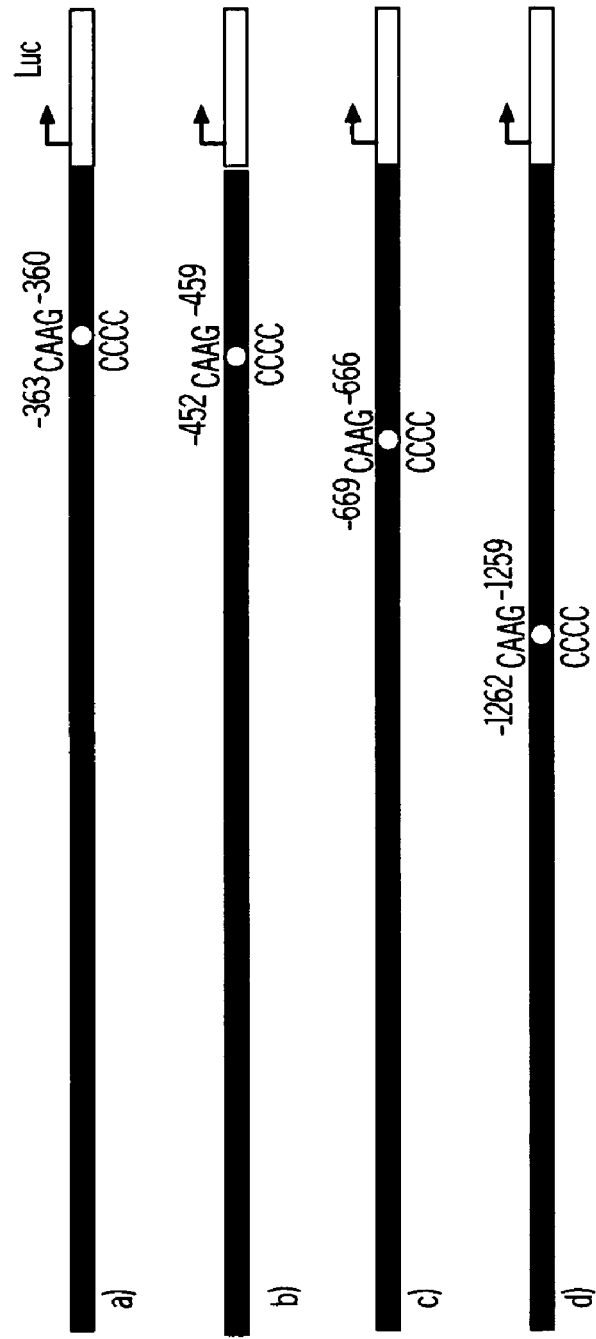
Figure 4C:
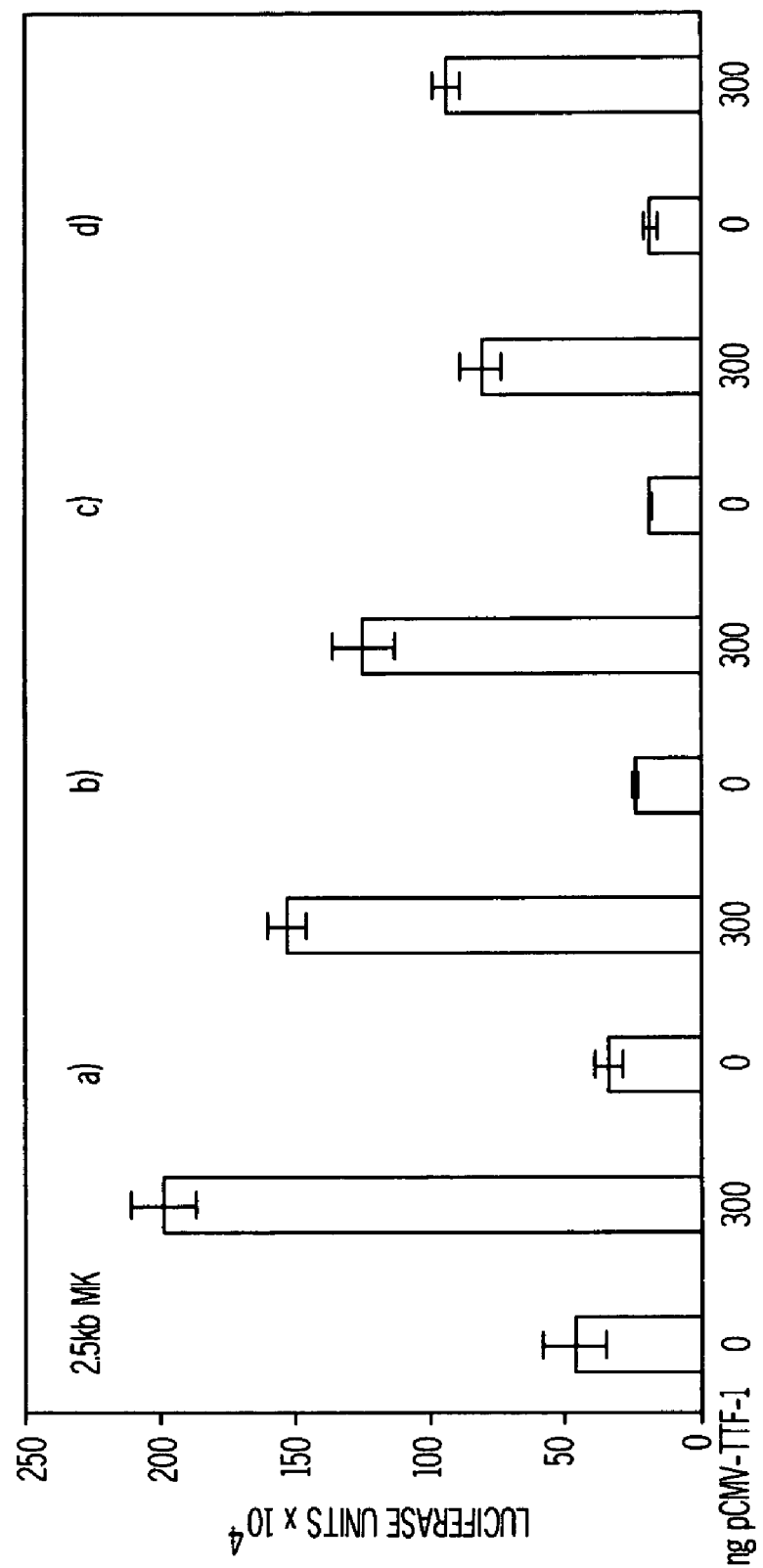
Figure 11:
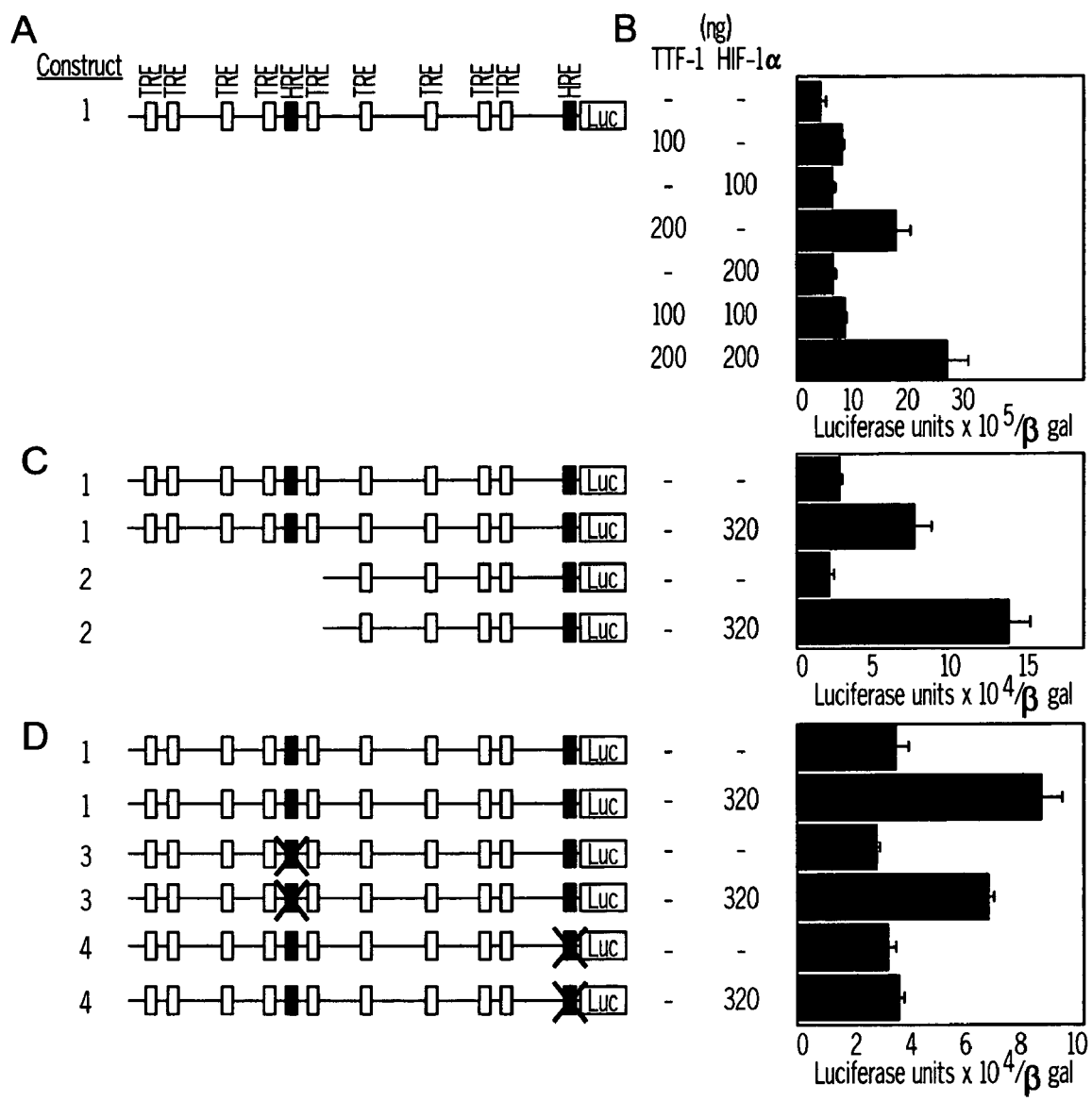
FIG. 11 depicts a schematic of the wild-type midkine promoter and the results of multiple promoter assays assessing the effects of HIF-1α and TTF-1 on the midkine promoter (SEQ ID NO:7) and modified midkine promoters. The promoters were operably linked to a luciferase reporter gene. Panel A presents the wild-type midkine promoter (SEQ ID NO:7). TTF-1 response elements (TRE) are indicated by empty boxes; HIF-1α response elements (HRE) are indicated by solid boxes. In panel B, the wild-type promoter construct and the indicated amount of pCMV-HIF-1α or pCMV-TTF1 were transformed into JEG cells, and promoter assays were performed. Results are indicated in luciferase units X $10^5/\beta$-gal or $10^4/\beta$-gal as indicated. Panel C presents the results of promoter assays performed with the wild-type midkine promoter or a truncated midkine promoter (SEQ ID NO:9). Assays were performed in the presence or absence of 320 ng of pCMV-HIF-1α. Panel D presents the results of promoter assays performed with the wild-type midkine promoter or site directed modified midkine promoters (SEQ ID NO:15 and SEQ ID NO:16). Assays were performed in the presence or absence of 320 ng of pCMV-HIF-1α.

To generate each modified promoter, the appropriate oligonucleotides were used in a PCR reaction with the 2.5 kb midkine promoter pGL3 -basic reporter plasmid. The products of the PCR reaction were digested with Dpnl. The nicked DNA was then transformed into XL1-blue supercompetent cells. Plasmids were isolated, and the modified promoter constructs were confirmed by sequencing. The modified promoters are diagrammed in FIGS. 4 and 11.

EXAMPLE 10

Evaluation of TTF-1 and Midkine and Modified Midkine Promoter Activity

The JEG-3 cell line is a transformed human placental cell line with reduced TTF-1 expression. H-441 is a human epithelial cell line from a pulmonary adenocarcinoma that expresses surfactant protein B (SP-B) and TTF-1. JEG-3 and H-441 cells were grown to 40-50% confluence in 35 mM tissue culture dishes. The cells were transfected with 3 plasmids at the following concentrations: 500 ng/µl pRSV-βGal, 100 ng/µl MK-pGL3basic, and 0, 100, 200, 300,400, or 500 ng/µl pCMV-TTF 1, and pcDNA control vector to bring the total to 1.1 µg total DNA.

After the cells reached confluence, the plates were washed with cold PBS. The cells were lysed, and snap-frozen for several hours. The plates were scraped and the material was centrifuged. The cleared supernatant was used for both luciferase assays and β-galactosidase assays.

B-galactosidase assays were performed as previously described (Bohinski et al. (1994) *Mol. Cell Biol.* 14:5671-5681, herein incorporated by reference in its entirety). Reporter assays were normalized for transfection efficiency based on the β-galactosidase activity. Luciferase activity was determined on 10 µl of extract at room temperature in 100 µl luciferase reagent (Promega) for 10 seconds after a 2 second delay in a Monolight 3010 luminometer. Results from these types of experiments are presented in FIGS. 3 and 4.

EXAMPLE 11

Evaluation of HIF-1α on Midkine and Modified Midkine Promoter Activity

The JEG-3 cell line is a transformed human placental cell line with reduced TTF-1 expression. MFLM-4 is a mouse fetal lung mesenchymal cell line. JEG-3 and MFLM-4 cells were grown to 40-50% confluence in 35 mM tissue culture dishes. The cells were transfected with 3 plasmids at the following concentrations: 500 ng/µl pRSV-βGal, 100 ng/µl 2.5 kb MK-pGL3basic or 1.7 kb MK-pGL3 basic, and 0, 80, 160, 320, or 480 ng/µl pCMV-HIF1-α, and pcDNA control vector to bring the total to 1.08 µg total DNA.

After the cells reached confluence, the plates were washed with cold PBS. The cells were lysed and snap-frozen for several hours. The plates were scraped and the material was centrifuged. The cleared supernatant was used for both luciferase assays and β-galactosidase assays.

B-galactosidase assays were performed as previously described (Bohinski et al. (1994) *Mol. Cell Biol.* 14:5671-5681, herein incorporated by reference in its entirety). Reporter assays were normalized for transfection efficiency based on the β-galactosidase activity. Luciferase activity was determined on 10 µl of extract at room temperature in 100 µl luciferase reagent (Promega) for 10 seconds after a 2 second delay in a Monolight 3010 luminometer. Results from these types of experiments are presented in FIG. 11.

EXAMPLE 12

Generation of Transgenic Mice with an Inducible, Pulmonary Preferred Promoter Onerably Linked to Midkine A pulmonary tissue preferred promoter, the human surfactant protein-C promoter was operably linked to the reverse tetracycline transactivator (rtTA) gene (Perl et al. (2002) *Transgenic Res.* 11:21-29), herein incorporated by reference in its entirety. SP-C-rtTA mice were identified by PCR amplification as described in (Tichelaar et al. (2000) *J. Biol. Chem.* 275:11858-11864), herein incorporated by reference in its entirety.

The (tetO)$_7$-CMV-MK was generated by inserting a 696 base pair mouse midkine cDNA (SEQ ID NO:25) downstream of a minimal CMV promoter containing seven concatamerized tetracycline-receptor binding sites. Transgenic mice were generated by pronuclear injection using standard techniques. Genotypes of transgenic mice were assayed by PCR amplification of a 559 base pair sequence of the transgene with the primers set forth SEQ ID NO:19 and SEQ ID NO:20.

The SP-C-rtTA$^{+/tg}$ mice and (tetO)$_7$-CMV-MK$^{+/tg\ or\ tg/tg}$ mice were bred to yield double transgenic mice (SP-C-rtTA$^{+/tg}$, (tetO)$_7$-CMV-MK$^{+/tg\ or\ tg/tg}$). Transgenic animals were fed doxycycline containing food (625 mg/kg, Harlan Teklad, Madison Wis.).

Transgenic and control mice were housed and maintained under pathogen free conditions in accordance with institutional guidelines. Embryonic day (E) 0 was determined to be the day when formation of a vaginal plug was observed.

EXAMPLE 13

RT-PCR Analysis of Midkine Expression in Transgenic Mice

Lungs were collected from wild-type and double transgenic mice. Total RNA was extracted from the lungs with Trizol® Reagent (Invitrogen) and according to the manufacturer's recommended protocol. Lung RNA was resuspended and quantified. Aliquots of 2 μg total RNA were incubated with 1 μl RNAsin (Promega) and DnaseI (Invitrogen) at room temperature for 15 minuts. The reactions were incubated at 90° C. for 10 minutes. Reverse transcription reactions were performed with the SuperScrip™ II-RT (Invitrogen) according to the manufacturer's recommended protocol.

Figure 10:
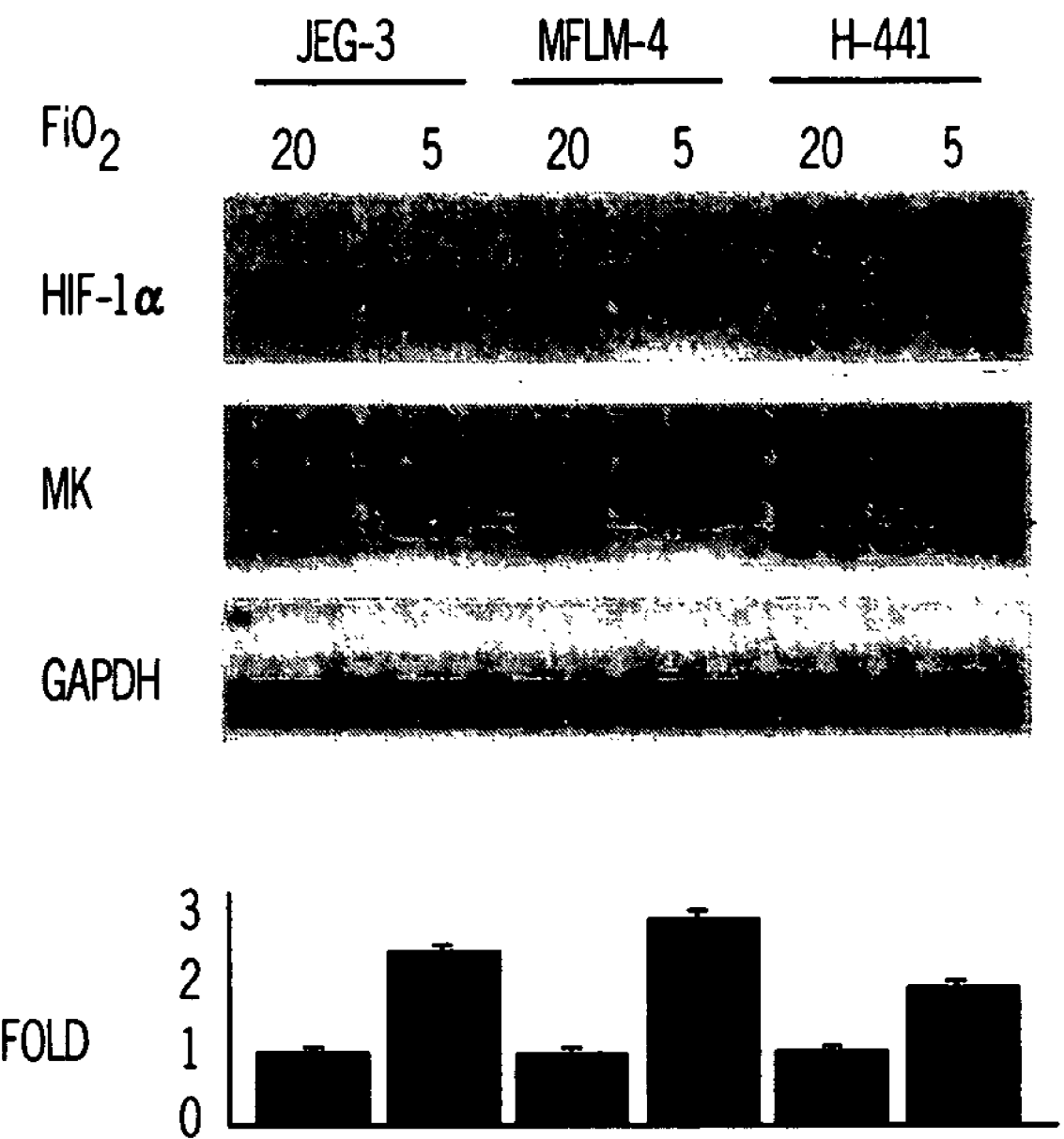
FIG. 10 presents the results obtained from PCR performed on cDNA generated by reverse transcription of RNA isolated from JEG-3 (Lane 2), MFLM-4 (Lane 4), and H-441 (Lane 6) cells after exposure to hypoxia. For comparison RT-PCR was performed on cDNA generated by reverse transcription of RNA isolated from JEG-3 (Lane 1), MFLM-4 (Lane 3), and H-441 (Lane 5) cells maintained in normoxia. Results of the PCR reactions containing HIF-1α primers, midkine primers (MK), and GAPDH primers are indicated. The graph indicates the fold change in midkine expression.

PCR reactions were performed using 2 μl aliquots of the cDNA and Taq polymerase (Roche). Products were run on a 1.5% agarose gel with the appropriate ladder standards. The nucleotide sequences of the primers used to amplify midkine are set forth in SEQ ID NO:21 and SEQ ID NO:22. The nucleotide sequences of the primers used to amplify HIF-1α are set forth in SEQ ID NO:23 and SEQ ID NO:24. The PCR reactions to amplify the midkine fragment underwent 35 cycles of incubation at 94° C. for 30 seconds, 50° C. for 30 seconds, and 72° C. for 45 seconds. The PCR reactions to amplify the HIF-1α fragment underwent 30 cycles of incubation at 94° C. for 30 seconds, 60° C. for 30 seconds, and 72° C. for 1 minute. For comparison, each experiment included two control reactions: one lacking mRNA and one lacking reverse transcriptase. Results obtained from such an analysis are presented in FIG. 10. Details of midkine RT-PCR reactions are described in Reynolds, et al (2004). *J Biol Chem.* 279: 37124-37132 and Reynolds, et al (2003) *Dev Dyn.* 227: 227-237, herein incorporated by reference in their entirety.

EXAMPLE 14

Morphometric Analysis of Right Ventricle Hypertrophy

Mice were sacrificed as described elsewhere herein. Hearts were excised and stored in PBS at 4° C. The total heart mass was determined. The right ventricle (RV) free wall was separated from the left ventricle (LV) and septum (S). The masses of the right ventricle, left ventricle, and septum were determined on an analytical balance. RV hypertrophy (RVH) was mathematically determined based on a ratio of RV/LV+S and RV/full body weight (FBW). Results obtained from such an analysis are presented in FIG. 7.

EXAMPLE 15

Assessment of Distal Pulmonary Vessel Count

Transverse sections of mouse lungs were obtained as described elsewhere herein. The sections were immunostained with PECAM as described elsewhere herein. The analyzer was blinded to the mouse origin of the tissue sections. Three fields in each section of the distal lung were chosen randomly. Vessels (15-50 μm external diameter) associated with alveoli were counted in the distal lung airspaces. Distal lung vessels are arteries associated with alveolar ducts or walls. An average value was calculated. Results from such an analysis are presented in FIG. 7.

EXAMPLE 16

Assessment of Smooth Muscle Cell Induction

Lung sections were immunohistochemically stained with anti-a-SMA monoclonal antibody (Sigma) as described above. The sections were counter-stained with hematoxylin. Vessels with 15-50 μm external diameters associated with distal lung alveolar ducts or walls were identified. The extent of actin staining on each vessel was determined. Vessels with actin staining greater than 75% of the circumference were characterized as fully muscularized. Vessels with actin staining 25-50% of the circumference were characterized as partially muscularized. Vessels with actin staining less than 25% of the circumference were characterized as not muscularized. Results from such an analysis are presented in FIG. 7.

EXAMPLE 17

Assessment of Hypoxia Exposure Effects in Vivo

Double transgenic and wild-type animals were placed in a hypobaric chamber and exposed to 10% O$_2$ for five weeks. The O$_2$ levels (10%) were decreased from normoxic levels (20%) by displacement with N$_2$. The chamber was furnished with regular changes of activated carbon (Fisher Scientific), Drierite (Hammond Drierite Co. LTD., Xenia, Ohio), and Baralyme (Allied Health Care Products, Inc. St. Louis. Mo.). Mice were exposed to 12 hour light and 12 hour dark cycles and were allowed free access to doxycycline containing food and water. Hypoxic conditions were relieved briefly each day to weigh mice, clean cages, and replenish the food and water.

EXAMPLE 18

Evaluation of HIF-1α on Midkine and Modified Midkine Promoter Activity

The JEG-3 cell line is a transformed human placental cell line with reduced TTF-1 expression. JEG-3 cells were grown to 40-50% confluence in 35 mM tissue culture dishes. The cells were transfected with 3 plasmids at the following concentrations: 500 ng/μl pRSV-βGal, 100 ng/μl 2.5 kb MK-pGL3basic, 100 ng/μl 1.7 kb MK-pGL3 basic, 100 ng/μl p2.5 MK(Δ5'HRE)-luc, or 100 ng/μl p2.5 MK(Δ3'HRE)-luc, and 0, 100, or 200 ng/μl pCMV-HIF1-α, and 0, 100, or 200 ng/μl pCMV-TTF-1, and pcDNA control vector to bring the total to 1.08 μg total DNA.

After the cells reached confluence, the plates were washed with cold PBS. The cells were lysed and snap-frozen for several hours. The plates were scraped and the material was centrifuged. The cleared supernatant was used for both luciferase assays and β-galactosidase assays.

B-galactosidase assays were performed as previously described (Bohinski et al. (1994) *Mol. Cell Biol.* 14:5671-5681, herein incorporated by reference in its entirety). Reporter assays were normalized for transfection efficiency based on the β-galactosidase activity. Luciferase activity was determined on 10 μl of extract at room temperature in 100 μl luciferase reagent (Promega) for 10 seconds after a 2 second delay in a Monolight 3010 luminometer. Results from these types of experiments are presented in FIG. 11.

EXAMPLE 19

Assessment of Hypoxia Exposure Effects in Vitro

JEG-3 and MFLM-4 cells were maintained in Modified Eagle's Medium (MEM) and Dulbecco's modified Eagle's medium (DMEM), respectively. The media were supplemented with 10% Fetal Calf Serum, 2 mM glutamine, and antibiotics. Cells were routinely cultured in 5% $CO_2$, 95% air (normoxic conditions) at 37° C. At 80-90% confluence, the cells were divided and plated in 35 mm dishes. The freshly plated cells were grown in normoxic conditions for 18 hours. Half the cultures were then placed into an air-tight chamber (Thermo Forma Series II Water Jacketed $CO_2$ Incubator, Marietta Ohio) infused with a mixture of 5% $CO_2$, 5% $O_2$, and 90% $N_2$ for 4 hours. Cells were then harvested and lysed. Total RNA was collected using the Absolutely RNA® RT-PCR Miniprep Kit (Stratagene) according to the manufacturer's recommended protocol.

EXAMPLE 20

Pulmonary Vascular Remodeling Assessment

In order to assess the effect of midkine on pulmonary vasculature, doxycycline was provided to double transgenic and non-transgenic littermates from conception to post-natal day 21 or from post-natal day 21 to until sacrifice at week 9. Lung tissue sections were prepared as described elsewhere herein. The tissue sections were immunostained for α-SMA as described above herein.

EXAMPLE 21

Pulmonary Arteriograms, Histology, and Arterial Density Quantification

Adult mice were sacrificed with a 26% sodium pentobarbital euthanasia solution and lungs were infused with a heated solution of gelatin and barium through the pulmonary artery using methods known in the art (LeCras et al. (2003) *Am. J. Physiol.* 285:L1046-L1054, herein incorporated by reference). Pulmonary arterial architecture was imaged by X-ray radiography. The left lungs were subsequently embedded in paraffin and sectioned as described elsewhere herein. Barium-filled pulmonary arteries were counted by a blinded observer in randomly selected high-powered (60×) fields of distal lung. Fields containing large airways and/or large vessels were excluded.

EXAMPLE 22

Real-Time RT-PCR

Total RNA was isolated from mouse lungs and reverse transcribed to cDNA. Oligonucleotide SYBR green primer pairs for myocardin and β-actin were generated. Quantitative fluorogenic amplification of cDNA was performed in the Smart Cycler Processing Block, Model #SC1000-1 and using the LightCycler-DNA Master SYBR Green I Kit (available from Roche). The relative abundance of mRNA was determined from standard curves generated from the amplification from serially diluted standard pools of cDNA and normalized to β-actin mRNA.

EXAMPLE 23

Midkine Expression in Human Subjects Exhibiting COPD

Figure 8:
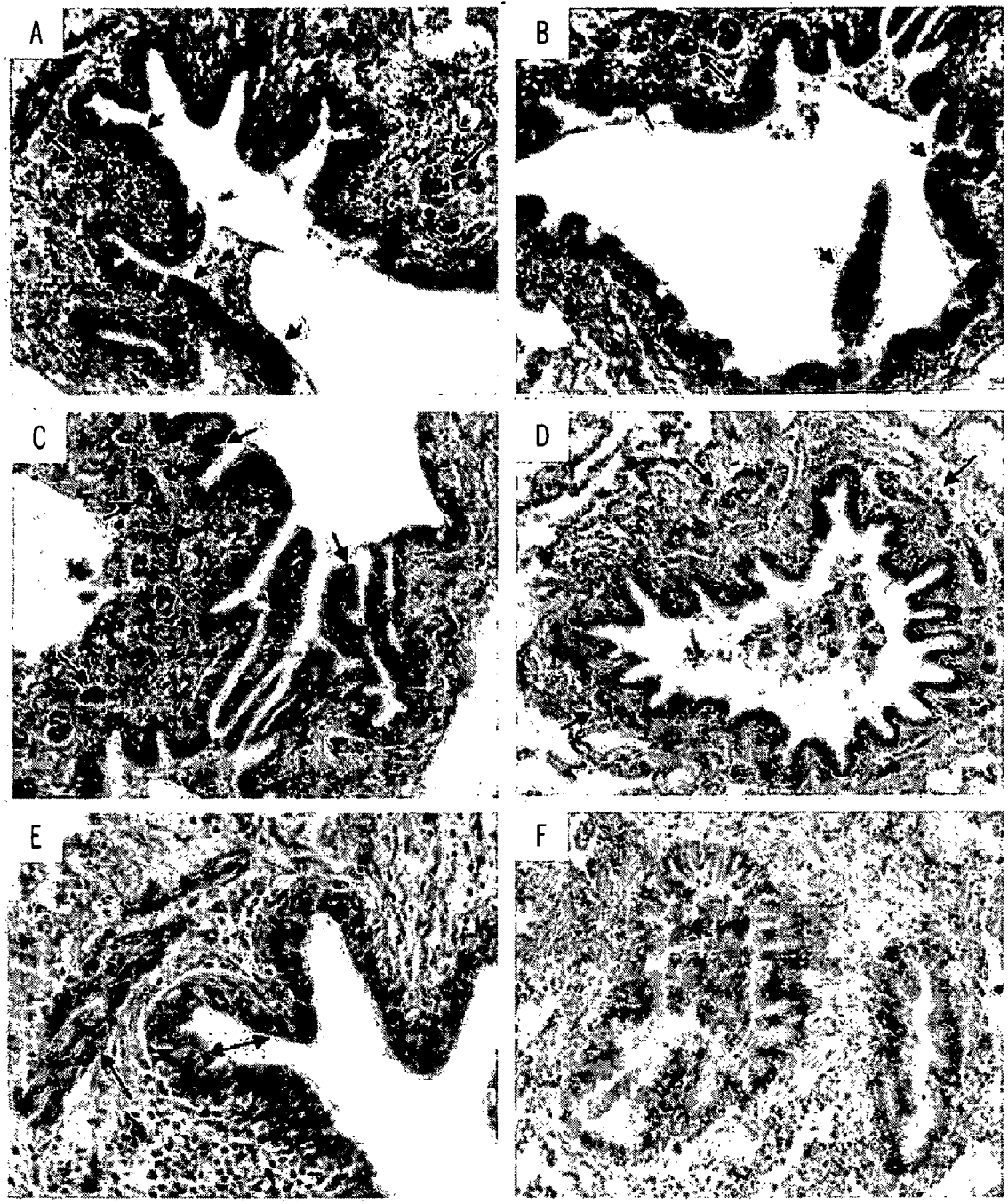
FIG. 8 presents immunostaining of bronchioles and bronchial smooth muscle obtained from human subjects exhibiting a COPD (emphysema). The sections were incubated with anti-midkine antibodies. Panel F was not incubated with primary antibodies.

Pulmonary tissue was obtained from human subjects exhibiting COPD/emphysema. The sections were immunostained with anti-midkine antibodies. Photomicrographs of one such experiment are presented in FIG. 8.

All publications, patents, and patent applications mentioned in the specification are indicative of the level of those skilled in the art to which this invention pertains. All publications, patents, and patent applications are herein incorporated by reference to the same extent as if each individual publication or patent application were specifically and individually incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method of screening for a midkine transcription abnormality, said method comprising:
   (a) providing an isolated nucleic acid molecule comprising an expression cassette comprising a midkine promoter operably linked to a nucleotide sequence encoding a reporter, wherein said promoter comprises a nucleotide sequence selected from the group consisting of: the nucleotide sequence as set forth in SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, and SEQ ID NO:16;
   (b) incubating said isolated nucleic acid molecule with a test sample in vitro;
   (c) assaying the reporter by measuring the expression level or activity of the reporter;
   (d) comparing the expression level of the reporter operably linked to said promoter in the presence of the test sample to the expression level of said reporter operably linked to said promoter in the presence of a control sample; and
   (e) identifying an altered expression level as a midkine transcription abnormality.

2. The method of claim 1, wherein said reporter is selected from the group consisting of: luciferases, blue fluorescent proteins, green fluorescent proteins, CAT, GUS, β-galactosidases, and midkine.

3. The method of claim 1, wherein said isolated nucleic acid molecule is transformed into a cultured cell.

4. The method of claim 1, wherein incubating said isolated nucleic acid molecule with a test sample occurs within a cultured cell.

5. The method of claim 1, wherein said test sample is selected from the group consisting of cell lysates and cellular fractions.

6. A method of identifying a midkine modulating agent, said method comprising:
   (a) providing an isolated nucleic acid molecule comprising an expression cassette comprising a midkine promoter operably linked to a nucleotide sequence encoding a reporter, wherein said promoter comprises a nucleotide sequence selected from the group consisting of: the nucleotide sequence as set forth in SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, and SEQ ID NO:16;
   (b) incubating said isolated nucleic acid molecule with a compound of interest in vitro;
   (c) expressing the isolated nucleic acid molecule in a sample selected from the group consisting of a cell, a cell lysate, a cellular fraction, and a tissue under in vitro conditions in the presence of the compound of interest;
   (d) assaying the reporter by measuring the expression level or activity of the reporter;
   (e) comparing the expression level of the reporter operably linked to said promoter in the presence of said compound of interest to the expression level of said reporter operably linked to said promoter in the absence of said compound of interest; and
   (f) identifying a compound of interest that modulates the expression level of the reporter as a midkine modulating agent.

7. The method of claim 1, wherein the control sample provides a baseline normal expression level of the reporter.

8. The method of claim 1, wherein said promoter comprises the nucleotide sequence as set forth in SEQ ID NO:7.

9. The method of claim 1, wherein said promoter comprises the nucleotide sequence as set forth in SEQ ID NO:8.

10. The method of claim 1, wherein said promoter comprises the nucleotide sequence as set forth in SEQ ID NO:9.

11. The method of claim 1, wherein said promoter comprises the nucleotide sequence as set forth in SEQ ID NO:10.

12. The method of claim 1, wherein said promoter comprises the nucleotide sequence as set forth in SEQ ID NO:11.

13. The method of claim 1, wherein said promoter comprises the nucleotide sequence as set forth in SEQ ID NO:12.

14. The method of claim 1, wherein said promoter comprises the nucleotide sequence as set forth in SEQ ID NO:13.

15. The method of claim 1, wherein said promoter comprises the nucleotide sequence as set forth in SEQ ID NO:14.

16. The method of claim 1, wherein said promoter comprises the nucleotide sequence as set forth in SEQ ID NO:15.

17. The method of claim 1, wherein said promoter comprises the nucleotide sequence as set forth in SEQ ID NO:16.

18. The method of claim 1, wherein the expression cassette further comprises a selectable marker gene.

19. The method of claim 1, wherein the expression level or activity of the reporter is measured with a luminometer.

20. The method of claim 1, wherein the test sample comprises mucosa or a secretion.

21. The method of claim 1, wherein the test sample is obtained from a subject exhibiting a smooth muscle cell disorder.

22. The method of claim 6, wherein said promoter comprises the nucleotide sequence as set forth in SEQ ID NO:7.

23. The method of claim 6, wherein said promoter comprises the nucleotide sequence as set forth in SEQ ID NO:8.

24. The method of claim 6, wherein said promoter comprises the nucleotide sequence as set forth in SEQ ID NO:9.

25. The method of claim 6, wherein said promoter comprises the nucleotide sequence as set forth in SEQ ID NO:10.

26. The method of claim 6, wherein said promoter comprises the nucleotide sequence as set forth in SEQ ID NO:11.

27. The method of claim 6, wherein said promoter comprises the nucleotide sequence as set forth in SEQ ID NO:12.

28. The method of claim 6, wherein said promoter comprises the nucleotide sequence as set forth in SEQ ID NO:13.

29. The method of claim 6, wherein said promoter comprises the nucleotide sequence as set forth in SEQ ID NO:14.

30. The method of claim 6, wherein said promoter comprises the nucleotide sequence as set forth in SEQ ID NO:15.

31. The method of claim 6, wherein said promoter comprises the nucleotide sequence as set forth in SEQ ID NO:16.

32. The method of claim 6, wherein the expression cassette further comprises a selectable marker gene.

33. The method of claim 6, wherein the compound comprises a nucleic acid molecule.

34. The method of claim 6, wherein the compound comprises a peptide or peptidomimetic.

35. The method of claim 6, wherein the compound comprises a small molecule.

36. The method of claim 6, wherein the sample comprises a cultured cell.

37. The method of claim 6, wherein the sample comprises a cell lysate.

38. The method of claim 36, wherein the expression occurs within the cultured cell.

39. The method of claim 6, wherein the expression level or activity of the reporter is measured with a luminometer.

* * * * *

UNITED STATES PATENT AND TRADEMARK OFFICE
CERTIFICATE OF CORRECTION

| | | |
|---|---|---|
| PATENT NO. | : 7,951,532 B2 | Page 1 of 1 |
| APPLICATION NO. | : 10/988486 | |
| DATED | : May 31, 2011 | |
| INVENTOR(S) | : Whitsett et al. | |

It is certified that error appears in the above-identified patent and that said Letters Patent is hereby corrected as shown below:

Title Page Item (56) (OTHER PUBLICATIONS)

Page 1, Col. 2, Line 25, change "alveolization" to --alveolarization--.

Page 2, Col. 2, Line 6, change "MKn" to --MK,--.

Specification

Col. 13, Line 55, change "N-termial" to --N-terminal--.

Col. 14, Line 22, change "protein" to --Protein--.

Col. 25, Line 1, change "12:101 -110;" to --12:101-110;--.

Col. 29, Line 7-8, change "electropermeablization;" to --electropermeabilization;--.

Col. 32, Line 2, change "48hours;" to --48 hours;--.

Col. 32, Line 53, change ""test"" to --"test"--.

Col. 33, Line 3, change "up to3" to --up to 3--.

Col. 36, Line 26 (approx.), change "-administering" to --administering--.

Col. 37, Line 14, change "Pharmigen," to --Pharmingen,--.

Col. 37, Line 65-66, change "Inmmunohistochemistry" to --Immunohistochemistry--.

Col. 38, Line 47, change "$\alpha^{12}P$ to --$\alpha^{32}P$--.

Col. 40, Line 1, change "Dpnl." to --Dpn1.--.

Col. 40, Line 28 (approx.), change "B-galactosidase" to --β-galactosidase--.

Col. 40, Line 59, change "B-galactosidase" to --β-galactosidase--.

Col. 41, Line 3 (approx.), change "Onerably" to --Operably--.

Col. 41, Line 47 (approx.), change "minuts." to --minutes.--.

Col. 41, Line 49, change "SuperScrip™" to --SuperScript™--.

Col. 43, Line 21, change "B-galactosidase" to --β-galactosidase--.

Signed and Sealed this
Tenth Day of January, 2012

David J. Kappos
*Director of the United States Patent and Trademark Office*